(12) United States Patent
Le et al.

(10) Patent No.: US 11,370,833 B2
(45) Date of Patent: Jun. 28, 2022

(54) ANTIBODY FORMULATIONS

(71) Applicant: Genentech, Inc., South San Francisco, CA (US)

(72) Inventors: Lan Le, South San Francisco, CA (US); Brian Connolly, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/026,481

(22) Filed: Jul. 3, 2018

(65) Prior Publication Data

US 2019/0161541 A1 May 30, 2019

Related U.S. Application Data

(63) Continuation of application No. 14/855,325, filed on Sep. 15, 2015, now abandoned.

(60) Provisional application No. 62/050,739, filed on Sep. 15, 2014.

(51) Int. Cl.
| | | |
|---|---|---|
| *C07K 16/22* | (2006.01) | |
| *A61K 39/395* | (2006.01) | |
| *A61K 9/00* | (2006.01) | |
| *A61K 47/26* | (2006.01) | |
| *G01N 33/15* | (2006.01) | |
| *A61K 47/18* | (2017.01) | |

(52) U.S. Cl.
CPC ............ *C07K 16/22* (2013.01); *A61K 9/0019* (2013.01); *A61K 39/3955* (2013.01); *A61K 39/39591* (2013.01); *A61K 47/183* (2013.01); *A61K 47/26* (2013.01); *G01N 33/15* (2013.01); *C07K 2317/14* (2013.01); *C07K 2317/24* (2013.01); *C07K 2317/94* (2013.01)

(58) Field of Classification Search
CPC ................ C07K 16/22; A61K 39/3955; A61K 39/39591; A61K 47/26
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley et al. |
| 4,491,446 A | 1/1985 | Ewald |
| 4,560,655 A | 12/1985 | Baker |
| 4,601,978 A | 6/1986 | Karin |
| 4,657,866 A | 4/1987 | Kumar |
| 4,675,187 A | 6/1987 | Konishi et al. |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,500,362 A | 3/1996 | Robinson et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,591,828 A | 1/1997 | Bosslet et al. |
| 5,625,126 A | 4/1997 | Lonberg et al. |
| 5,631,144 A | 5/1997 | Lemoine et al. |
| 5,633,425 A | 5/1997 | Lonberg et al. |
| 5,641,870 A | 6/1997 | Rinderknecht et al. |
| 5,648,237 A | 6/1997 | Carter |
| 5,661,016 A | 8/1997 | Lonberg et al. |
| 5,736,137 A | 4/1998 | Anderson et al. |
| 5,789,199 A | 8/1998 | Joly et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,054,297 A | 4/2000 | Carter et al. |
| 6,075,181 A | 6/2000 | Kucherlapati et al. |
| 6,150,584 A | 11/2000 | Kucherlapati et al. |
| 6,235,764 B1 | 5/2001 | Larson et al. |
| 6,248,516 B1 | 6/2001 | Winter et al. |
| 6,267,958 B1 * | 7/2001 | Andya ............ A61K 39/39591 424/130.1 |
| 6,417,429 B1 | 7/2002 | Hein et al. |
| 6,420,548 B1 | 7/2002 | Vézina et al. |
| 6,534,524 B1 | 3/2003 | Kania et al. |
| 6,582,959 B2 | 6/2003 | Kim |
| 6,602,684 B1 | 8/2003 | Umaña et al. |
| 6,703,020 B1 | 3/2004 | Thorpe et al. |
| 6,884,879 B1 | 4/2005 | Baca et al. |

(Continued)

FOREIGN PATENT DOCUMENTS

| | | |
|---|---|---|
| CN | 101678103 A | 3/2010 |
| CN | 102770158 A | 11/2012 |

(Continued)

OTHER PUBLICATIONS

Ferrara et al., Biochem. Biophys. Res. Commun., 2005, vol. 333(2):328-335.*

(Continued)

*Primary Examiner* — Xiaozhen Xie

(74) *Attorney, Agent, or Firm* — Morrison & Foerster LLP

(57) ABSTRACT

The invention provides stable aqueous pharmaceutical formulations comprising a therapeutic antibody, trehalose, a buffer, and optional surfactant, and having a pH in the range of about 5.5 to about 7.0. The invention also provides methods for making such formulations and methods of using such formulations.

78 Claims, 10 Drawing Sheets

Specification includes a Sequence Listing.

(56) References Cited

U.S. PATENT DOCUMENTS

| | | |
|---|---|---|
| 6,919,436 B2 | 7/2005 | Lihme et al. |
| 6,919,439 B2 | 7/2005 | Manoharan et al. |
| 6,982,321 B2 | 1/2006 | Winter |
| 7,060,269 B1 | 1/2006 | Baca et al. |
| 7,078,492 B2 | 7/2006 | Pirofski et al. |
| 7,087,409 B2 | 8/2006 | Barbas, III et al. |
| 7,087,492 B2 | 8/2006 | Popp et al. |
| 7,125,978 B1 | 10/2006 | Vézina et al. |
| 7,153,507 B2 | 12/2006 | van de Winkel et al. |
| 7,189,826 B2 | 3/2007 | Rodman |
| 7,910,098 B2 | 3/2011 | Fuh et al. |
| 10,010,611 B2 | 7/2018 | Gokarn et al. |
| 10,925,966 B2 | 2/2021 | Wurth |
| 2003/0190317 A1 | 10/2003 | Baca et al. |
| 2003/0203409 A1 | 10/2003 | Kim et al. |
| 2003/0206899 A1 | 11/2003 | Ferrara et al. |
| 2005/0026229 A1 | 2/2005 | Reiter et al. |
| 2005/0100546 A1 | 5/2005 | Jakobovits et al. |
| 2005/0112126 A1 | 5/2005 | Baca et al. |
| 2005/0176122 A1 | 8/2005 | Lihme et al. |
| 2005/0186208 A1 | 8/2005 | Fyfe et al. |
| 2005/0260186 A1 | 11/2005 | Bookbinder et al. |
| 2005/0287149 A1 | 12/2005 | Keler et al. |
| 2006/0009360 A1 | 1/2006 | Pifer et al. |
| 2006/0059575 A1 | 3/2006 | Kusunoki et al. |
| 2006/0088523 A1* | 4/2006 | Andya ............ A61K 39/39541 424/133.1 |
| 2006/0104968 A1 | 5/2006 | Bookbinder et al. |
| 2006/0183887 A1 | 8/2006 | Jakobovits et al. |
| 2006/0258841 A1 | 11/2006 | Michl et al. |
| 2006/0280747 A1 | 12/2006 | Fuh et al. |
| 2007/0020267 A1 | 1/2007 | Fuh et al. |
| 2007/0141065 A1 | 6/2007 | Fuh et al. |
| 2007/0224203 A1 | 9/2007 | Friess et al. |
| 2009/0162352 A1 | 6/2009 | Adler |
| 2010/0285011 A1 | 11/2010 | Morichika |
| 2011/0171217 A1 | 7/2011 | Badkar et al. |
| 2011/0226650 A1 | 9/2011 | Gokarn et al. |
| 2011/0237506 A1 | 9/2011 | Garigapati et al. |
| 2014/0072559 A1 | 3/2014 | Soula |
| 2014/0127227 A1 | 5/2014 | Chang |
| 2014/0314748 A1 | 10/2014 | Gokarn et al. |
| 2016/0137727 A1 | 5/2016 | Le et al. |
| 2018/0280514 A1 | 10/2018 | Gokarn et al. |
| 2020/0179516 A1 | 6/2020 | Gokarn |

FOREIGN PATENT DOCUMENTS

| | | |
|---|---|---|
| CN | 102573789 B | 9/2015 |
| CN | 101883588 A | 11/2021 |
| DE | 266710 A3 | 4/1989 |
| EP | 0 073 657 A1 | 3/1983 |
| EP | 0 073 657 B1 | 3/1983 |
| EP | 0 183 070 A2 | 6/1986 |
| EP | 0 183 070 A3 | 6/1986 |
| EP | 0 183 070 B1 | 6/1986 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 308 936 A2 | 3/1989 |
| EP | 0 404 097 A2 | 12/1990 |
| EP | 0 404 097 A3 | 12/1990 |
| EP | 0 404 097 B1 | 12/1990 |
| EP | 0 402226 A1 | 12/1990 |
| EP | 0 666 868 B1 | 8/1995 |
| JP | 2011500741 A | 1/2011 |
| JP | 2012-519712 A | 8/2012 |
| JP | 2013-521311 A | 6/2013 |
| RU | 2426554 C2 | 8/2011 |
| WO | WO-1987/00195 A1 | 1/1987 |
| WO | WO 1989/06692 A1 | 7/1989 |
| WO | WO-1990/03430 A1 | 4/1990 |
| WO | WO-1990/13646 A1 | 11/1990 |
| WO | WO-1991/00360 A1 | 1/1991 |
| WO | WO-1991/10741 A1 | 7/1991 |
| WO | WO-1992/09690 A2 | 6/1992 |
| WO | WO-1992/09690 A3 | 6/1992 |
| WO | WO-1992/20373 A1 | 11/1992 |
| WO | WO-1993/01161 A1 | 1/1993 |
| WO | WO-1993/06213 A1 | 4/1993 |
| WO | WO-1993/08829 A1 | 5/1993 |
| WO | WO-1993/11161 A1 | 6/1993 |
| WO | WO-1993/16185 A2 | 8/1993 |
| WO | WO-1993/16185 A3 | 8/1993 |
| WO | WO-1994/04690 A1 | 3/1994 |
| WO | WO-1994/10202 A1 | 5/1994 |
| WO | WO-1994/11026 A2 | 5/1994 |
| WO | WO-1994/11026 A3 | 5/1994 |
| WO | WO-1995/27062 A1 | 10/1995 |
| WO | WO-1996/07754 A1 | 3/1996 |
| WO | WO-1996/27011 A1 | 9/1996 |
| WO | WO-1996/30046 A1 | 10/1996 |
| WO | WO-1996/33735 A1 | 10/1996 |
| WO | WO-1996/34096 A1 | 10/1996 |
| WO | WO-1998/24893 A2 | 6/1998 |
| WO | WO-1998/24893 A3 | 6/1998 |
| WO | WO-1998/45332 A2 | 10/1998 |
| WO | WO-1998/45332 A3 | 10/1998 |
| WO | WO-1999/054342 A1 | 10/1999 |
| WO | WO-2004/035607 A2 | 4/2004 |
| WO | WO-2004/035607 A3 | 4/2004 |
| WO | WO-2004/056312 A2 | 7/2004 |
| WO | WO-2004/056312 A3 | 7/2004 |
| WO | WO-2004/065540 A2 | 8/2004 |
| WO | WO-2004/065540 A3 | 8/2004 |
| WO | WO-2004/113304 A1 | 12/2004 |
| WO | WO-2005/012359 A2 | 2/2005 |
| WO | WO-2005/012359 A3 | 2/2005 |
| WO | WO-2005/044859 A2 | 5/2005 |
| WO | WO-2005/044859 A3 | 5/2005 |
| WO | WO 2005/103081 A2 | 11/2005 |
| WO | WO 2005/103081 A3 | 11/2005 |
| WO | WO-2006/044908 A2 | 4/2006 |
| WO | WO-2006/044908 A3 | 4/2006 |
| WO | WO-2007/031875 A2 | 3/2007 |
| WO | WO-2007/031875 A3 | 3/2007 |
| WO | WO-2008/121615 A2 | 9/2008 |
| WO | WO-2008/121615 A3 | 9/2008 |
| WO | WO2009053038 A2 | 4/2009 |
| WO | WO2009053038 A3 | 6/2009 |
| WO | WO-2009/105534 A2 | 8/2009 |
| WO | WO-2009/105534 A3 | 8/2009 |
| WO | WG-2010/102276 A2 | 9/2010 |
| WO | WG-2010/102276 A3 | 9/2010 |
| WO | WO-2011/012637 A2 | 2/2011 |
| WO | WO-2011/012637 A3 | 2/2011 |
| WO | WO-2011/084750 A1 | 7/2011 |
| WO | WO-2011/109789 A2 | 9/2011 |
| WO | WO-2011/109789 A3 | 9/2011 |
| WO | WO-2012/135408 A1 | 10/2012 |
| WO | WO-2012/146934 A1 | 11/2012 |
| WO | WO-2013/063510 A1 | 5/2013 |
| WO | WO-2014/160490 A1 | 10/2014 |
| WO | WO-2016/044334 A1 | 3/2016 |

OTHER PUBLICATIONS

Saito, S. et al. (2013, e-pub. Jan. 15, 2013). "Effects of Ionic Strength and Sugars on the Aggregation Propensity of Monoclonal Antibodies: Influence of Colloidal and Conformational Stabilities," *Pharm. Res.* 30:1263-1280.

Anderson et al. "Expression of Human B Cell-Associated Antigens on Leukemias and Lymphomas: A Model of Human B Cell Differentiation," *Blood* 63(6):1424-1433, (Jun. 1984).

Barbas et al. "Assembly of Combinatorial Antibody Libraries on Phage Surfaces: The Gene III Site," *Proc. Natl. Acad. Sci. USA*, 88:7978-7982, (Sep. 1991).

Barbas "Semisynthetic Combinatorial Antibody Libraries: A Chemical Solution to the Diversity Problem," *Proc. Natl. Acad. Sci. USA*, 89:4457-4461, (May 1992).

(56) References Cited

OTHER PUBLICATIONS

Barnes et al. "Methods for Growth of Cultured Cells in Serum-Free Medium," *Anal. Biochem.* 102:255-270, (1980).
Bass et al. "Hormone Phage: An Enrichment Method for Variant Proteins with Altered Binding Properties," *Proteins*, 8: 309-314 (1990).
Boerner et al. "Production of Antigen-Specific Human Monoclonal Antibodies from in vitro-Primed Human Splenocytes," *J. Immunol.*, 147(1):86-95, (Jul. 1, 1991).
Brennan et al. "Preparation of Bispecific Antibodies by Chemical Recombination of Monoclonal Immunoglobulin $G_1$ Fragments," *Science*, 229:81-83, (Jul. 5, 1985).
Brodeur et al. "Mouse-Human Myeloma Partners for the Production of Heterohybridomas," *Monoclonal Antibody Production Techniques and Applications* (Marcel Dekker, Inc., New York, 1987), pp. 51-63.
Bruggemann et al. "Designer Mice: The Production of Human Antibody Repertoires in Transgenic Animals," *Year in Immunol.* 7:33-40, (1993).
Carmeliet et al. "Abnormal Blood Vessel Development and Lethality in Embryos Lacking a Single VEGF Allele," *Nature* 380:435-439 (Apr. 4, 1996).
Carter et al. "Humanization of an Anti-p185$^{HER2}$ Antibody for Human Cancer Therapy," *Proc. Natl. Acad. Sci. USA*, 89:4285, (1992).
Carter et al. "High Level *Escherichia coli* Expression and Production of a Bivalent Humanized Antibody Fragment," *Bio/Technology* 10:163-167 (Feb. 1992).
Cavatur et al. "Crystallization Behavior of Mannitol in Frozen Aqueous Solutions," *Pharm. Res.* 19(6):894-900, (Jun. 2002).
Cebe-Suarez et al. "The Role of VEGF Receptors in Angiogenesis; Complex Partnerships," *Cell. Mol. Life Sci.* 63:601-615, (2006).
Champe et al. "Monoclonal Antibodies that Block the Activity of Leukocyte Function-Associated Antigen 1 Recognize Three Discrete Epitopes in the Inserted Domain of CD11a," *J. Biol. Chem.* 270(3):1388-1394, (Jan. 20, 1995).
Charlton "Expression and Isolation of Recombinant Antibody Fragments in *E. coli*," *Methods in Molecular Biology, vol. 248: Antibody Engineering: Methods and Protocols* (B.K.C. Lo © Humana Press Inc. (2003), pp. 245-254.
Chothia et al. "Canonical Structures for the Hypervariable Regions of Immunoglobulins," *J. Mol. Biol.* 196:901-917 (1987).
Clackson et al. "Making Antibody Fragments Using Phage Display Libraries," *Nature*, 352:624-628, (Aug. 15, 1991).
Cleland et al. "The Development of Stable Protein Formulations: A Close Look at Protein Aggregation, Deamidation, and Oxidation," *Critical Reviews in Therapeutic Drug Carrier Systems* 10(4): 307-377, (1993).
Cole et al. "The EBV-Hybridoma Technique and its Application to Human Lung Cancer," *Monoclonal Antibodies and Cancer Therapy* (Alan R. Liss, Inc. New York 1985), pp. 77-96.
Connolly "Vibrational Spectroscopy and Chemometrics to Characterize and Quantitate Trehalose Crystallization," *Anal. Biochem.* 399(1):48-57, (2010. E-pub. Oct. 22, 2009).
Cragg et al. "Complement-Mediated Lysis by Anti-CD20 mAb Correlates with Segregation into Lipid Rafts," *Blood* 101:1045-1052, (Feb. 1, 2003, e-pub. Sep. 19, 2002).
Cragg et al. "Antibody Specificity Controls in vivo Effector Mechanisms of Anti-CD20 Reagents," *Blood* 103:2738-2743, (Apr. 1, 2004, e-pub. Oct. 9, 2003).
Cumming et al. "Glycosylation of Recombinant Protein Therapeutics: Control and Functional Implications," *Glycobiology* 1(2):115-130, (1991).
Duchosal et al. "Immunization of hu-PBL-SCID Mice and the Rescue of Human Monoclonal Fab Fragments Through Combinational Libraries," *Nature* 355:258-262, (Jan. 16, 1992).
Eckhardt et al. "Effect of Freezing on Aggregation of Human Growth Hormone," *Pharm. Res.* 8(11):1360-1364. (1991).

Einfeld et al. "Molecular Cloning of the Human B Cell CD20 Receptor Predicts a Hydrophobic Protein with Multiple Transmembrane Domains," *EMBO J.* 7(3) 711-717, (1988).
Embleton et al. "In-Cell PCR from Mrna: Amplifying and Linking the Rearranged Immunoglobulin Heavy and Light Chain V-Genes Within Single Cells," *Nucl. Acids Res.*, 20(15):3831-3837, (1992).
Even et al. "Serum-Free Hybridoma Culture: Ethical, Scientific and Safety Considerations," *Trends in Biotechnology*, 24(3):105-108, (Mar. 2006, e-pub. Jan. 19, 2006).
Fellouse "Synthetic Antibodies from a Four-Amino-Acid Code: A Dominant Role for Tyrosine in Antigen Recognition," *Proc. Natl. Acad. Sci. USA* 101(34):12467-12472, (Aug. 24, 2004).
Ferrara et al. "Heterozygous Embryonic Lethality Induced by Targeted Inactivation of the VEGF Gene," *Nature* 380:439-442, (Apr. 4, 1996).
Ferrara et al. "The Biology of Vascular Endothelial Growth Factor," *Endocrine Rev.* 18(1):4-25, (Feb. 1997).
Ferrara et al. "Vascular Endothelial Growth Factor is Essential for Corpus Luteum Angiogenesis," *Nature Med.* 4(3):336-340, (Mar. 1998).
Ferrara et al. "Molecular and Biological Properties of Vascular Endothelial Growth Factor," *J. Mol. Med.* 77:527-543 (1999).
Ferrara et al. "Clinical Applications of Angiogenic Growth Factors and Their Inhibitors," *Nature Medicine* 5(12):1359-1364, (Dec. 1999).
Ferrara et al. "Bevacizumab (Avastin), A Humanized Anti-VEGF Monoclonal Antibody For Cancer Therapy," *Biophys. Res. Commun.* 333(2):328-335, (2005, e-pub. Jun. 2, 2005).
Fishwild et al. "High-Avidity Human IgGκ Monoclonal Antibodies from a Novel Strain of Minilocus Transgenic Mice," *Nature Biotechnol.* 14:845-851, (Jul. 1996).
Fleer et al. "Stable Multicopy Vectors for High-Level Secretion of Recombinant Human Serum Albumin by *Kluyveromyces* Yeasts," *Bio/Technology*, 9:968-975, (Oct. 1991).
Franek "Oligopeptides as Tools for Improving Productivity of Hybridoma Cells Cultures," *Trends in Monoclonal Antibody Research* pp. 111-122, (2005).
Genbank Accession No. NP-690605, last updated May 3, 2014, located at http://www.ncbi.nlm.nih.gove/protein/NP_690605, last visited Mar. 5, 2015, two pages.
Gerber et al. "VEGF Couples Hypertrophic Cartilage Remodeling, Ossification and Angiogenesis During Endochondral Bone Formation," *Nature Med.* 5(6):623-628, (Jun. 1999).
Gerngross "Advances in the Production of Human Therapeutic Proteins in Yeasts and Filamentous Fungi," *Nat. Biotech.* 22(11):1409-1414, (Nov. 2004, e-pub. Nov. 4, 2004).
Goding "Production and Application of Monoclonal Antibodies in Cell Biology, Biochemistry and Immunology," *Monoclonal Antibodies: Principles and Practice* (Academic Press 1983), pp. 59-103.
Graham et al. "Characteristics of Human Cell Line Transformed by DNA from Human Adenovirus Type 5," *J. Gen Virol.* 36:59-72, (1977).
Gram et al. "In Vitro Selection and Affinity Maturation of Antibodies from a Naïve Combinatorial Immunoglobulin Library," *Proc. Natl. Acad. Sci. USA*, 89:3576-3580, (Apr. 1992).
Griffiths et al. "Human Anti-Self Antibodies with High Specificity from Phage Display Libraries," *EMBO.* 12(2):725-734, (1993).
Gruber et al. "Efficient Tumor Cell Lysis Mediated by a Bispecific Single Chain Antibody Expressed in *Escherichia coli*," *J. Immuno.* 152:5368-5374, (1994).
Guerrin et al. "Vasculotropin/Vascular Endothelial Growth Factor is an Autocrine Growth Factor for Human Retinal Pigment Epithelial Cells Cultured in vitro," *J. Cell Physiol.* 164 :385-394, (1995).
Guss et al. "Structure of the IgG-Binding Regions of Streptococcal Protein G," *EMBO J.* 5(7):1567-1575, (1986).
Ham et al. "Basic Methods: Media and Growth Requirements," *Meth. Enz.* 58:44-93, (1979).
Hamers-Casterman et al. "Naturally Occurring Antibodies Devoid of Light Chains," *Nature* 363:446-448, (Jun. 3, 1993).
Hammerling et al. "Production of Hybridomas in the Rodent System," *Monoclonal Antibodies and T-Cell Hybridomas*, (Elsevier/North Holland Biomedical Press. Amsterdam 1981), pp. 563-681.

(56) References Cited

OTHER PUBLICATIONS

Harlow et al. *Antibodies: A Laboratory Manual*, (Cold Spring Harbor Laboratory Press, 2nd ed. 1988).
Harris "Therapeutic Monoclonals: Production of Humanized Monoclonal Antibodies for in vivo Imaging and Therapy," *Biochem. Soc. Transactions* 23:1035-1038, (1995).
Hawkins et al. "Selection of Phage Antibodies by Binding Affinity: Mimicking Affinity Maturation," *J. Mol. Biol.* 226:889-896, (1992).
Hogrefe et al. "A Bacteriophage Lambda Vector for the Cloning and Expression of Immunoglobulin Fab Fragments on the Surface of Filamentous Phage," *Gene* 128:119-126, (1993).
Holliger et al. "'Diabodies': Small Bivalent and Bispecific Antibody Fragments," *Proc. Natl. Acad. Sci. USA* 90:6444-6448, (Jul. 1993).
Hongo S. et al. "Development and Characterization of Murine Monoclonal Antibodies to the Latency-Associated Peptide of Transforming Growth Factor $\beta_1$," *Hybridoma* 14(3):253-260, (1995).
Hoogenboom et al. "Multi-Subunit Proteins on the Surface of Filamentous Phage Methodologies for Displaying Antibody (Fab) Heavy and Light Chains," *Nucl. Acids Res.* 19(15):4133-4137, (1991).
Hoogenboom et al. "By-Passing Immunisation: Human Antibodies from Synthetic Repertoires of Germline $V_H$ Gene Segments Rearranged in Vitro" *J. Mol. Biol.* 227:381-388, (1992).
Hoogenboom et al. "Overview of Antibody Phage-Display Technology and its Applications," *Methods in Molecular Biology* vol. 178:Antibody Phage Display: Methods and Protocols, (P.M. O'Brien and R. Altken © Humana Press Inc., Totowa, N.J. 2001), pp. 1-37.
Houck et al. "The Vascular Endothelial Growth Factor Family: Identification of a Fourth Molecular Species and Characterization of Alternative Splicing of RNA," *Mol. Endocrin.* 5:1806-1814, (1991).
Hudson et al. "Engineered Antibodies," *Nat. Med.* 9(1):129-134, (Jan. 2003).
Hurle et al. "Protein Engineering Techniques for Antibody Humanization," *Curr. Op. Biotech.* 5:428-433, (1994).
Inn, WHO Drug Information, 25(1):75-76, (2011).
Inn, WHO Drug Information, 22(2):124, (2008).
Inn, WHO Drug Information, 23(2):176, (2009).
Inn, WHO Drug Information, 26(4):453, (2012).
Izutsu et al. "Decreased Protein-Stabilizing Effects of Cryoprotectants Due to Crystallization," *Pharm. Res.* 10(8):1232-1237, (Aug. 1993).
Izutsu et al. "Effect of Mannitol Crystallinity on the Stabilization of Enzymes During Freeze-Drying," *Chem. Pharm. Bull.* 42(1):5-8, (1994).
Jakobovits et al. "Germ-Line Transmission and Expression of a Human-Derived Yeast Artifical Chromosome," *Nature* 362:255-258, (Mar. 18, 1993).
Jakobovits et al. "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551, (Mar. 1993).
Jefferis et al. "IgG-Fc-Mediated Effector Functions: Molecular Definition of Interaction Sites for Effector Ligands and the Role of Glycosylation," *Immunol. Rev.* 163:59-76, (1998).
Jenkins et al. "Getting the Glycosylation Right: Implications for the Biotechnology Industry," *Nature Biotechnol.* 14:975-981, (Aug. 1996).
Johnson et al. "The Kabat Database and a Bioinformatics Example," *Methods in Molecular Biology* 248:1-25, (2003).
Jones "Proteinase Mutants of *Saccharomyces cerevisiae*," *Genetics*, 85:23-33, (Jan. 1977).
Jones et al. "Replacing the Complementarity-Determining Regions in a Human Antibody with Those from a Mouse," *Nature* 321:522-525, (May 29, 1986).
Jones et al. "Rapid PCR-Cloning of Full-Length Muse Immunoglobulin Variable Regions," *Biotechnol.* 9:88-89, (Jan. 1991).
Jones "Analysis of Polypeptides and Proteins," A. *Adv. Drug Delivery Rev.* 10:29-90, (1993).
Klagsbrun et al. "Regulators of Angiogenesis," *Annu. Rev. Physiol.* 53:217-239, (1991).

Kohler et al. "Continuous Cultures of Fused Cells Secreting Antibody of Predefined Specificity," *Nature*, 256:495-97, (Aug. 7, 1975).
Komaromy et al. (Oct. 11, 1983). "The Structure of the Mouse Immunoglobulin in $\gamma_3$ Membrane Gene Segment," *Nucl. Acid Res.* 11 (19):6775-6785.
Kostelny et al. "Formation of a Bispecific Antibody by the Use of Leucine Zippers," *J. Immunol.*, 148(5):1547-1553, (Mar. 1, 1992).
Kozbor "A Human Hybrid Myeloma for Production of Human Monoclonal Antibodies," *J. Immunol.*, 133(6):3001-3005, (Dec. 1984).
Lee et al. "High-Affinity Human Antibodies from Phage-Displayed Synthetic Fab Libraries with a Single Framework Scaffold," *J. Mol. Biol.* 340(5):1073-1093, (2004).
Lee et al. "Bivalent Antibody Phage Display Mimics Natural Immunoglobulin," *J. Immunol. Methods* 284(1-2):119-132, (2004).
Leung et al. "Vascular Endothelial Growth Factor is a Secreted Angiogenic Mitogen," *Science* 246:1306-1309, (Dec. 9, 1989).
Leung et al. "A Method for Random Mutagenesis of A Defined DNA Segment Using a Modified Polymerase Chain Reaction," *Technique* 1(1):11-15 (Aug. 1989).
Li et al. "Optimization of Humanized IgGs in Glycoengineered *Pichia pastoris*," *Nat. Biotech.* 24(2):210-215, (Feb. 2006, e-pub. Jan. 22, 2006).
Li et al. "Human Antibodies for Immunotherapy Development Generated via a Human B Cell Hybridoma Technology," *Proc. Natl. Acad. Sci. USA*, 103(10):3557-3562, (Mar. 7, 2006).
Liang et al. "Cross-Species Vascular Endothelial Growth Factor (VEGF) Blocking Antibodies Completely Inhibit the Growth of Human Tumor Xenografts and Measure the Contribution of Stromal VEGF," *J Biol Chem* 281 (2):951-961, (Jan. 13, 2006).
Lifely et al. "Glycosylation and Biological Activity of CAMPATH-1H Expressed in Different Cell Lines and Grown Under Different Culture Conditions," *Glycobiology* 5(8):813-822, (1995).
Lindmark et al. "Binding of Immunoglobulins to Protein A and Immunoglobulin Levels in Mammalian Sera," *J. Immunol. Meth.* 62:1-13, (1983).
Lonberg et al. "Antigen-Specific Human Antibodies from Mice Comprising Four Distinct Genetic Modifications," *Nature* 368:856-859, (Apr. 28, 1994).
Lonberg et al. "Human Antibodies from Transgenic Mice," *Intern. Rev. Immunol.* 13:65-93, (1995).
Marks et al. "By-Passing Immunization: Human Antibodies from V-Gene Libraries Displayed on Phage," *J. Mol. Biol.* 222:581-597, (1991).
Marks et al. "By-Passing Immunization: Building High Affinity Human Antibodies by Chain Shuffling," *Bio/Technology* 10:779-783, (Jul. 1992).
Mather "Establishment and Characterization of Two Distinct Mouse Testicular Epithelial Cell Lines," *Biol. Reprod.* 23:243-251, (1980).
Mather et al. "Culture of Testicular Cell in Hormone-Supplemented Serum-Free Medium," *Annals N.Y. Acad. Sci.* 383:44-68, (1982).
Matsuda et al. "Structure and Physical Map of 64 Variable Segments in the 3' 0.8-Megabase Region of the Human Immunoglobulin Heavy-Chain Locus," *Nature Genet.* 3(1):88-94, (Jan. 1993).
Miller et al. "Thermophysical Properties of Trehalose and its Concentrated Aqueous Solutions," *Pharm. Res.* 14(5):578-590, (1997).
Milstein et al. "Hybrid Hybridomas and Their Use in Immunohistochemistry," *Nature* 305:537-539, (1983).
Morimoto et al. "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117, (1992).
Morrison et al. "Chimeric Human Antibody Molecules: Mouse Antigen-Binding Domains with Human Constant Region Domains," *Proc. Natl. Acad. Sci. USA* 81:6851-6855, (Nov. 1984).
Morrison. "Success in Specification," *Nature* 368:812-813, (Apr. 28, 1994).
Munson et al. "LIGAND: A Versatile Computerized Approach for Characterization of Ligand-Binding Systems," *Anal. Biochem.* 107:220-239, (1980).

(56) References Cited

OTHER PUBLICATIONS

Murakami et al. "Cell Cycle Regulation, Oncogenes, and Antineoplastic Drugs," in *The Molecular Basis of Cancer*, Chapter 1 (W.B. Saunders Company, Philadelphia, 1995), pp. 3-16.

Neuberger "Generating High-Avidity Human Mabs in Mice," *Nature Biotechnol.* 14:826, (Jul. 1996).

Ni "Research Progress and Future Perspectives in Antibodomics and Antibodomic Drugs," *Xiandai Mianyixue* 26(4):265-268, (Oct. 23, 2006).

Nicolaou et al. "Calicheamicin $\theta^I_1$: A Rationally Designed Molecule with Extremely Potent and Selective DNA Cleaving Properties and Apoptosis Inducing Activity," *Angew. Chem. Intl. Ed. Engl.* 33(2):183-186, (1994).

Oberg-Welsh et al. "Effects of Vascular Endothelial Growth Factor on Pancreatic Duct Cell Replication and the Insulin Production of Fetal Islet-Like Cell Clusters in vitro," *Mol. Cell. Endocrinol.* 126:125-132, (1997).

Orlandi et al. "Cloning Immunoglobulin Variable Domains for Expression by the Polymerase Chain Reaction," *Proc. Natl. Acad. Sci. USA* 86:3833-3837, (May 1989).

Orum et al. "Efficient Method for Constructing Comprehensive Murine Fab Antibody Libraries Displayed on Phage," *Nucleic Acids Res.* 21(19):4491-4498, (1993).

Pearlman et al. "Analysis of Protein Drugs," Chapter 6 in *Peptide and Protein Drug Delivery*, (Lee, V.H.L., Marcel Dekker, Inc., New York, New York, 1991), pp. 247-297.

Pluckthun "Mono- and Bivalent Antibody Fragments Produced in *Escherichia coli*: Engineering, Folding and Antigen Binding," Immunol. Revs. 130:151-188, (1992).

Pluckthün "Antibodies from *Escherichia coli*," *The Pharmacology of Monoclonal Antibodies*, vol. 113, Rosenburg and Moore eds., (Springer-Verlag, New York, 1994), pp. 269-315.

Popkov et al. "Human/Mouse Cross-Reactive Anti-VEGF Receptor 2 Recombinant Antibodies Selected from an Immune b9 Allotype Rabbit Antibody Library," *Journal of Immunological Methods* 288:149-164, (2004).

Poppema et al. "Preparation and Application of Monoclonal Antibodies: B Cell Panel and Paraffin Tissue Reactive Panel," *Biotest Bulletin* 3:131-139, (1987).

Presta "Antibody Engineering," *Curr. Op. Struct. Biol.* 2:593-596, (1992).

Presta et al. "Humanization of an Antibody Directed Against IgE," *J. Immunol.* 151(5):2623-2632, (Sep. 1, 1993).

Presta et al. "Humanization of an Anti-Vascular Endothelial Growth Factor Monoclonal Antibody for the Therapy of Solid Tumors and Other Disorders," *Cancer Res.* 57:4593-4599, (Oct. 15, 1997).

Reff et al. "Depletion of B Cells in vivo by a Chimeric Mouse Human Monoclonal Antibody to CD20," *Blood* 83(2):435-445, (Jan. 15, 1994).

Reyes et al. "Expression of Human β-Interferon cDNA Under the Control of a Thymidine Kinase Prompter from Herpes Simplex Virus," *Nature* 297:598-601, (Jun. 17, 1982).

Riechmann et al. "Reshaping Human Antibodies for Therapy," *Nature* 332:323-329, (Mar. 24, 1988).

Sastry et al. "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728-5732, (Aug. 1989).

Sato "Molecular Diagnosis of Tumor Angiogenesis and Anti-Angiogenic Cancer Therapy," *Int. J. Clin. Oncol.* 8:200-206, (2003).

Schüle, S. et al. (Aug. 2008, e-pub. Feb. 19, 2008). "Stabilization of IgG1 in Spray-Dried Powders for Inhalation," *Eur. J. Pharm. Biopharm.* 69(3):793-807.

Sehn, L.H. et al. (May 31, 2012, e-pub. Mar. 20, 2012) "A Phase 1 Study of Obinutuzumab Induction Followed by 2 Years of Maintenance in Patients with Relapsed CD20-Positive B-Cell Malignancies," *Blood* 119(22):5118-5125.

Shalaby, M.R. et al. "Development of Humanized Bispecifc Antibodies Reactive with Cytotoxic Lymphocytes and Tumor Cells Overexpressing the HER2 Protooncogene," *J. Exp. Med.* 175:217-225, (Jan. 1, 1992).

Sharma et al. "Effect of Vacuum Drying on Protein-Mannitol Interactions: The Physical State of Mannitol and Protein Structure in the Dried State," *AAPS PharmSciTech.* 5(1):E10, (2004).

Sheriff et al. "Redefining the Minimal Antigen-Binding Fragment," *Nature Struct. Biol.* 3(9):733-736, (Sep. 1996).

Sidhu et al. "Phage-Displayed Antibody Libraries of Synthetic heavy Chain Complementarity Determining Regions," *J. Mol. Biol.* 338(2):299-310, (2004).

Sims et al. "A Humanized CD18 Antibody Can Block Function Without Cell Destruction," *J. Immunol.* 151(4):2296-2308, (Aug. 15, 1993).

Skerra et al. "Bacterial Expression of Immunoglobulin Fragments," *Curr. Opinion in Immunol.* 5:256-262, (1993).

Sondell et al. "Vascular Endothelial Growth Factor has Neutrotrophic Activity and Stimulates Axonal Outgrowth, Enhancing Cell Survival and Schwann Cell Proliferation in the Peripheral Nervous System," *J. Neurosci.* 19(14):5731-5740, (Jul. 15, 1999).

Stamenkovic. et al. "Analysis of Two cDNA Clones Encoding the B Lymphocyte Antigen CD20 (B1, Bp35), a Type III Intergral Membrane Protein," *J. Exp. Med.* 167:1975-1980, (Jun. 1988).

Stinchcomb et al. "Isolation and Characterisation of a Yeast Chromosomal Replicator," *Nature* 282:39-43, (Nov. 1, 1979).

Streit et al. "Angiogenesis, Lymphangiogenesis, and Melanoma Metastasis," *Oncogene* 22:3172-3179, (2003).

Suresh et al. "Bispecific Monoclonal Antibodies from Hybrid Hybridomas," *Methods in Enzymology*, 121:210-228, (1986).

Tedder et al. (Aug. 1985). "The B Cell Surface Molecule B1 is Functionally Linked with B Cell Activation and Differentiation," *J. Immunol.* 135(2):973-979.

Tedder et al. (1986). "Antibodies Reactive with the B1 Molecule Inhibit Cell Cycle Progression but Not Activation of Human B Lymphocytes," *Eur. J. Immunol.* 16(8):881-887.

Tedder et al. "Isolation and Structure of a cDNA Encoding the B1 (CD20) Cell-Surface Antigen of Human B Lymphocytes," *Proc. Natl. Acad. Sci. U.S.A.* 85:208-212, (Jan. 1988).

Tedder et al. "Structure of the Gene Encoding the Human B Lymphocyte Differentiation Antigen CD20 (B1)1," *J. Immunol.* 142(7):2560-2568, (Apr. 1, 1989).

Tedder, T.F. et al. "Receptor-Modulated Transport System," *J. Cell Biochem.* 14D:195, (1990).

Tomlinson et al. "The Repertoire of Human Germline $V_H$ Sequences Reveals About Fifty Groups of $V_H$ Segments with Different Hypervariable Loops," *J. Mol. Biol.* 227:776-798, (1992).

Tonini et al. "Molecular Basis of Angiogenesis and Cancer," *Oncogene* 22:6549-6556, (2003).

Traunecker et al. "Bispecific Single Chain Molecules (Janusins) Target Cytotoxic Lymphocytes on HIV Infected Cells," *EMBO J.* 10(12):3655-3659, (1991).

Tutt et al. "Trispecific F(ab')$_3$ Derivatives That Use Cooperative Signaling Via the TEC/CD3 Complex and CD2 to Activate and Redirect Resting Cytotoxic T Cells," *J. Immunol.* 147(1):60-69, (Jul. 1, 1991).

Umana et al. "Engineered Glycoforms of an Antineuroblastoma IgG1 with Optimized Antibody-Dependent Cellular Cytotoxic Activity," *Nature Biotechnol.* 17:176-180,m (Feb. 1999).

Urlaub et al. "Isolation of Chinese Hamster Cell Mutants Deficient in Dihydrofolate Reductase Activity," *Proc. Natl. Acad. Sci. USA* 77:4216-4220, (Jul. 1980).

Valentine et al. "Phosphorylation of the CD20 Phosphoprotein in Resting B Lymphocytes," *J. Biol. Chem.* 264(19):11282-11287, (Jul. 5, 1989).

Van Den Berg "*Kluyveromyces* as a Host for Heterologous Eene Expression: Expression and Secretion of Prochymosin," *Bio/Technology*, 8:135-139, (Feb. 1990).

Van Dijk et al. "Human Antibodies as Next Geeration Therapeutics," *Curr. Opin. Pharmacol.* 5:368-74, (2001).

Vaswani et al. "Humanized Antibodies as Potential Therapeutic Drugs," *Ann. Allergy, Asthma & Immunol.* 1:105-115, (Aug. 1998).

(56) References Cited

OTHER PUBLICATIONS

Verhoeyen et al. "Reshaping Human Antibodies: Grafting an Antilysozyme Activity," *Science*, 239:1534-1536, (1988).
Vollmers et al. "Death by Stress: Natural IgM-Induced Apoptosis," *Methods and Findings in Experimental and Clinical Pharmacology*, 27(3):185-191, (2005).
Vollmers et al. "The 'Early Birds': Natural IgM Antibodies and Immune Surveillance," *Histology and Histopathology* 20(3):927-937, (2005).
Ward et al. "Binding Activities of a Repertoire of Single Immunoglobulin Variable Domains Secreted from *Escherichia coli*," *Nature*, 341:544-546, (Oct. 12, 1989).
Waterhouse et al. "Combinational Infection and in vivo Recombination: A Strategy for Making large Phage Antibody Repertoires," *Nucl. Acids Res.* 21(9):2265-2266, (1993).
Williams et al. "Cloning and Sequencing of Human Immunoglobulin $V_\lambda$ Gene Segments," *Eur. J. Immunol.* 23:1456-1461, (1993).
Winter et al. "Making Antibodies by Phage Display Technology," *Ann. Rev. Immunol.* 12:433-455, (1994).
Wright et al. "Effect of Glycosylation on Antibody Function: implications for Genetic Engineering," *Trends Biotech.* 15:26-32, (Jan. 1997).
Xu et al. "Diversity in the CDR3 Region of $V_H$ is Sufficient for Most Antibody Specificities," *Immunity* 13:37-45, (Jul. 2000).
Yaniv "Enhancing Elements for Activation of Eukaryotic Promoters," *Nature* 297:17-18, (May 6, 1982).
Yazaki et al. "Expression of Recombinant Antibodies in Mammalian Cell Lines," *Methods in Molecular Biology.* vol. 248 (B. K. C. Lo, ed., Humana Press, Totowa, N.J., 2003), pp. 255-268.
Zapata et al. "Engineering Linear F(ab')2 Fragments for Efficient Production in *Escherichia coli* and Enhanced Antiproliferative Activity," *Protein Eng.* 8(10):1057-1062, 1995).
Expert Declaration of Y. John Wang, dated Sep. 20, 2016, 14 pages.
Extended European Search Report dated Sep. 21, 2016, for EP Patent Application No. 14772646.7, filed on Jun. 14, 2014, 8 pages.
International Preliminary Report On Patentability or PCT Application No. PCT/US2015/050278, dated Mar. 21, 2017, filed Sep. 15, 2015, 13 pages.
International Search Report dated Jun. 27, 2014, for PCT Application No. PCT/US2014/026824, filed Mar. 13, 2014, five pages.
International Search Report dated Feb. 18, 2016, for PCT Application No. PCT/US2015/050278, filed on Sep. 15, 2016, 13 pages.
Invitation To Pay Additional Fees mailed on Dec. 3, 2015, for PCT Application No. PCT/US2015/050278, filed on Sep. 15, 2015, 9 pages.
Written Opinion for PCT Application No. PCT/US2014/026824, dated Jun. 27, 2014, filed Mar. 13, 2014, 11 pages.
Written Opinion for PCT Application No. PCT/US2015/050278, filed on Sep. 15, 2016, 12 pages.
European Office Action, dated Apr. 8, 2019, for European Patent Application No. 15772124.2, 7 pages.
Wang, W. et al. "Antibody Structure, Instability, and Formulation," J. of Pharmaceutical Sciences 96(1): 1-26 (Jan. 2007).
WHO Drug Information. (2008), Proposed Inn List 99 International Nonproprietary Names for Pharmaceutical Substances, World Health Organization, Geneva, Switzerland, 22(2):77, 78, & 124.
WHO Drug Information. (2009). International Nonproprietary Names for Pharmaceutical Substances, World Health Organization, Geneva, Switzerland, 23(2):176.
WHO Drug information. (2011). International Nonproprietary Names for Pharmaceutical Substances, World Health Organization, Geneva, Switzerland, 25(1):75-76.
WHO Drug information. (2012). International Nonproprietary Names for Pharmaceutical Substances, World Health Organization, Geneva, Switzerland, 26(4):453.
U.S. Appl. No. 16/723,864, filed Dec. 20, 2019, Gokarn et al.
Jain, N.K. et al. (Jan. 2009; E-pub Dec. 2, 2008) "Effect of Trehalose On Protein Structure," Protein Sci. 18(1):24-36.
Ohtake, S. et al. (Oct. 2011, e-pub. Jul. 1, 2011). "Interactions of Formulation Excipients With Proteins in Solution and in the Dried State," Adv. Drug Deliv. Rev. 63(13): 1053-1073.
Singh, S.S. et al. (2011, e-pub. Jan. 7, 2011). "Frozen State Storage Instability of a Monoclonal Antibody Aggregation as a Consequence of Trehalose Crystallizaton and Protein Unfolding," Pharm. Res. 28:873-885.
Avastin® (Bevacizumab) (2005). "Scientific Discussion," European Medicine Agency, 61 pages.
Avastin® (Bevacizumab) (Sep. 2011). "Highlights of Prescribing Information," FDA Label, 25 pages.
European Examination Report Office Action, dated Jul. 29, 2021, for European Patent Application No. 15772124.2, 9 pages.

* cited by examiner

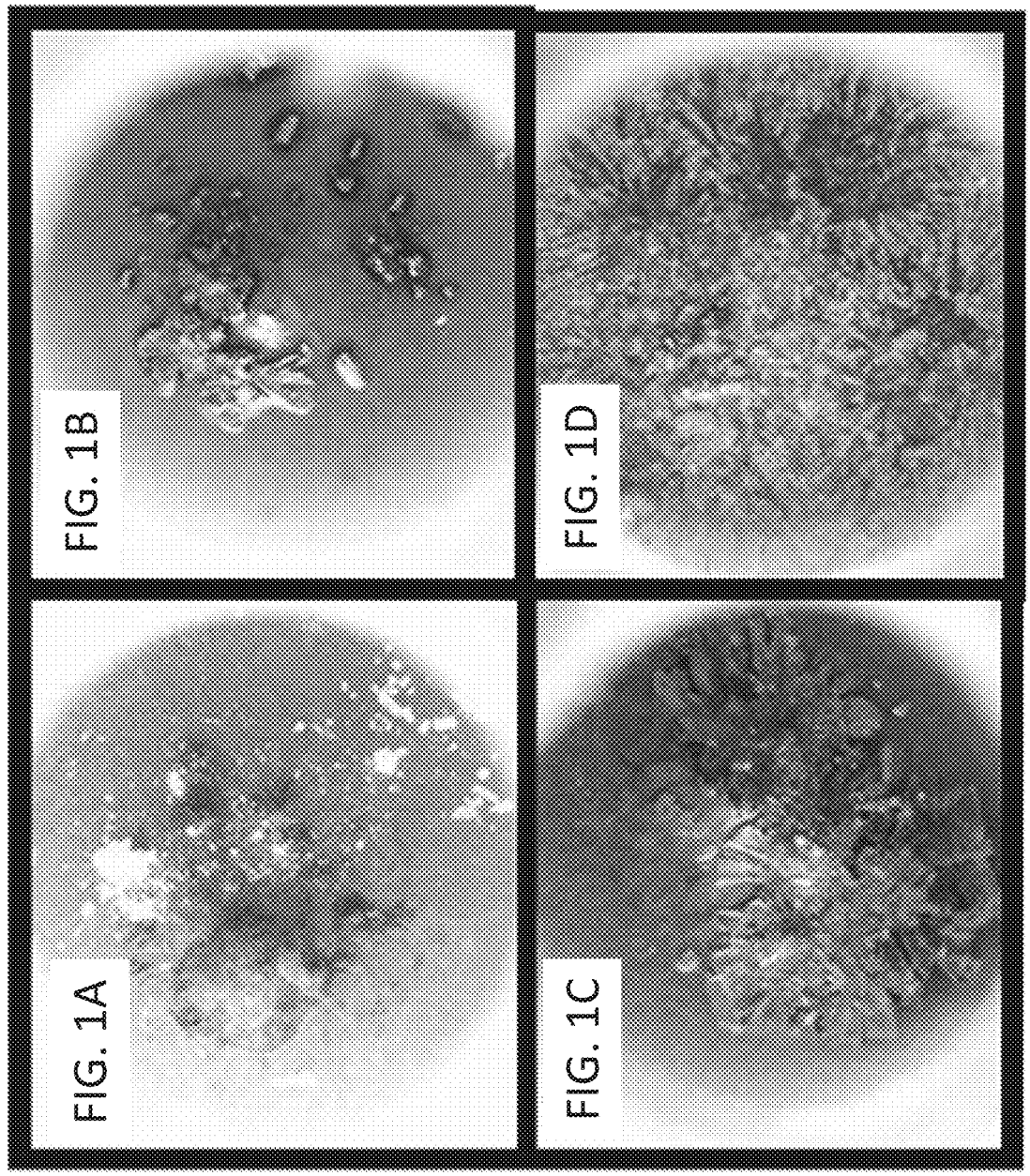

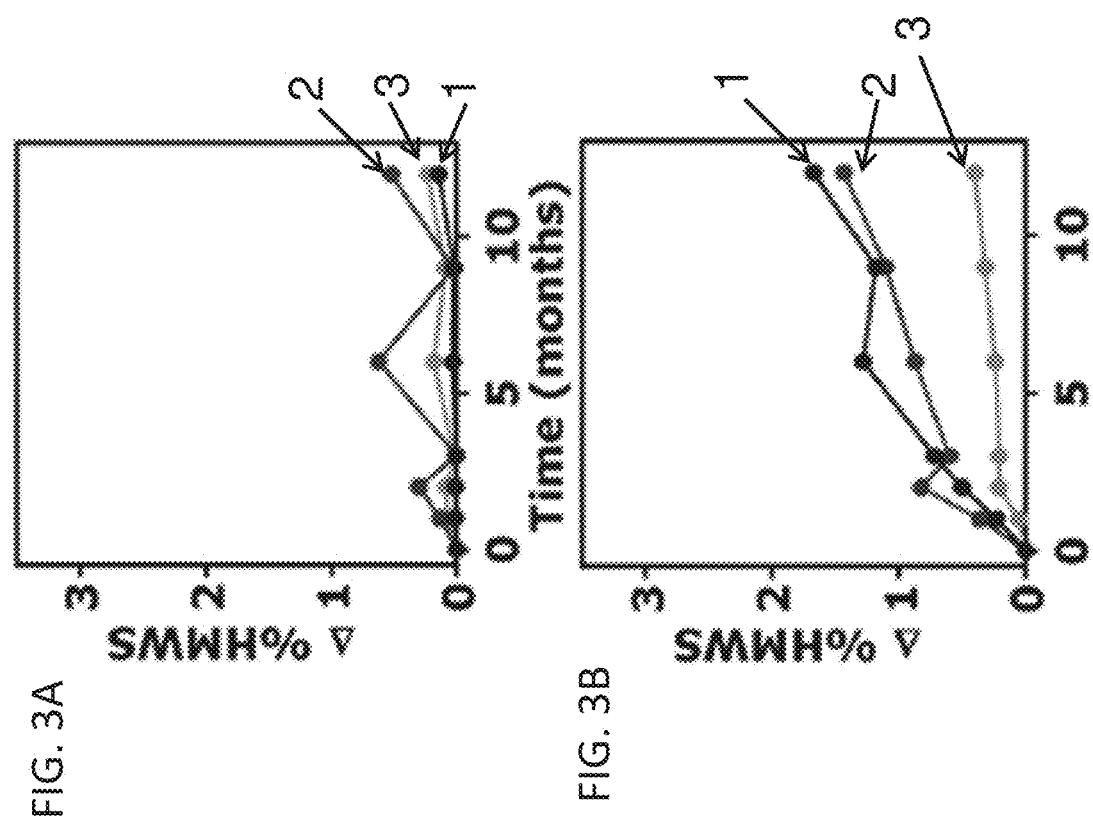

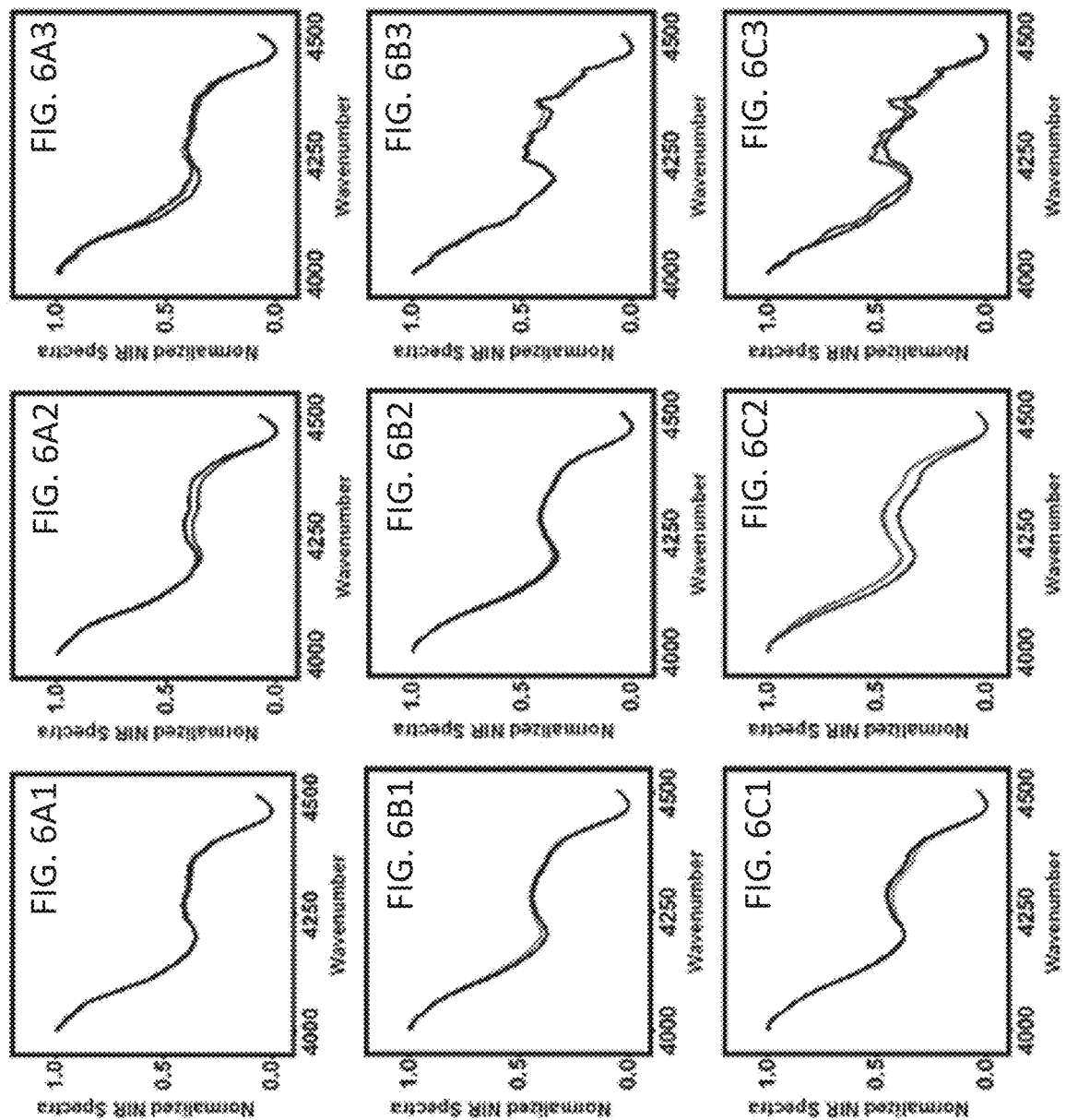

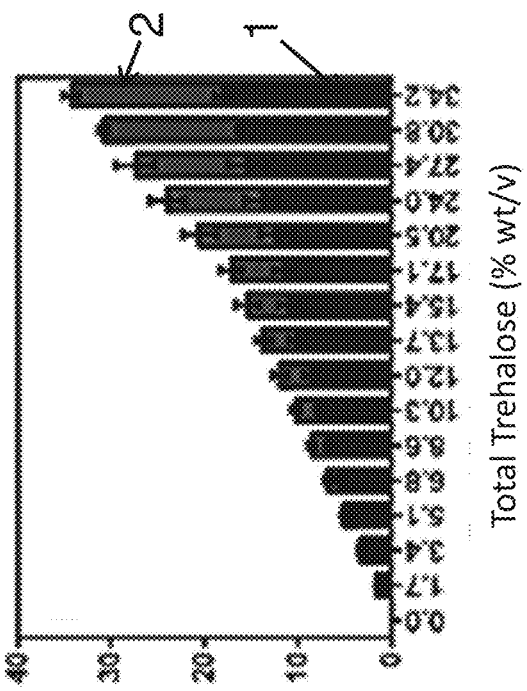
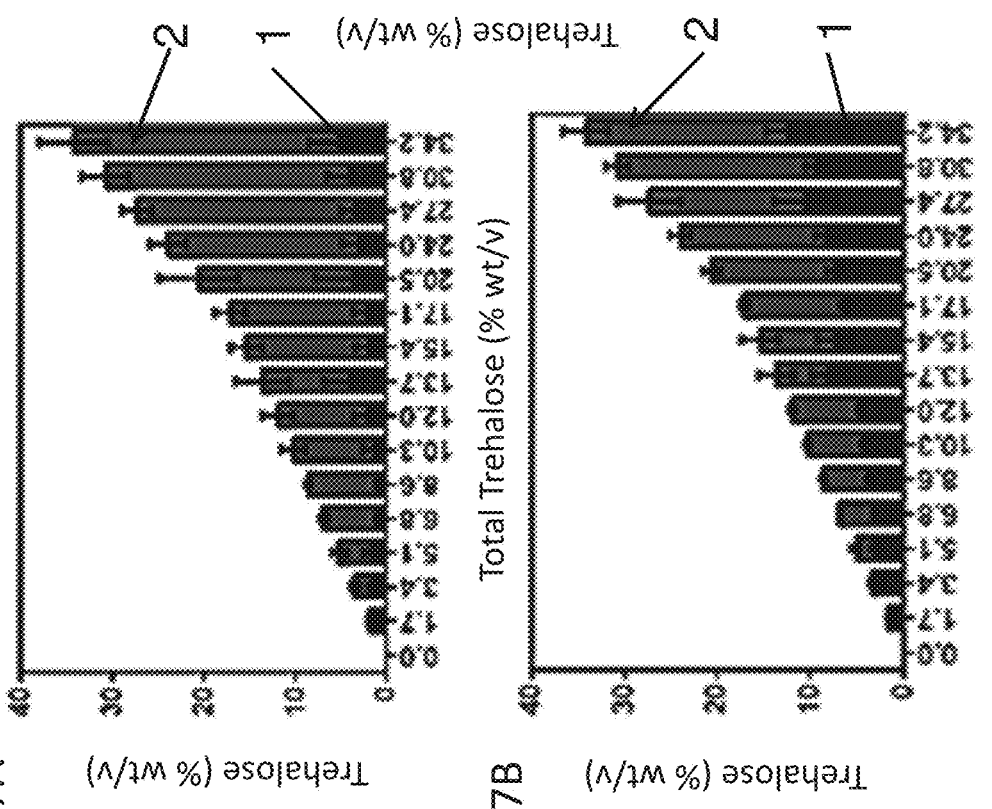
FIG. 7A
FIG. 7B
FIG. 7C

SEQUENCE LISTING

```
<160> NUMBER OF SEQ ID NOS: 22

<210> SEQ ID NO 1
<211> LENGTH: 112
<212> TYPE: PRT
<213> ORGANISM: Mus sp.
<220> FEATURE:
<223> OTHER INFORMATION: amino acid sequence of variable region of the
      heavy chain (VH) of murine monoclonal anti-CD20
      antibody B-Ly1

<400> SEQUENCE: 1

Gly Pro Glu Leu Val Lys Pro Gly Ala Ser Val Lys Ile Ser Cys Lys
 1               5                  10                  15

Ala Ser Gly Tyr Ala Phe Ser Tyr Ser Trp Met Asn Trp Val Lys Leu
            20                  25                  30

Arg Pro Gly Gln Gly Leu Glu Trp Ile Gly Arg Ile Phe Pro Gly Asp
        35                  40                  45

Gly Asp Thr Asp Tyr Asn Gly Lys Phe Lys Gly Lys Ala Thr Leu Thr
    50                  55                  60

Ala Asp Lys Ser Ser Asn Thr Ala Tyr Met Gln Leu Thr Ser Leu Thr
65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
            100                 105                 110

<210> SEQ ID NO 2
<211> LENGTH: 103
<212> TYPE: PRT
<213> ORGANISM: Mus sp.
<220> FEATURE:
<223> OTHER INFORMATION: amino acid sequence of variable region of the
      light chain (VL) of murine monoclonal anti-CD20
``` antibody B-Ly1

<400> SEQUENCE: 2

Asn Pro Val Thr Leu Gly Thr Ser Ala Ser Ile Ser Cys Arg Ser Ser
1               5                   10                  15

Lys Ser Leu Leu His Ser Asn Gly Ile Thr Tyr Leu Tyr Trp Tyr Leu
            20                  25                  30

Gln Lys Pro Gly Gln Ser Pro Gln Leu Leu Ile Tyr Gln Met Ser Asn
        35                  40                  45

Leu Val Ser Gly Val Pro Asp Arg Phe Ser Ser Gly Ser Gly Thr
    50                  55                  60

Asp Phe Thr Leu Arg Ile Ser Arg Val Glu Ala Glu Asp Val Gly Val
65                  70                  75                  80

Tyr Tyr Cys Ala Gln Asn Leu Glu Leu Pro Tyr Thr Phe Gly Gly Gly
                85                  90                  95

Thr Lys Leu Glu Ile Lys Arg
            100

<210> SEQ ID NO 3
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH2)

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH3)

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

```
Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Leu Cys
                 85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 5
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH4)

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Ala Phe Ser Tyr Ser
             20                  25                  30

Trp Met Asn Trp Val Arg Gln Ala Pro Gly Gln Gly Leu Glu Trp Met
         35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH5)

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Tyr Ser
             20                  25                  30

Trp Met Ser Trp Val Arg Gln Ala Pro Gly Gln Gly Leu Glu Trp Met
         35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 7
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH6)

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH7)

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Ser Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 9

```
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH8)

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HH9)

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL8)

<400> SEQUENCE: 11
```

-continued

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 12
<211> LENGTH: 119
<212> TYPE: PRT
<213> ORGANISM: Artificial Sequence
<220> FEATURE:
<223> OTHER INFORMATION: amino acid sequences of variable region of the heavy chain (VH) of humanized B-Ly1 antibody (B-HL10)

<400> SEQUENCE: 12

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 13
<211> LENGTH: 119
<212> TYPE: PRT
<213> ORGANISM: Artificial Sequence
<220> FEATURE:
<223> OTHER INFORMATION: amino acid sequences of variable region of the heavy chain (VH) of humanized B-Ly1 antibody (B-HL11)

<400> SEQUENCE: 13

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45
```

Gly Arg Ile Phe Pro Gly Asp Gly Asp Thr Asp Tyr Asn Gly Lys Phe
            50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 14
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL12)

<400> SEQUENCE: 14

Glu Val Gln Leu Val Glu Ser Gly Ala Gly Leu Val Lys Pro Gly Gly
  1               5                  10                  15

Ser Leu Arg Leu Ser Cys Ala Ala Ser Gly Phe Thr Phe Ser Tyr Ser
                 20                  25                  30

Trp Met Asn Trp Val Arg Gln Ala Pro Gly Lys Gly Leu Glu Trp Met
             35                  40                  45

Gly Arg Ile Phe Pro Gly Asp Gly Asp Thr Asp Tyr Asn Gly Lys Phe
            50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL13)

<400> SEQUENCE: 15

Glu Val Gln Leu Val Glu Ser Gly Gly Gly Val Val Lys Pro Gly Gly
  1               5                  10                  15

Ser Leu Arg Leu Ser Cys Ala Ala Ser Gly Phe Thr Phe Ser Tyr Ser
                 20                  25                  30

Trp Met Asn Trp Val Arg Gln Ala Pro Gly Lys Gly Leu Glu Trp Met
             35                  40                  45

Gly Arg Ile Phe Pro Gly Asp Gly Asp Thr Asp Tyr Asn Gly Lys Phe
            50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

```
Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL14)

<400> SEQUENCE: 16

Glu Val Gln Leu Val Glu Ser Gly Gly Gly Leu Lys Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL15)

<400> SEQUENCE: 17

Glu Val Gln Leu Val Glu Ser Gly Gly Gly Leu Val Lys Pro Gly Ser
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 18
<211> LENGTH: 119
```

```
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL16)

<400> SEQUENCE: 18

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Artificial Sequence
<220> FEATURE:
<223> OTHER INFORMATION: amino acid sequences of variable region of the
      heavy chain (VH) of humanized B-Ly1 antibody (B-HL17)

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 20
<211> LENGTH: 115
<212> TYPE: PRT
<213> ORGANISM: Artificial Sequence
<220> FEATURE:
<223> OTHER INFORMATION: amino acid sequences of variable region of the
      light chain (VL) of humanized B-Ly1 antibody B-KV1

<400> SEQUENCE: 20

Asp Ile Val Met Thr Gln Thr Pro Leu Ser Leu Pro Val Thr Pro Gly
```

```
1               5                   10                  15
Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
                35                  40                  45

Pro Gln Leu Leu Ile Tyr Gln Met Ser Asn Leu Val Ser Gly Val Pro
                50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

Arg Thr Val
        115

<210> SEQ ID NO 21
<211> LENGTH: 449
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
                35                  40                  45

Gly Arg Ile Phe Pro Gly Asp Gly Asp Thr Asp Tyr Asn Gly Lys Phe
                50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                    245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 22
<211> LENGTH: 219
<212> TYPE: PRT
<213> ORGANISM: Artificial Sequence
<220> FEATURE:
<223> OTHER INFORMATION: Synthetic Construct

<400> SEQUENCE: 22

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

ANTIBODY FORMULATIONS

CROSS-REFERENCE TO RELATED APPLICATIONS

This application is a continuation of U.S. patent application Ser. No. 14/855,325, filed on Sep. 15, 2015, which claims the priority benefit of U.S. Provisional Application No. 62/050,739, filed on Sep. 15, 2014, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392028201SEQLIST.TXT, date recorded: Jul. 2, 2018, size: 29 KB).

FIELD OF THE INVENTION

This invention relates to stable aqueous pharmaceutical formulations comprising antibodies.

BACKGROUND OF THE INVENTION

In the past years, advances in biotechnology have made it possible to produce a variety of proteins for pharmaceutical applications using recombinant DNA techniques. Because proteins are larger and more complex than traditional organic and inorganic drugs (e.g., possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (e.g., any process which involves modification of the protein by bond formation or cleavage resulting in a new chemical entity) or physical instability (e.g., changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland et al., *Critical Reviews in Therapeutic Drug Carrier Systems* 10(4): 307-377 (1993).

Included in the proteins used for pharmaceutical applications are antibodies. Stable acqueous formulations have been developed for pharmaceutical antibodies. See, e.g., WO 2011/084750. There is still a need in the art for a stable aqueous pharmaceutical formulation comprising an antibody, such as an anti-VEGF antibody and an anti-CD20 antibody, which mitigates formation of dimers, soluble aggregates, and particulates.

SUMMARY

In one aspect, the invention provides a stable aqueous pharmaceutical formulation, the formulation comprising a monoclonal antibody, trehalose and a buffer, wherein the weight ratio of the monoclonal antibody to the trehalose in the formulation is greater than or equal to 0.41 and less than 1.65, and wherein the formulation has a pH of about 5.5 to about 7.0. In some embodiments, the weight ratio of the monoclonal antibody to the trehalose is 0.49 to 1.47. In some embodiments, the weight ratio of the monoclonal antibody to the trehalose is about 0.41 to 0.73. In some embodiments, the weight ratio of the monoclonal antibody to the trehalose is about 0.73 to 1.47. In some embodiments, the weight ratio of the monoclonal antibody to the trehalose is any of 0.41, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, and 1.64, including every value in between these numbers. In some embodiments, the monoclonal antibody in the formulation is about 25 mg/mL to about 100 mg/mL. In some embodiments, the monoclonal antibody in the formulation is about 45 mg/mL to about 55 mg/mL. In some embodiments, the monoclonal antibody in the formulation is about 35 mg/mL to about 75 mg/mL. In some embodiments, the trehalose in the formulation is about 45 mM to about 634 mM. In some embodiments, the trehalose in the formulation is about 50 mM to about 600 mM. In some embodiments, the trehalose in the formulation is about 150 mM to about 400 mM. In some embodiments, the trehalose in the formulation is about 45 mM to about 135 mM. In some embodiments, the trehalose in the formulation is about 180 mM to about 634 mM. In some embodiments, the buffer is an amount of about 15 mM to about 100 mM. In some embodiments, the buffer is an amount of greater than 35 mM to about 100 mM. In some embodiments, the buffer comprises histidine (e.g., histidine acetate, histidine hydrochloride) or phosphate (e.g., sodium phosphate).

In another aspect, the invention provides stable aqueous pharmaceutical formulations comprising (a) a monoclonal antibody in an amount of about 25 mg/mL to about 100 mg/mL; (b) trehalose in an amount of about 45 mM to about 634 mM; and (c) sodium phosphate in an amount of greater than 35 mM to about 100 mM, wherein said formulation has a pH of about 5.5 to about 7.0, wherein the weight ratio of said monoclonal antibody to said trehalose in the formulation is greater than or equal to 0.41 and less than 1.65, and an optional surfactant. In some embodiments, the weight ratio of the monoclonal antibody to the trehalose in the formulation is 0.41 to 0.73. In some embodiments, the weight ratio of the monoclonal antibody to the trehalose is 0.73 to 1.47. In some embodiments, the weight ratio of the monoclonal antibody to the trehalose is 0.49 to 1.47. In some embodiments, the weight ratio of the monoclonal antibody to the trehalose is any of 0.41, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, and 1.64, including every value in between these numbers.

In another aspect, the invention provides a stable aqueous pharmaceutical formulation, the formulation comprising (a) an antibody (e.g., a monoclonal antibody) in an amount of less than or equal to about 100 mg/mL; and (b) trehalose in an amount of about 150 mM to about 400 mM, wherein said formulation has a pH of about 5.5 to about 7.0, and wherein the weight ratio of said monoclonal antibody to said trehalose in the formulation is greater than or equal to 0.41 and less than 1.65. In some embodiments, the formulation is for subcutaneous administration. In some embodiments, the formulation is for intraocular administration. In some embodiments, the formulation is isotonic. In some embodiments, the formulation has an osmolality of greater than about 240 mOsm/kg.

In another aspect, the invention provides a stable aqueous pharmaceutical formulation, the formulation comprising (a) an antibody (e.g., a monoclonal antibody) in an amount of less than or equal to about 100 mg/mL; and (b) trehalose in an amount of about 50 mM to about 600 mM, wherein said formulation has a pH of about 5.5 to about 7.0, and wherein the weight ratio of said monoclonal antibody to said trehalose in the formulation is greater than or equal to 0.41 and less than 1.65. In some embodiments, the formulation is for intravenous administration.

In some embodiments, the monoclonal antibody in the formulation described herein is in an amount of about 30 mg/mL to about 90 mg/mL, about 35 mg/mL to about 85 mg/mL, about 35 mg/mL to 75 mg/mL, about 40 mg/mL to about 80 mg/mL, about 45 mg/mL to about 70 mg/mL, or about 45 mg/mL to about 55 mg/mL. In some embodiments, the monoclonal antibody in the formulation is about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL, including every value in between these numbers. In some embodiments, the monoclonal antibody in the formulation is about 45 mg/mL, about 50 mg/mL, or about 55 mg/mL.

In some embodiments, the formulation described herein comprises the trehalose in about 45 mM to about 600 mM, about 45 mM to about 550 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 150 mM, about 45 mM to about 140 mM, about 45 mM to about 135 mM, about 45 mM to about 130 mM, about 45 mM to about 120 mM, about 45 mM to about 110 mM, about 45 mM to about 100 mM, about 180 mM to about 634 mM, about 50 mM to about 600 mM, or about 150 mM to about 400 mM. In some embodiments, the trehalose in the formulation is about 45 mM, about 50 mM, about 60 mM, about 70 mM, about 80 mM, about 90 mM, about 100 mM, about 110 mM, about 120 mM, about 130 mM, about 135 mM, about 140 mM, about 150 mM, about 180 mM, about 200 mM, about 250 mM, about 300 mM, about 350 mM, about 400 mM, about 450 mM, about 500 mM, about 550 mM, about 600 mM, about 610 mM, about 620 mM, about 630 mM, or about 634 mM, including every value in between these numbers. In some embodiments, the formulation comprises phosphate (e.g., sodium phosphate) as a buffer. In some embodiments, the phosphate buffer (e.g., sodium phosphate) in the formulation is about 15 mM to about 30 mM, about 20 mM to 30 mM, about 22 mM to about 28 mM, greater than 35 mM to about 100 mM, about 40 mM to about 100 mM, about 45 mM to about 90 mM, about 50 mM to about 75 mM, or about 15 mM to about 100 mM. In some embodiments, the phosphate (e.g., sodium phosphate) in the formulation is about 15 mM, about 20 mM, about 22 mM, about 25 mM, about 28 mM, about 30 mM, about 35 mM, about 36 mM, about 40 mM, about 45 mM, about 50 mM, about 51 mM, about 55 mM, about 60 mM, about 65 mM, about 70 mM, about 75 mM, about 80 mM, about 85 mM, about 90 mM, about 95 mM, or about 100 mM, including every value in between these numbers. In some embodiments, the formulation comprises histidine (such as L-histidine) as a buffer. In some embodiments, the histidine in the formulation is about 15 mM to about 30 mM, about 20 mM to 30 mM, about 22 mM to about 28 mM, greater than 35 mM to about 100 mM, about 40 mM to about 100 mM, about 45 mM to about 90 mM, about 50 mM to about 75 mM, or about 15 mM to about 100 mM. In some embodiments, the histidine in the formulation is about 15 mM, about 20 mM, about 22 mM, about 25 mM, about 28 mM, about 30 mM, about 35 mM, about 36 mM, about 40 mM, about 45 mM, about 50 mM, about 51 mM, about 55 mM, about 60 mM, about 65 mM, about 70 mM, about 75 mM, about 80 mM, about 85 mM, about 90 mM, about 95 mM, or about 100 mM, including every value in between these numbers.

In some embodiments, the formulation described herein further comprises a surfactant. In some embodiments, surfactant is polysorbate (such as polysorbate 20) or poloxamer (such as poloxamer 188). In some embodiments, surfactant concentration is about 0.01% to about 0.1%, about 0.01% to about 0.05%, or about 0.02% to about 0.04%. In some embodiments, the surfactant concentration is about 0.01%, about 0.02%, about 0.03%, about 0.04%, about 0.05%, or about 0.1%, including every value in between these numbers.

In some embodiments, the formulation described herein has a pH about 5.5 to about 6.5, about 5.8 to about 6.8, about 5.9 to about 6.5, about 6.0 to about 6.5, about 6.0 to about 6.4, or about 6.0 to about 6.2. In some embodiments, the formulation has a pH about 5.6, about 5.8, about 5.9, about 6.0, about 6.2, about 6.4, about 6.5, about 6.8, or about 7.0, including every value in between these numbers.

In some embodiments, the monoclonal antibody in the formulation described herein is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds VEGF. In some embodiments, the antibody is bevacizumab. In some embodiments, the monoclonal antibody is susceptible to aggregation.

In some embodiments, the monoclonal antibody in the formulation described herein is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds CD20. In some embodiments, the antibody that binds CD20 is a humanized B-Ly1 antibody described herein. In some embodiments, the antibody that binds CD20 is an antibody comprising a heavy chain variable region amino acid sequence selected from SEQ ID NO:3 to SEQ ID NO:19 and a light chain variable region amino acid sequence of SEQ ID NO:20. In some embodiments, the antibody is obinutuzumab. In some embodiments, the monoclonal antibody is susceptible to aggregation.

In some embodiments, the formulation described herein is stable at −20° C. for at least about 6 months, at least about 12 months, at least about 15 months, at least about 18 months, at least about 19 months, at least about 20 months, or at least about 2 years. In some embodiments, the formulation is sterile. In some embodiments, the formulation is for administration to a subject. In some embodiments, the formulation is for intravenous (IV), subcutaneous (SQ), intraocular (IO), or intramuscular (IM) administration.

In another aspect, the invention provides articles of manufacture comprising a container holding a stable aqueous pharmaceutical formulation described herein. In some embodiments, the formulation comprises a monoclonal antibody, trehalose, and a buffer, wherein the weight ratio of said monoclonal antibody to said trehalose in the formulation is greater than or equal to 0.41 and less than 1.65, and wherein the formulation has a pH of about 5.5 to about 7.0. In some embodiments, the formulation comprises (a) a monoclonal antibody in an amount of about 25 to about 100 mg/mL; (b) trehalose in an amount of about 45 mM to about 634 mM; and (c) sodium phosphate in an amount of greater than 35 mM to about 100 mM, wherein said formulation has a pH of about 5.5 to about 7.0, wherein the weight ratio of said monoclonal antibody to said trehalose in the formulation is greater than or equal to 0.41 and less than 1.6, and an optional surfactant. In some embodiments, the weight ratio of the monoclonal antibody to the trehalose in the formulation is 0.41 to 0.73. In some embodiments, the weight ratio of the monoclonal antibody to the trehalose is 0.73 to 1.47. In some embodiments, the weight ratio of the monoclonal antibody to the trehalose is 0.49 to 1.47. In some embodiments, the weight ratio of the monoclonal antibody to the trehalose in the formulation is any of 0.41, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, and 1.64, including every value in between these numbers.

In some embodiments, the monoclonal antibody in the formulation is in an amount of about 30 mg/mL to about 90 mg/mL, about 35 mg/mL to about 85 mg/mL, about 35 mg/mL to about 75 mg/mL, about 40 mg/mL to about 80 mg/mL, about 45 mg/mL to about 70 mg/mL, or about 45 mg/mL to about 55 mg/mL. In some embodiments, the monoclonal antibody in the formulation is about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL, including every value in between these numbers. In some embodiments, the monoclonal antibody in the formulation is about 45 mg/mL, about 50 mg/mL, or about 55 mg/mL.

In some embodiments, the formulation comprises the trehalose in about 45 mM to about 600 mM, about 45 mM to about 550 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 150 mM, about 45 mM to about 140 mM, about 45 mM to about 135 mM, about 45 mM to about 130 mM, about 45 mM to about 120 mM, about 45 mM to about 110 mM, about 45 mM to about 100 mM, about 180 mM to about 634 mM, about 50 mM to about 600 mM, or about 150 mM to about 400 mM. In some embodiments, the trehalose in the formulation is about 45 mM, about 50 mM, about 60 mM, about 70 mM, about 80 mM, about 90 mM, about 100 mM, about 110 mM, about 120 mM, about 130 mM, about 135 mM, about 140 mM, about 150 mM, about 180 mM, about 200 mM, about 250 mM, about 300 mM, about 350 mM, about 400 mM, about 450 mM, about 500 mM, about 550 mM, about 600 mM, about 610 mM, about 620 mM, about 630 mM, or about 634 mM, including every value in between these numbers. In some embodiments, the formulation comprises sodium phosphate as a buffer. In some embodiments, the sodium phosphate in the formulation is about 15 mM to about 30 mM, about 20 mM to 30 mM, about 22 mM to about 28 mM, greater than 35 mM to about 100 mM, about 40 mM to about 100 mM, about 45 mM to about 90 mM, about 50 mM to about 75 mM, or about 15 mM to about 100 mM. In some embodiments, the sodium phosphate in the formulation is about 15 mM, about 20 mM, about 22 mM, about 25 mM, about 28 mM, about 30 mM, about 35 mM, about 36 mM, about 40 mM, about 45 mM, about 50 mM, about 51 mM, about 55 mM, about 60 mM, about 65 mM, about 70 mM, about 75 mM, about 80 mM, about 85 mM, about 90 mM, about 95 mM, or about 100 mM, including every value in between these numbers. In some embodiments, the formulation comprises histidine (such as L-histidine) as a buffer. In some embodiments, the histidine in the formulation is about 15 mM to about 30 mM, about 20 mM to 30 mM, about 22 mM to about 28 mM, greater than 35 mM to about 100 mM, about 40 mM to about 100 mM, about 45 mM to about 90 mM, about 50 mM to about 75 mM, or about 15 mM to about 100 mM. In some embodiments, the histidine in the formulation is about 15 mM, about 20 mM, about 22 mM, about 25 mM, about 28 mM, about 30 mM, about 35 mM, about 36 mM, about 40 mM, about 45 mM, about 50 mM, about 51 mM, about 55 mM, about 60 mM, about 65 mM, about 70 mM, about 75 mM, about 80 mM, about 85 mM, about 90 mM, about 95 mM, or about 100 mM, including every value in between these numbers.

In some embodiments, the formulation further comprises a surfactant. In some embodiments, surfactant is polysorbate (such as polysorbate 20) or poloxamer (such as poloxamer 188). In some embodiments, the surfactant concentration is about 0.01% to about 0.1%, about 0.01% to about 0.05%, or about 0.02% to about 0.04%. In some embodiments, the surfactant concentration is about 0.01%, about 0.02%, about 0.03%, about 0.04%, about 0.05%, or about 0.1%, including every value in between these numbers.

In some embodiments, the formulation has a pH about 5.5 to about 6.5, about 5.8 to about 6.8, about 5.9 to about 6.5, about 6.0 to about 6.5, about 6.0 to about 6.4, or about 6.0 to about 6.2. In some embodiments, the formulation has a pH about 5.6, about 5.8, about 5.9, about 6.0, about 6.2, about 6.4, about 6.5, about 6.8, or about 7.0, including every value in between these numbers.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds VEGF. In some embodiments, the antibody is bevacizumab. In some embodiments, the monoclonal antibody is susceptible to aggregation.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds CD20. In some embodiments, the antibody that binds CD20 is a humanized B-Ly1 antibody described herein. In some embodiments, the antibody that binds CD20 is an antibody comprising a heavy chain variable region amino acid sequence selected from SEQ ID NO:3 to SEQ ID NO:19 and a light chain variable region amino acid sequence of SEQ ID NO:20. In some embodiments, the antibody is obinutuzumab. In some embodiments, the monoclonal antibody is susceptible to aggregation.

In some embodiments, the formulation is stable at −20° C. for at least about 6 months, at least about 12 months, at least about 15 months, at least about 18 months, at least about 19 months, at least about 20 months, or at least about 2 years. In some embodiments, the formulation is sterile. In some embodiments, the formulation is for administration to a subject. In some embodiments, the formulation is for intravenous (IV), subcutaneous (SQ), intraocular (IO), or intramuscular (IM) administration.

In some embodiments, the container is a vial with a stopper pierceable by a syringe, wherein the vial comprises any one of the formulations described herein. In some embodiments, the vial is stored at about 2-8° C. In some embodiments, the vial is stored at about −20° C. In some embodiments, the vial is a 3 cc, 20 cc or 50 cc vial.

In another aspect, the invention provides stainless steel tanks comprising any one of the formulations described herein inside the tank. In some embodiments, the formulation is frozen.

In another aspect, the invention provides methods of reducing aggregation of a therapeutic monoclonal antibody. In some embodiments, the method comprises formulating the monoclonal antibody in a formulation comprising trehalose and a buffer, wherein the weight ratio of the monoclonal antibody to the trehalose in the formulation is greater than or equal to 0.41 and less than 1.65, and wherein the formulation has a pH of about 5.5 to about 7.0. In some embodiments, the method comprises formulating the antibody in a formulation comprising trehalose in an amount of about 45 mM to about 634 mM, about 50 mM to about 600 mM, or about 150 mM to about 400 mM and sodium phosphate in an amount of greater than 35 mM to about 100 mM, and said formulation having a pH of about 5.5 to about 7.0, wherein said monoclonal antibody is formulated in an amount of about 25 mg/mL to about 100 mg/mL in the formulation, and wherein the weight ratio of said monoclonal antibody to said trehalose in the formulation is greater than or equal to 0.41 and less than 1.65.

In some embodiments of the method described herein, the weight ratio of said monoclonal antibody to said trehalose in the formulation is greater than or equal to 0.41 and less than 1.65. In some embodiments of the methods described herein, the weight ratio of the monoclonal antibody to the trehalose is 0.73 to 1.47. In some embodiments, the weight ratio of the monoclonal antibody to the trehalose is 0.49 to 1.47. In some embodiments, the weight ratio of the monoclonal antibody to the trehalose is any of 0.41, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, and 1.64, including every value in between these numbers.

In some embodiments, the monoclonal antibody in the formulation is in an amount of about 30 mg/mL to about 90 mg/mL, about 35 mg/mL to about 85 mg/mL, about 35 mg/mL to about 75 mg/mL, about 40 mg/mL to about 80 mg/mL, about 45 mg/mL to about 70 mg/mL, or about 45 mg/mL to about 55 mg/mL. In some embodiments, the monoclonal antibody in the formulation is about 25 mg/mL, about 30 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL, including every value in between these numbers. In some embodiments, the monoclonal antibody in the formulation is about 45 mg/mL, about 50 mg/mL, or about 55 mg/mL.

In some embodiments, the formulation comprises the trehalose in about 45 mM to about 600 mM, about 45 mM to about 550 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 150 mM, about 45 mM to about 140 mM, about 45 mM to about 135 mM, about 45 mM to about 130 mM, about 45 mM to about 120 mM, about 45 mM to about 110 mM, about 45 mM to about 100 mM, about 180 mM to about 634 mM, about 50 mM to about 600 mM, or about 150 mM to about 400 mM. In some embodiments, the trehalose in the formulation is about 45 mM, about 50 mM, about 60 mM, about 70 mM, about 80 mM, about 90 mM, about 100 mM, about 110 mM, about 120 mM, about 130 mM, about 135 mM, about 140 mM, about 150 mM, about 180 mM, about 200 mM, about 250 mM, about 300 mM, about 350 mM, about 400 mM, about 450 mM, about 500 mM, about 550 mM, about 600 mM, about 610 mM, about 620 mM, about 630 mM, or about 634 mM. In some embodiments, the formulation comprises sodium phosphate as a buffer. In some embodiments, the sodium phosphate in the formulation is about 15 mM to about 30 mM, about 20 mM to 30 mM, about 22 mM to about 28 mM, greater than 35 mM to about 100 mM, about 40 mM to about 100 mM, about 45 mM to about 90 mM, about 50 mM to about 75 mM, or about 15 mM to about 100 mM. In some embodiments, the sodium phosphate in the formulation is about 15 mM, about 20 mM, about 22 mM, about 25 mM, about 28 mM, about 30 mM, about 35 mM, about 36 mM, about 40 mM, about 45 mM, about 50 mM, about 51 mM, about 55 mM, about 60 mM, about 65 mM, about 70 mM, about 75 mM, about 80 mM, about 85 mM, about 90 mM, about 95 mM, or about 100 mM, including every value in between these numbers. In some embodiments, the formulation comprises histidine (such as L-histidine) as a buffer. In some embodiments, the histidine in the formulation is about 15 mM to about 30 mM, about 20 mM to 30 mM, about 22 mM to about 28 mM, greater than 35 mM to about 100 mM, about 40 mM to about 100 mM, about 45 mM to about 90 mM, about 50 mM to about 75 mM, or about 15 mM to about 100 mM. In some embodiments, the histidine in the formulation is about 15 mM, about 20 mM, about 22 mM, about 25 mM, about 28 mM, about 30 mM, about 35 mM, about 36 mM, about 40 mM, about 45 mM, about 50 mM, about 51 mM, about 55 mM, about 60 mM, about 65 mM, about 70 mM, about 75 mM, about 80 mM, about 85 mM, about 90 mM, about 95 mM, or about 100 mM, including every value in between these numbers.

In some embodiments, the formulation further comprises a surfactant. In some embodiments, surfactant is polysorbate (such as polysorbate 20) or poloxamer (such as poloxamer 188). In some embodiments, surfactant concentration is about 0.01% to about 0.1%, about 0.01% to about 0.05%, or about 0.02% to about 0.04%. In some embodiments, the surfactant concentration is about 0.01%, about 0.02%, about 0.03%, about 0.04%, about 0.05%, or about 0.1%, including every value in between these numbers.

In some embodiments, the formulation has a pH about 5.5 to about 6.5, about 5.8 to about 6.8, about 5.9 to about 6.5, about 6.0 to about 6.5, about 6.0 to about 6.4, or about 6.0 to about 6.2. In some embodiments, the formulation has a pH about 5.6, about 5.8, about 5.9, about 6.0, about 6.2, about 6.4, about 6.5, about 6.8, or about 7.0, including every value in between these numbers.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds VEGF. In some embodiments, the antibody is bevacizumab. In some embodiments, the monoclonal antibody is susceptible to aggregation.

In some embodiments, the monoclonal antibody is not subject to prior lyophilization. In some embodiments, the monoclonal antibody is a full length antibody. In some embodiments, the monoclonal antibody is an IgG1, IgG2, or IgG4 antibody. In some embodiments, the monoclonal antibody is a humanized antibody, a chimeric antibody or a human antibody. In some embodiments, the monoclonal antibody is an antibody fragment comprising an antigen-binding region. In some embodiments, the antibody fragment is a Fab or F(ab')$_2$ fragment. In some embodiments, the monoclonal antibody binds CD20. In some embodiments, the antibody that binds CD20 is a humanized B-Ly1 antibody described herein. In some embodiments, the antibody that binds CD20 is an antibody comprising a heavy chain variable region amino acid sequence selected from SEQ ID NO:3 to SEQ ID NO:19 and a light chain variable region amino acid sequence of SEQ ID NO:20. In some embodiments, the antibody is obinutuzumab. In some embodiments, the monoclonal antibody is susceptible to aggregation.

In some embodiments, the formulation is stable at −20° C. for at least about 6 months, at least about 12 months, at least about 15 months, at least about 18 months, at least about 19 months, at least about 20 months, or at least about 2 years. In some embodiments, the formulation is sterile. In some embodiments, the formulation is for administration to a subject. In some embodiments, the formulation is for intravenous (IV), subcutaneous (SQ), intraocular (IO), or intramuscular (IM) administration.

In another aspect, the invention provides methods of making a pharmaceutical formulation comprising: (a) preparing any one of the formulations described herein; and (b) evaluating physical stability, chemical stability, or biological activity of the antibody in the formulation. In some embodiments, the physical stability, chemical stability, or biological activity of the antibody in the formulation is evaluated at about 6 months, about 12 months, about 18 months, or about 24 months after the formulation is stored (e.g., at −20° C. or −40° C.).

In another aspect, the invention provides methods of treating a disease or disorder in a subject comprising administering any one of the formulations described herein to a subject in an amount effective to treat the disease or disorder. In some embodiments, the formulation comprises an antibody that binds to VEGF. In some embodiments, the antibody is bevacizumab. In some embodiments, the disease is cancer. In some embodiments, the cancer is selected from colorectal cancer, lung cancer, breast cancer, renal cancer, and glioblastoma.

In another aspect, the invention provides methods of treating a disease or disorder in a subject comprising administering any one of the formulations described herein to a subject in an amount effective to treat the disease or disorder. In some embodiments, the formulation comprises an antibody that binds to CD20. In some embodiments, the antibody is obinutuzumab. In some embodiments, the disease is cancer. In some embodiments, the cancer is a CD20 expression cancer, for example, lymphoma, lymphocytic leukemia, and multiple myeloma.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIGS. 1A, 1B, 1C and 1D show visual trehalose crystallization after induced nucleation on the surface of frozen samples with pharmaceutically relevant concentrations of trehalose of (FIG. 1A) 0.0% (wt/v) trehalose, (FIG. 1B) 2.0% (wt/v) trehalose, (FIG. 1C) 4.0% (wt/v) trehalose, and (FIG. 1D) 8.0% (wt/v) trehalose.

FIGS. 3A, 3B and 3C show the time dependent increase in aggregation of mAb1 (FIG. 3A), bevacizumab (FIG. 3B), and mAb3 (FIG. 3C) fast freeze samples stored frozen at −20° C. (1), −14° C. (2), and −8° C. (3), as labeled.

(FIG. 4A) Effect of Freeze Rate. mAb3 samples frozen at the slow (1), normal (2), and fast (3) freeze rates (as labeled) and stored at −20° C. for 12 months. Study control (stored at −70° C.) shown for comparison. (FIG. 4B) Effect of Storage Temperature. mAb3 samples frozen at the fast freeze rate and stored at −20° C. (3), −14° C. (2), and −8° C. (1) for 12 months, as labeled. Study control (stored at −70° C.) shown for comparison.

FIGS. 6A1-FIG. 6C3 show normalized NIR spectra of the (FIGS. 6A1, 6A2 and 6A3) mAb1, (FIGS. 6B1, 6B2, and 6B3) bevacizumab, and (FIGS. 6C1, 6C2, and 6C3) mAb3 samples frozen using (FIGS. 6A1, 6B1, and 6C1) slow freezing, (FIGS. 6A2, 6B2, and 6C2) normal freezing, and (3) fast freezing rates following 12 months storage at −20° C., −14° C., and −8° C.

FIGS. 7A, 7B and 7C show the concentrations of amorphous (1) and crystallized trehalose (2) in formulations with (FIG. 7A) 0 mg/mL bevacizumab, (FIG. 7B) 25 mg/mL bevacizumab, and (FIG. 7C) 100 mg/mL bevacizumab following 12 months storage at −20° C.

DETAILED DESCRIPTION

I. Definitions

Figure 2A:
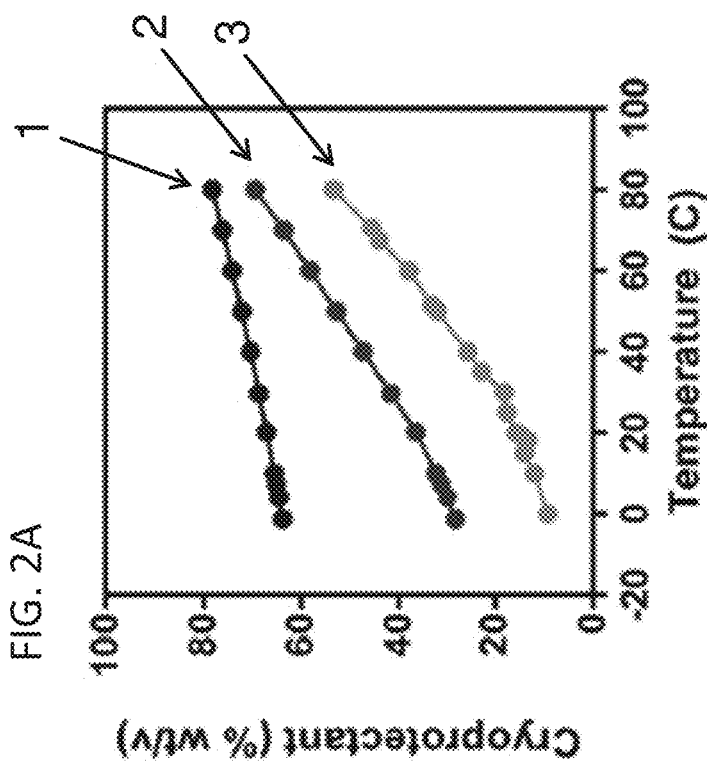
FIG. 2A shows the solubility of sucrose (1), trehalose (2), and mannitol (3) as a function of temperature, as labeled.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores.

A "frozen" formulation is one at a temperature below 0° C. Generally, the frozen formulation is not freeze-dried, nor is it subjected to prior, or subsequent, lyophilization. In certain embodiments, the frozen formulation comprises frozen drug substance for storage (in stainless steel tank) or frozen drug product (in final vial configuration).

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected temperature for a selected time period. In certain embodiments, the formulation is stable at about 40° C. for at least about 1, 2, 3, 4, 5, 6, 7, 14, 21, 28, or more days. In certain embodiments, the formulation is stable at about 40° C. for at least about 1, 2, 3, 4, 5, 6, 7, 8, or more weeks. In certain embodiments, the formulation is stable at about 25° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the formulation is stable at about 5° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the formulation is stable at about −20° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, the formulation is stable at 5° C. or −20° C. for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. Furthermore, the formulation is preferably stable following freezing (to, e.g., −20° C., −40° C. or −70° C.) and thawing of the formulation, for example following 1, 2 3, 4, or 5 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc.

A protein "retains its physical stability" in a pharmaceutical formulation if it shows no signs or very little of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography or icIEF, for example.

An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

As used herein, "biological activity" of a monoclonal antibody refers to the ability of the antibody to bind to antigen. It can further include antibody binding to antigen and resulting in a measurable biological response which can be measured in vitro or in vivo. Such activity may be antagonistic or agonistic.

A "deamidated" monoclonal antibody herein is one in which one or more asparagine residue thereof has been derivitized, e.g. to an aspartic acid or an iso-aspartic acid.

An antibody which is "susceptible to deamidation" is one comprising one or more residue, which has been found to be prone to deamidate.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, aggregation, or fragmentation" is intended preventing or decreasing the amount of deamidation, aggregation, or fragmentation relative to the monoclonal antibody formulated in a different formulation.

The antibody which is formulated is preferably essentially pure and desirably essentially homogeneous (e.g., free from contaminating proteins etc.). "Essentially pure" antibody means a composition comprising at least about 90% by weight of the antibody, based on total weight of the composition, preferably at least about 95% by weight. "Essentially homogeneous" antibody means a composition comprising at least about 99% by weight of antibody, based on total weight of the composition.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example. In some embodiments, the formulation has an osmolality of greater than about 240 mOsm/kg.

As used herein, "buffer" refers to a buffered solution that resists changes in pH by the action of its acid-base conjugate components. The buffer of this invention preferably has a pH in the range from about 4.5 to about 7.0, preferably from about 5.6 to about 7.0, for example from 5.6 to 6.9, 5.7 to 6.8, 5.8 to 6.7, 5.9 to 6.6, 5.9 to 6.5, 6.0, 6.0 to 6.4, or 6.1 to 6.3. In one embodiment the buffer has a pH 5.6, 5.7, 5.8, 5.9, 6.0, 6.1, 6.2, 6.3, 6.4, 6.5, 6.6, 6.7, 6.8, 6.9, or 7.0. For example, sodium phosphate is an example of buffers that will control the pH in this range.

As used herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. In one embodiment, the surfactant herein is polysorbate 20.

In a pharmacological sense, in the context of the invention, a "therapeutically effective amount" of an antibody refers to an amount effective in the prevention or treatment of a disorder for the treatment of which the antibody is effective. A "disorder" is any condition that would benefit from treatment with the antibody. This includes chronic and acute disorders or diseases including those pathological conditions which predispose the mammal to the disorder in question.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) *Science* 246:1306, and Houck et al. (1991) *Mol. Endocrin* 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

"VEGF biological activity" includes binding to any VEGF receptor or any VEGF signaling activity such as regulation of both normal and abnormal angiogenesis and vasculogenesis (Ferrara and Davis-Smyth (1997) *Endocrine Rev.* 18:4-25; Ferrara (1999) *J. Mol. Med.* 77:527-543); promoting embryonic vasculogenesis and angiogenesis (Carmeliet et al. (1996) *Nature* 380:435-439; Ferrara et al. (1996) *Nature* 380:439-442); and modulating the cyclical blood vessel proliferation in the female reproductive tract and for bone growth and cartilage formation (Ferrara et al. (1998) *Nature Med.* 4:336-340; Gerber et al. (1999) *Nature Med.* 5:623-628). In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx (Ferrara and Davis-Smyth (1997), supra and Cebe-Suarez et al. *Cell. Mol. Life Sci.* 63:601-615 (2006)). Moreover, recent studies have reported mitogenic effects of VEGF on a few non-endothelial cell types, such as retinal pigment epithelial cells, pancreatic duct cells, and Schwann cells. Guerrin et al. (1995) *J Cell Physiol.* 164: 385-394; Oberg-Welsh et al. (1997) *Mol. Cell. Endocrinol.* 126:125-132; Sondell et al. (1999) *J. Neurosci.* 19:5731-5740.

A "VEGF antagonist" or "VEGF-specific antagonist" refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors and VEGF mediated angiogenesis and endothelial cell survival or proliferation. Included as VEGF-specific antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and $VEGF_{121}$-gelonin (Peregrine). VEGF-specific antagonists also include antagonist variants of VEGF polypeptides, antisense nucleobase oligomers directed to VEGF, small RNA molecules directed to VEGF, RNA aptamers, peptibodies, and ribozymes against VEGF. VEGF-specific antagonists also include nonpeptide small molecules that bind to VEGF and are capable of blocking, inhibiting, abrogating, reducing, or interfering with VEGF biological activities. Thus, the term "VEGF activities" specifically includes VEGF mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF.

An "anti-VEGF antibody" is an antibody that binds to VEGF with sufficient affinity and specificity. In certain embodiments, the antibody selected will normally have a sufficiently binding affinity for VEGF, for example, the antibody may bind hVEGF with a $K_d$ value of between 100 $nM^{-1}$ pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example.

In certain embodiment, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as P1GF, PDGF or bFGF. In one embodiment, anti-VEGF antibody is a monoclonal antibody that binds to the same epitope as the monoclonal anti-VEGF antibody A4.6.1 produced by hybridoma ATCC HB 10709. In another embodiment, the anti-VEGF antibody is a recombinant humanized anti-VEGF monoclonal antibody generated according to Presta et al. (1997) Cancer Res. 57:4593-4599, including but not limited to the antibody known as bevacizumab (BV; AVASTIN®).

The anti-VEGF antibody "Bevacizumab (BV)," also known as "rhuMAb VEGF" or AVASTIN®, is a recombinant humanized anti-VEGF monoclonal antibody generated according to Presta et al. (1997) Cancer Res. 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 Daltons and is glycosylated. Bevacizumab and other humanized anti-VEGF antibodies are further described in U.S. Pat. No. 6,884,879 issued Feb. 26, 2005, the entire disclosure of which is expressly incorporated herein by reference.

The term "B20 series polypeptide" as used herein refers to a polypeptide, including an antibody that binds to VEGF. B20 series polypeptides includes, but not limited to, antibodies derived from a sequence of the B20 antibody or a B20-derived antibody described in US Publication No. 20060280747, US Publication No. 20070141065 and/or US Publication No. 20070020267, the content of these patent applications are expressly incorporated herein by reference. In one embodiment, B20 series polypeptide is B20-4.1 as described in US Publication No. 20060280747, US Publication No. 20070141065 and/or US Publication No. 20070020267. In another embodiment, B20 series polypeptide is B20-4.1.1 described in U.S. Pat. No. 7,910,098, the entire disclosure of which is expressly incorporated herein by reference.

The term "G6 series polypeptide" as used herein refers to a polypeptide, including an antibody that binds to VEGF. G6 series polypeptides includes, but not limited to, antibodies derived from a sequence of the G6 antibody or a G6-derived antibody described in US Publication No. 20060280747, US Publication No. 20070141065 and/or US Publication No. 20070020267. G6 series polypeptides, as described in US Publication No. 20060280747, US Publication No. 20070141065 and/or US Publication No. 20070020267 include, but not limited to, G6-8, G6-23 and G6-31.

For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). In certain embodiments, other antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183 and Q89.

Other anti-VEGF antibodies are also known, and described, for example, in Liang et al., J Biol Chem 281, 951-961 (2006).

"CD20" as used herein refers to the human B-lymphocyte antigen CD20 (also known as CD20, B-lymphocyte surface antigen B1, Leu-16, Bp35, BM5, and LF5; the sequence is characterized by the SwissProt database entry P11836) is a hydrophobic transmembrane protein with a molecular weight of approximately 35 kD located on pre-B and mature B lymphocytes. (Valentine, M. A., et al., J. Biol. Chem. 264(19) (1989 11282-11287; Tedder, T. F., et al, Proc. Natl. Acad. Sci. U.S.A. 85 (1988) 208-12; Stamenkovic, I., et al., J. Exp. Med. 167 (1988) 1975-80; Einfeld, D. A., et al., EMBO J. 7 (1988) 711-7; Tedder, T. F., et al., J. Immunol. 142 (1989) 2560-8). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein.

The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 (e.g., a tumor cell) by inactivating CD20. The killing of the cells expressing CD20 may occur by one or more of the following mechanisms: Cell death/apoptosis induction, ADCC and CDC.

Synonyms of CD20, as recognized in the art, include B-lymphocyte antigen CD20, B-lymphocyte surface antigen B1, Leu-16, Bp35, BM5, and LF5.

The term "anti-CD20 antibody" according to the invention is an antibody that binds specifically to CD20 antigen. Depending on binding properties and biological activities of anti-CD20 antibodies to the CD20 antigen, two types of anti-CD20 antibodies (type I and type II anti-CD20 antibodies) can be distinguished according to Cragg, M. S., et al., *Blood* 103 (2004) 2738-2743; and Cragg, M. S., et al., *Blood* 101 (2003) 1045-1052, see Table 1.

TABLE 1

Properties of type I and type II anti-CD20 antibodies

| Type I anti-CD20 antibodies | type II anti-CD20 antibodies |
|---|---|
| type I CD20 epitope | type II CD20 epitope |
| Localize CD20 to lipid rafts | Do not localize CD20 to lipid rafts |
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |
| Apoptosis induction upong cross-linkin | Strong cell death induction without cross-linking |

Examples of type II anti-CD20 antibodies include e.g. humanized B-Ly1 antibody IgG1 (a chimeric humanized IgG1 antibody as disclosed in WO 2005/044859), 11B8 IgG1 (as disclosed in WO 2004/035607), and AT80 IgG1. Typically type II anti-CD20 antibodies of the IgG1 isotype show characteristic CDC properties. Type II anti-CD20 antibodies have a decreased CDC (if IgG1 isotype) compared to type I antibodies of the IgG1 isotype.

Examples of type I anti-CD20 antibodies include e.g. rituximab, HI47 IgG3 (ECACC, hybridoma), 2C6 IgG1 (as disclosed in WO 2005/103081), 2F2 IgG1 (as disclosed and WO 2004/035607 and WO 2005/103081) and 2H7 IgG1 (as disclosed in WO 2004/056312).

The afucosylated anti-CD20 antibodies according to the invention is preferably a type II anti-CD20 antibodies, more preferably an afucosylated humanized B-Ly1 antibody as described in WO 2005/044859 and WO 2007/031875.

The "rituximab" antibody (reference antibody; example of a type I anti-CD20 antibody) is a genetically engineered chimeric human gamma 1 murine constant domain containing monoclonal antibody directed against the human CD20 antigen. However this antibody is not glycoengineered and not afucosylates and thus has an amount of fucose of at least 85%. This chimeric antibody contains human gamma 1 constant domains and is identified by the name "C2B8" in U.S. Pat. No. 5,736,137 (Andersen, et. al.) issued on Apr. 17, 1998, assigned to IDEC Pharmaceuticals Corporation. Rituximab is approved for the treatment of patients with relapsed or refracting low-grade or follicular, CD20 positive, B cell non-Hodgkin's lymphoma. In vitro mechanism of action studies have shown that rituximab exhibits human complement-dependent cytotoxicity (CDC) (Reff, M. E., et. al, *Blood* 83(2) (1994) 435-445). Additionally, it exhibits activity in assays that measure antibody-dependent cellular cytotoxicity (ADCC).

The term "humanized B-Ly1 antibody" refers to humanized B-Ly1 antibody as disclosed in WO 2005/044859 and WO 2007/031875, which were obtained from the murine monoclonal anti-CD20 antibody B-Ly1 (variable region of the murine heavy chain (VH): SEQ ID NO: 1; variable region of the murine light chain (VL): SEQ ID NO: 2—see Poppema, S. and Visser, L., *Biotest Bulletin* 3 (1987) 131-139) by chimerization with a human constant domain from IgG1 and following humanization (see WO 2005/044859 and WO 2007/031875). These "humanized B-Ly1 antibodies" are disclosed in detail in WO 2005/044859 and WO 2007/031875.

In one embodiment, the "humanized B-Ly1 antibody" has variable region of the heavy chain (VH) selected from group of SEQ ID No. 3 to SEQ ID No. 19 (B-HH2 to B-HH9 and B-HL8 to B-HL17 of WO 2005/044859 and WO 2007/031875). In one specific embodiment, such variable domain is selected from the group consisting of SEQ ID No. 3, 4, 7, 9, 11, 13 and 15 (B-HH2, BHH-3, B-HH6, B-HH8, B-HL8, B-HL11 and B-HL13 of WO 2005/044859 and WO 2007/031875). In one specific embodiment, the "humanized B-Ly1 antibody" has variable region of the light chain (VL) of SEQ ID No. 20 (B-KV1 of WO 2005/044859 and WO 2007/031875). In one specific embodiment, the "humanized B-Ly1 antibody" has a variable region of the heavy chain (VH) of SEQ ID No. 7 (B-HH6 of WO 2005/044859 and WO 2007/031875) and a variable region of the light chain (VL) of SEQ ID No. 20 (B-KV1 of WO 2005/044859 and WO 2007/031875). Furthermore in one embodiment, the humanized B-Ly1 antibody is an IgG1 antibody. According to the invention such afocusylated humanized B-Ly1 antibodies are glycoengineered (GE) in the Fc region according to the procedures described in WO 2005/044859, WO 2004/065540, WO 2007/031875, Umana, P. et al., Nature Biotechnol. 17 (1999) 176-180 and WO 99/154342. In one embodiment, the afucosylated glyco-engineered humanized B-Ly1 is B-HH6-B-KV1 GE. In one embodiment, the anti-CD20 antibody is obinutuzumab (recommended INN, WHO Drug Information, Vol. 26, No. 4, 2012, p. 453). As used herein, obinutuzumab is synonymous for GA101 or RO5072759. This replaces all previous versions (e.g. Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In some embodiments, the humanized B-Ly1 antibody is an antibody comprising a heavy chain comprising the amino acid sequence of SEQ ID NO:21 and a light chain comprising the amino acid sequence of SEQ ID NO:22 or an antigen-binding fragment thereof. In some embodiments, the humanized B-Ly1 antibody comprises a heavy chain variable region comprising the three heavy chain CDRs of SEQ ID NO:21 and a light chain variable region comprising the three light chain CDRs of SEQ ID NO:22.

```
Heavy chain
                                                      (SEQ ID NO: 21)
QVQLVQSGAE VKKPGSSVKV SCKASGYAFS YSWINWVRQA PGQGLEWMGR          50

IFPGDGDTDY NGKFKGRVTI TADKSTSTAY MELSSLRSED TAVYYCARNV         100

FDGYWLVYWG QGTLVTVSSA STKGPSVFPL APSSKSTSGG TAALGCLVKD         150

YFPEPVTVSW NSGALTSGVH TFPAVLQSSG LYSLSSVVTV PSSSLGTQTY         200

ICNVNHKPSN TKVDKKVEPK SCDKTHTCPP CPAPELLGGP SVFLFPPKPK         250

DTLMISRTPE VTCVVVDVSH EDPEVKFNWY VDGVEVHNAK TKPREEQYNS         300

TYRVVSVLTV LHQDWLNGKE YKCKVSNKAL PAPIEKTISK AKGQPREPQV         350

YTLPPSRDEL TKNQVSLTCL VKGFYPSDIA VEWESNGQPE NNYKTTPPVL         400

DSDGSFFLYS KLTVDKSRWQ QGNVFSCSVM HEALHNHYTQ KSLSLSPGK          449

Light chain
                                                      (SEQ ID NO: 22)
DIVMTQTPLS LPVTPGEPAS ISCRSSKSLL HSNGITYLYW YLQKPGQSPQ          50

LLIYQMSNLV SGVPDRFSGS GSGTDFTLKI SRVEAEDVGV YYCAQNLELP         100

YTFGGGTKVE IKRTVAAPSV FIFPPSDEQL KSGTASVVCL LNNFYPREAK         150

VQWKVDNALQ SGNSQESVTE QDSKDSTYSL SSTLTLSKAD YEKHKVYACE         200

VTHQGLSSPV TKSFNRGEC                                          219
```

In some embodiments, the humanized B-Ly1 antibody is an afucosylated glyco-engineered humanized B-Ly1. Such glycoengineered humanized B-Ly1 antibodies have an altered pattern of glycosylation in the Fc region, preferably having a reduced level of fucose residues. Preferably the amount of fucose is 60% or less of the total amount of oligosaccharides at Asn297 (in one embodiment the amount of fucose is between 40% and 60%, in another embodiment the amount of fucose is 50% or less, and in still another embodiment the amount of fucose is 30% or less). Furthermore the oligosaccharides of the Fc region are preferably bisected. These glycoengineered humanized B-Ly1 antibodies have an increased ADCC.

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins, N., et al., *Nature Biotechnol.* 14 (1996) 975-81).

Mammalian cells are the preferred hosts for production of therapeutic glycoproteins, due to their capability to glycosylate proteins in the most compatible form for human application. (Cumming, D. A., et al., *Glycobiology* 1 (1991) 115-30; Jenkins, N., et al., *Nature Biotechnol.* 14 (1996) 975-81). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum free media, and permit the development of safe and reproducible bioprocesses. Other commonly used animal cells include baby hamster kidney (BHK) cells, NSO- and SP2/0-mouse myeloma cells. More recently, production from transgenic animals has also been tested. (Jenkins, N., et al., *Nature Biotechnol.* 14 (1996) 975-981).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Morrison, S. L., *Trends Biotech.* 15 (1997) 26-32). The structure of the attached N-linked carbohydrate varies considerably, depending on the degree of processing, and can include high-mannose, multiply-branched as well as biantennary complex oligosaccharides. (Wright, A., and Morrison, S. L., *Trends Biotech.* 15 (1997) 26-32). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R., et al., *Glycobiology* 5(8) (1995) 813-22).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umana, P., et al., *Nature Biotechnol.* 17 (1999) 176-180 and U.S. Pat. No. 6,602,684. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., *Glycobiology* 5 (1995) 813-822; Jefferis, R., et al., *Immunol. Rev.* 163 (1998) 59-76; Wright, A., and Morrison, S. L., *Trends Biotechnol.* 15 (1997) 26-32).

It was previously shown that overexpression in Chinese hamster ovary (CHO) cells of B(1,4)-N-acetylglucosaminyl-transferase I11 ("GnTIII17y"), a glycosyltransferase catalyzing the formation of bisected oligosaccharides, significantly increases the in vitro ADCC activity of an antineuroblastoma chimeric monoclonal antibody (chCE7) produced by the engineered CHO cells. (See Umana, P., et al., *Nature Biotechnol.* 17 (1999) 176-180; and WO 99/154342, the entire contents of which are hereby incorporated by reference). The antibody chCE7 belongs to a large class of unconjugated monoclonal antibodies which have high tumor affinity and specificity, but have too little potency to be clinically useful when produced in standard industrial cell lines lacking the GnTIII enzyme (Umana, P., et al., *Nature Biotechnol.* 17 (1999) 176-180). That study was the first to show that large increases of ADCC activity could be obtained by engineering the antibody producing cells to express GnTIII, which also led to an increase in the proportion of constant region (Fc)-associated, bisected oligosaccharides, including bisected, non-fucosylated oligosaccharides, above the levels found in naturally-occurring antibodies.

"Treatment" refers to both therapeutic treatment and prophylactic or preventative measures. Those in need of treatment include those already with the disorder as well as those in which the disorder is to be prevented.

A "disorder" is any condition that would benefit from treatment including, but not limited to, chronic and acute disorders or diseases including those pathological conditions which predispose the mammal to the disorder in question. Disorders include angiogenic disorders. "Angiogenic disorder" as used herein refers to any condition involving abnormal angiogenesis or abnormal vascular permeability or leakage. Non-limiting examples of angiogenic disorders to be treated herein include malignant and benign tumors; non-leukemias and lymphoid malignancies; and, in particular, tumor (cancer) metastasis.

"Abnormal angiogenesis" occurs when new blood vessels grow either excessively or otherwise inappropriately (e.g., the location, timing, degree, or onset of the angiogenesis being undesired from a medical standpoint) in a diseased state or such that it causes a diseased state. In some cases, excessive, uncontrolled, or otherwise inappropriate angiogenesis occurs when there is new blood vessel growth that contributes to the worsening of the diseased state or cause of a diseased state. The new blood vessels can feed the diseased tissues, destroy normal tissues, and in the case of cancer, the new vessels can allow tumor cells to escape into the circulation and lodge in other organs (tumor metastases). Examples of disorders involving abnormal angiogenesis include, but are not limited to cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-related macular degeneration, choroidal neovascularization (CNV), diabetic macular edema, pathological myopia, von Hippel-Lindau disease, histoplasmosis of the eye, Central Retinal Vein Occlusion (CRVO), corneal neovascularization, retinal neovascularization and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various inflammatory diseases, such as arthritis, especially rheumatoid arthritis, inflammatory bowel disease, psoriasis, sarcoidosis, arterial arteriosclerosis and diseases occurring after transplants, endometriosis or chronic asthma and other conditions.

"Abnormal vascular permeability" occurs when the flow of fluids, molecules (e.g., ions and nutrients) and cells (e.g., lymphocytes) between the vascular and extravascular compartments is excessive or otherwise inappropriate (e.g., the location, timing, degree, or onset of the vascular permeability being undesired from a medical standpoint) in a diseased state or such that it causes a diseased state. Abnormal vascular permeability may lead to excessive or otherwise inappropriate "leakage" of ions, water, nutrients, or cells through the vasculature. In some cases, excessive, uncontrolled, or otherwise inappropriate vascular permeability or vascular leakage exacerbates or induces disease states including, e.g., edema associated with tumors including, e.g., brain tumors; ascites associated with malignancies; Meigs' syndrome; lung inflammation; nephrotic syndrome; pericardial effusion; pleural effusion; permeability associated with cardiovascular diseases such as the condition following myocardial infarctions and strokes and the like. The present invention contemplates treating those patients that have developed or are at risk of developing the diseases and disorders associated with abnormal vascular permeability or leakage.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: small cell lung cancer, gliblastoma, neuroblastomas, melanoma, breast carcinoma, gastric cancer, colorectal cancer (CRC), and hepatocellular carcinoma. Yet, in some embodiments, the cancer is selected from: non-small cell lung cancer, colorectal cancer, glioblastoma and breast carcinoma, including metastatic forms of those cancers.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenic agents, apoptotic agents, anti-tubulin agents, and other agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

An "angiogenic factor or agent" is a growth factor or its receptor which is involved in stimulating the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family and their receptors (VEGF-B, VEGF-C, VEGF-D, VEGFR1, VEGFR2 and VEGFR3), P1GF, PDGF family, fibroblast growth factor family (FGFs), TIE ligands (Angiopoietins, ANGPT1, ANGPT2), TIE1, TIE2, ephrins, Bv8, Delta-like ligand 4 (DLL4), Del-1, fibroblast growth factors: acidic (aFGF) and basic (bFGF), FGF4, FGF9, BMP9, BMP10, Follistatin, Granulocyte colony-stimulating factor (G-CSF), GM-CSF, Hepatocyte growth factor (HGF)/scatter factor (SF), Interleukin-8 (IL-8), CXCL12, Leptin, Midkine, neuropilins, NRP1, NRP2, Placental growth factor, Platelet-derived endothelial cell growth factor (PD-ECGF), Platelet-derived growth factor, especially PDGF-BB, PDGFR-alpha, or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), Alk1, CXCR4, Notch1, Notch4, Sema3A, Sema3C, Sema3F, Robo4, etc. It would further include factors that promote angiogenesis, such as ESM1 and Perlecan. It would also include factors that accelerate wound healing, such as growth hormone, insulin-like growth factor-I (IGF-I), VIGF, epidermal growth factor (EGF), EGF-like domain, multiple 7 (EGFL7), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12): 1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenic agent" or "angiogenic inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenic agent includes those agents that bind and block the angiogenic activity of the angiogenic factor or its receptor. For example, an anti-angiogenic agent is an antibody or other antagonist to an angiogenic agent as defined above, e.g., antibodies to VEGF-A or to the VEGF-A receptor (e.g., KDR receptor or Flt-1 receptor), anti-PDGFR inhibitors, small molecules that block VEGF receptor signaling (e.g., PTK787/ZK2284, SU6668, SUTENT/SU11248 (sunitinib malate), AMG706, or those described in, e.g., international patent application WO 2004/113304). Anti-angiogenic agents include, but are not limited to, the following agents: VEGF inhibitors such as a VEGF-specific antagonist, EGF inhibitor, EGFR inhibitors, Erbitux® (cetuximab, ImClone Systems, Inc., Branchburg, N.J.), Vectibix® (panitumumab, Amgen, Thousand Oaks, Calif.), TIE2 inhibitors, IGF1R inhibitors, COX-II (cyclooxygenase II) inhibitors, MMP-2 (matrix-metalloproteinase 2) inhibitors, and MMP-9 (matrix-metalloproteinase 9) inhibitors, CP-547,632 (Pfizer Inc., NY, USA), Axitinib (Pfizer Inc.; AG-013736), ZD-6474 (AstraZeneca), AEE788 (Novartis), AZD-2171), VEGF Trap (Regeneron/Aventis), Vatalanib (also known as PTK-787, ZK-222584: Novartis & Schering A G), Macugen (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof. Other angiogenesis inhibitors include thrombospondin1, thrombospondin2, collagen IV and collagen XVIII. VEGF inhibitors are disclosed in U.S. Pat. Nos. 6,534,524 and 6,235,764, both of which are incorporated in their entirety for all purposes. Anti-angiogenic agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known antiangiogenic factors); and, Sato (2003) *Int. J. Clin. Oncol.* 8:200-206 (e.g., Table 1 listing anti-angiogenic agents used in clinical trials).

The term "anti-angiogenic therapy" refers to a therapy useful for inhibiting angiogenesis which comprises the administration of an anti-angiogenic agent.

The term "CD20 expressing cancer" as used herein refers to all cancers in which the cancer cells show an expression of the CD20 antigen. Preferably CD20 expressing cancer as used herein refers to lymphomas (preferably B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma) c) marginal zone lymphomas (including extranodal marginal zone B cell lymphoma (Mucosa-associated lymphatic tissue lymphomas, MALT), nodal marginal zone B cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma) f) hairy cell leukemia, g) lymphocytic lymphoma, waldenstrom's macroglobulinemia, h) acute lymphocytic leukemia (ALL), chronic lymphocytic leukemia (CLL)/small lymphocytic lymphoma (SLL), B-cell prolymphocytic leukemia, i) plasma cell neoplasms, plasma cell myeloma, multiple myeloma, plasmacytoma j) Hodgkin's disease.

More preferably the CD20 expressing cancer is a B-Cell Non-Hodgkin's lymphoma (NHL). Especially the CD20 expressing cancer is a Mantle cell lymphoma (MCL), acute lymphocytic leukemia (ALL), chronic lymphocytic leukemia (CLL), B-cell diffuse large cell lymphoma (DLCL), Burkitt's lymphoma, hairy cell leukemia, follicular lymphoma, multiple myeloma, marginal zone lymphoma, post transplant lymphoproliferative disorder (PTLD), HIV associated lymphoma, waldenstrom's macroglobulinemia, or primary CNS lymphoma.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, *vinca* alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAIC), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma 11 and calicheamicin omegaII (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or 0 STAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: antiestrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.cndot.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKCalpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above; as well as combinations of two or more of the above.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (e.g., has a binding affinity (Kd) value of no more than about $1\times10^{-7}$ M, preferably no more than about $1\times10^{-8}$ M and preferably no more than about $1\times10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng,* 8(10):1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

II. Antibody Formulations and Preparation

The invention herein relates to stable aqueous formulations comprising an antibody. In some embodiments, the formulation comprises a monoclonal antibody, trehalose, and a buffer, wherein the weight ratio of the monoclonal antibody to the trehalose in the formulation is greater than or equal to 0.41 and less than 1.65, wherein the formulation has a pH of about 5.5 to about 7.0. In some embodiments, the formulation further comprises a buffer (such as sodium phosphate or histidine). In some embodiments, the formulation comprises (a) a monoclonal antibody in an amount of about 25 mg/mL to about 100 mg/mL; (b) trehalose in an amount of about 45 mM to about 634 mM; and (c) sodium phosphate in an amount of greater than 35 mM to about 100 mM, wherein said formulation has a pH of about 5.5 to about 7.0, and wherein the weight ratio of said monoclonal antibody to said trehalose in the formulation is greater than or equal to about 0.41 and less than 1.65. In some embodiments, the antibody in the formulation is stable at −20° C. for at least about 6 months, at least about 12 months, or at least about 18 months. In some embodiments, the trehalose may be substituted for a non-trehalose polyol. In some embodiments, the antibody binds VEGF.

A. Antibody Preparation

The antibody in the formulation is prepared using techniques available in the art for generating antibodies, exemplary methods of which are described in more detail in the following sections.

The antibody is directed against an antigen of interest. Preferably, the antigen is a biologically important polypeptide and administration of the antibody to a mammal suffering from a disorder can result in a therapeutic benefit in that mammal. However, antibodies directed against non-polypeptide antigens are also contemplated.

Where the antigen is a polypeptide, it may be a transmembrane molecule (e.g. receptor) or ligand such as a growth factor. Exemplary antigens include molecules such as vascular endothelial growth factor (VEGF); CD20; ox-LDL; ox-ApoB100; renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des (1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrns such as CD11a, CD11b, CD11c, CD18, an ICAM, VLA-4 and VCAM; a tumor associated antigen such as HER2, HER3 or HER4 receptor; and fragments of any of the above-listed polypeptides.

In certain embodiments of the invention, the molecular targets for antibodies encompassed by the invention include VEGF and CD20. In some embodiments, the antibody herein is one which binds to human VEGF. In some embodiments, the antibody herein is one which binds to human CD20.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the invention can be made using the hybridoma method first described by Kohler et al., Nature, 256:495 (1975), and further described, e.g., in Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), and Ni, Xiandai Mianyixue, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of the invention or a fragment thereof, and an adjuvant, such as monophosphoryl lipid A (MPL)/trehalose dicrynomycolate (TDM) (Ribi Immunochem. Research, Inc., Hamilton, Mont.). A polypeptide of the invention (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody of the invention. The binding specificity of monoclonal antibodies produced by hybridoma cells may be determined by immunoprecipitation or by an in vitro binding assay, such as radioimmunoassay (MA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

(iii) Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., *J. Mol. Biol.* (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-antigen clones is desired, the subject is immunized with antigen to generate an antibody response, and spleen cells and/or circulating B cells other peripheral blood lymphocytes (PBLs) are recovered for library construction. In one embodiment, a human antibody gene fragment library biased in favor of anti-antigen clones is obtained by generating an anti-antigen antibody response in transgenic mice carrying a functional human immunoglobulin gene array (and lacking a functional endogenous antibody production system) such that antigen immunization gives rise to B cells producing human antibodies against antigen. The generation of human antibody-producing transgenic mice is described below.

Additional enrichment for anti-antigen reactive cell populations can be obtained by using a suitable screening procedure to isolate B cells expressing antigen-specific membrane bound antibody, e.g., by cell separation using antigen affinity chromatography or adsorption of cells to fluorochrome-labeled antigen followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature,* 341: 544-546 (1989). However, for amplifying from cDNA, back primers can also be based in the leader exon as described in Jones et al., *Biotechnol.,* 9: 88-89 (1991), and forward primers within the constant region as described in Sastry et al., *Proc. Natl. Acad. Sci.* (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.,* 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature,* 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA,* 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene,* 128: 119-126 (1993), or in vivo by combinatorial infection, e.g., the lox P system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique* 1: 11-15 (1989)) in the method of Hawkins et al., *J. Mol. Biol.*, 226: 889-896 (1992) or in the method of Gram et al., *Proc. Natl. Acad. Sci USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities of about $10^{-9}$M or less.

Screening of the libraries can be accomplished by various techniques known in the art. For example, antigen can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized antigen under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA*, 88: 7978-7982 (1991), or by alkali, e.g. as described in Marks et al., *J. Mol. Biol.*, 222: 581-597 (1991), or by antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for antigen. However, random mutation of a selected antibody (e.g. as performed in some affinity maturation techniques) is likely to give rise to many mutants, most binding to antigen, and a few with higher affinity. With limiting antigen, rare high affinity phage could be competed out. To retain all higher affinity mutants, phages can be incubated with excess biotinylated antigen, but with the biotinylated antigen at a concentration of lower molarity than the target molar affinity constant for antigen. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-antigen clones may be selected based on activity. In certain embodiments, the invention provides anti-antigen antibodies that bind to living cells that naturally express antigen or bind to free floating antigen or antigen attached to other cellular structures. Fv clones corresponding to such anti-antigen antibodies can be selected by (1) isolating anti-antigen clones from a phage library as described above, and optionally amplifying the isolated population of phage clones by growing up the population in a suitable bacterial host; (2) selecting antigen and a second protein against which blocking and non-blocking activity, respectively, is desired; (3) adsorbing the anti-antigen phage clones to immobilized antigen; (4) using an excess of the second protein to elute any undesired clones that recognize antigen-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol.* Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-antigen antibody derived from a hybridoma of the invention can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA*, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

(iv) Humanized and Human Antibodies

Various methods for humanizing non-human antibodies are known in the art. For example, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to one embodiment of the method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies of the invention can be constructed by combining Fv clone variable domain sequence(s) selected from human-derived phage display libraries with known human constant domain sequence(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab)$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO 1, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol,* 152:5368 (1994).

Antibodies with more than two valencies are contemplated. For example, trispecific antibodies can be prepared. Tuft et al. *J. Immunol.* 147: 60 (1991).

(vii) Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Antibody Derivatives

The antibodies of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(x) Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and —II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human (3-interferon cDNA in mouse cells under the control of a thymidine kinase promoter from herpes simplex virus. Alternatively, the Rous Sarcoma Virus long terminal repeat can be used as the promoter.

(e) Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Envinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frupperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frupperda* cells.

Plant cell cultures of cotton, corn, potato, soybean, *petunia*, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, *Mather, Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

(h) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xi) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

B. Selecting Biologically Active Antibodies

Antibodies produced as described above may be subjected to one or more "biological activity" assays to select an antibody with beneficial properties from a therapeutic perspective. The antibody may be screened for its ability to bind the antigen against which it was raised. For example, for an anti-VEGF antibody, the antigen binding properties of the antibody can be evaluated in an assay that detects the ability to bind to VEGF. In another example, for an anti-CD20 antibody, the antigen binding properties of the antibody can be evaluated in an assay that detects the ability to bind to CD20.

In another embodiment, the affinity of the antibody may be determined by saturation binding; ELISA; and/or competition assays (e.g. RIA's), for example.

Also, the antibody may be subjected to other biological activity assays, e.g., in order to evaluate its effectiveness as a therapeutic. Such assays are known in the art and depend on the target antigen and intended use for the antibody.

To screen for antibodies which bind to a particular epitope on the antigen of interest (e.g., those which block binding of the anti-VEGF antibody of the example to VEGF), a routine cross-blocking assay such as that described in Antibodies, *A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

The term "expression of the CD20" antigen is intended to indicate an significant level of expression of the CD20 antigen in a cell, preferably on the cell surface of a T- or B-Cell, more preferably a B-cell, from a tumor or cancer, respectively, preferably a non-solid tumor. Patients having a "CD20 expressing cancer" can be determined by standard assays known in the art. For example, CD20 antigen expression is measured using immunohistochemical (IHC) detection, FACS or via PCR-based detection of the corresponding mRNA.

C. Preparation of the Formulations

After preparation of the antibody of interest (e.g., techniques for producing antibodies which can be formulated as disclosed herein will be elaborated below and are known in the art), the pharmaceutical formulation comprising it is prepared. In certain embodiments, the antibody to be formulated has not been subjected to prior lyophilization and the formulation of interest herein is an aqueous formulation. In certain embodiments, the antibody is a full length antibody. In one embodiment, the antibody in the formulation is an antibody fragment, such as an F(ab')$_2$, in which case problems that may not occur for the full length antibody (such as clipping of the antibody to Fab) may need to be addressed. The therapeutically effective amount of antibody present in the formulation is determined by taking into account the desired dose volumes and mode(s) of administration, for example. From about 25 mg/mL to about 100 mg/mL, or from about 30 mg/mL to about 100 mg/mL or from about 45 mg/mL to about 55 mg/mL is an exemplary antibody concentration in the formulation.

An aqueous formulation is prepared comprising the antibody in a pH-buffered solution. The buffer of this invention has a pH in the range from about 5.5 to about 7.0. In certain embodiments the pH is in the range from pH 5.5 to 6.5, in the range from pH 5.7 to 6.8, in the range from pH 5.8 to 6.5, in the range from pH 5.9 to 6.5, in the range from pH 6.0 to 6.5, or in the range from pH 6.2 to 6.5. In certain embodiments of the invention, the formulation has a pH of 6.2 or about 6.2. In certain embodiments of the invention, the formulation has a pH of 6.0 or about 6.0. Examples of buffers that will control the pH within this range include sodium phosphate and histidine (such as L-histidine). As used herein, references to "histidine" in a formulation or buffer may refer to any form of histidine known in the art, including without limitation histidine-HCl or histidine chloride, histidine acetate, histidine phosphate, histidine sulfate, and the like.

In some embodiments, the buffer contains phosphate (e.g., sodium phosphate) in the concentration of greater than 35 mM to less than or equal to about 100 mM. In some embodiments, the buffer contains phosphate (e.g., sodium phosphate) in the concentration of about 15 mM to about 100 mM. In certain embodiments of the invention, the buffer contains sodium phosphate in the concentration of about 15 mM, about 20 mM, about 22 mM, about 25 mM, about 28 mM, about 30 mM, about 35 mM, about 36 mM, about 40 mM, about 45 mM, about 50 mM, about 51 mM, about 55 mM, about 60 mM, about 65 mM, about 70 mM, about 75 mM, about 80 mM, about 85 mM, about 90 mM, about 95 mM, or about 100 mM. In some embodiments, the buffer contains sodium phosphate in a concentration less than about any of the following concentrations: 100 mM, 95 mM, 90 mM, 85 mM, 80 mM, 75 mM, 70 mM, 65 mM, 60 mM, 55 mM, 51 mM, 50 mM, 45 mM, 40 mM, 36 mM, 35 mM, 30 mM, 28 mM, 25 mM, 22 mM, or 20 mM. In some embodiments, the buffer contains sodium phosphate in a concentration greater than about any of the following concentrations: 15 mM, 20 mM, 22 mM, 25 mM, 28 mM, 30 mM, 35 mM, 36 mM, 40 mM, 45 mM, 50 mM, 51 mM, 55 mM, 60 mM, 65 mM, 70 mM, 75 mM, 80 mM, 85 mM, 90 mM, or 95 mM. That is, the concentration of sodium phosphate in the buffer may be any of a range of concentrations having an upper limit of about 100 mM, 95 mM, 90 mM, 85 mM, 80 mM, 75 mM, 70 mM, 65 mM, 60 mM, 55 mM, 51 mM, 50 mM, 45 mM, 40 mM, 36 mM, 35 mM, 30 mM, 28 mM, 25 mM, 22 mM, or 20 mM and an independently selected lower limit of about 15 mM, 20 mM, 22 mM, 25 mM, 28 mM, 30 mM, 35 mM, 36 mM, 40 mM, 45 mM, 50 mM, 51 mM, 55 mM, 60 mM, 65 mM, 70 mM, 75 mM, 80 mM, 85 mM, 90 mM, or 95 mM, wherein the lower limit is less than the upper limit.

In certain embodiments, the buffer contains histidine in the concentration of about 40 mM to about 100 mM. In certain embodiments, the buffer contains histidine in the concentration of about 15 mM to about 100 mM. In certain embodiments of the invention, the buffer contains histidine in the concentration of about 15 mM, about 20 mM, about 22 mM, about 25 mM, about 28 mM, about 30 mM, about 35 mM, about 36 mM, about 40 mM, about 45 mM, about 50 mM, about 51 mM, about 55 mM, about 60 mM, about 65 mM, about 70 mM, about 75 mM, about 80 mM, about 85 mM, about 90 mM, about 95 mM, or about 100 mM. In some embodiments, the buffer contains histidine in a concentration less than about any of the following concentrations: 100 mM, 95 mM, 90 mM, 85 mM, 80 mM, 75 mM, 70 mM, 65 mM, 60 mM, 55 mM, 51 mM, 50 mM, 45 mM, 40 mM, 36 mM, 35 mM, 30 mM, 28 mM, 25 mM, 22 mM, or 20 mM. In some embodiments, the buffer contains histidine in a concentration greater than about any of the following concentrations: 15 mM, 20 mM, 22 mM, 25 mM, 28 mM, 30 mM, 35 mM, 36 mM, 40 mM, 45 mM, 50 mM, 51 mM, 55 mM, 60 mM, 65 mM, 70 mM, 75 mM, 80 mM, 85 mM, 90 mM, or 95 mM. That is, the concentration of histidine in the buffer may be any of a range of concentrations having an upper limit of about 100 mM, 95 mM, 90 mM, 85 mM, 80 mM, 75 mM, 70 mM, 65 mM, 60 mM, 55 mM, 51 mM, 50 mM, 45 mM, 40 mM, 36 mM, 35 mM, 30 mM, 28 mM, 25 mM, 22 mM, or 20 mM and an independently selected lower limit of about 15 mM, 20 mM, 22 mM, 25 mM, 28 mM, 30 mM, 35 mM, 36 mM, 40 mM, 45 mM, 50 mM, 51 mM, 55 mM, 60 mM, 65 mM, 70 mM, 75 mM, 80 mM, 85 mM, 90 mM, or 95 mM, wherein the lower limit is less than the upper limit.

The formulation further comprises trehalose in an amount of about 45 mM to about 634 mM, about 50 mM to about 600 mM, or about 150 mM to about 400 mM. In some embodiments, the trehalose in the formulation is about 45 mM to about 600 mM, about 45 mM to about 550 mM, about 45 mM to about 500 mM, about 45 mM to about 450 mM, about 45 mM to about 400 mM, about 45 mM to about 350 mM, about 45 mM to about 300 mM, about 45 mM to about 250 mM, about 45 mM to about 200 mM, about 45 mM to about 180 mM, about 45 mM to about 150 mM, about 45 mM to about 140 mM, about 45 mM to about 135 mM, about 45 mM to about 130 mM, about 45 mM to about 120 mM, about 45 mM to about 110 mM, about 45 mM to about 100 mM, about 180 mM to about 634 mM, about 50 mM to about 600 mM, or about 150 mM to about 400 mM. In some embodiments, the trehalose in the formulation is about 45 mM, about 50 mM, about 60 mM, about 70 mM, about 80 mM, about 90 mM, about 100 mM, about 110 mM, about 120 mM, about 130 mM, about 135 mM, about 140 mM, about 150 mM, about 180 mM, about 200 mM, about 250 mM, about 300 mM, about 350 mM, about 400 mM, about 450 mM, about 500 mM, about 550 mM, about 600 mM, about 610 mM, about 620 mM, about 630 mM, or about 634 mM. In some embodiments, the formulation contains trehalose in a concentration less than about any of the following concentrations: 634 mM, 630 mM, 620 mM, 610 mM, 600 mM, 550 mM, 500 mM, 450 mM, 400 mM, 350 mM, 300 mM, 250 mM, 200 mM, 180 mM, 150 mM, 140 mM, 135 mM, 130 mM, 120 mM, 110 mM, 100 mM, 90 mM, 80 mM, 70 mM, 60 mM, or 50 mM. In some embodiments, the formulation contains trehalose in a concentration greater than about any of the following concentrations: 45 mM, 50 mM, 60 mM, 70 mM, 80 mM, 90 mM, 100 mM, 110 mM, 120 mM, 130 mM, 135 mM, 140 mM, 150 mM, 180 mM, 200 mM, 250 mM, 300 mM, 350 mM, 400 mM, 450 mM, 500 mM, 550 mM, 600 mM, 610 mM, 620 mM, or 630 mM. That is, the concentration of trehalose in the formulation may be any of a range of concentrations having an upper limit of about 634 mM, 630 mM, 620 mM, 610 mM, 600 mM, 550 mM, 500 mM, 450 mM, 400 mM, 350 mM, 300 mM, 250 mM, 200 mM, 180 mM, 150 mM, 140 mM, 135 mM, 130 mM, 120 mM, 110 mM, 100 mM, 90 mM, 80 mM, 70 mM, 60 mM, or 50 mM and an independently selected lower limit of about 45 mM, 50 mM, 60 mM, 70 mM, 80 mM, 90 mM, 100 mM, 110 mM, 120 mM, 130 mM, 135 mM, 140 mM, 150 mM, 180 mM, 200 mM, 250 mM, 300 mM, 350 mM, 400 mM, 450 mM, 500 mM, 550 mM, 600 mM, 610 mM, 620 mM, or 630 mM, wherein the lower limit is less than the upper limit.

In some embodiments, the weight ratio of the monoclonal antibody to trehalose in the formulation is greater than or equal to 0.41 and less than 1.65. In some embodiments, the weight ratio of the monoclonal antibody to trehalose in the formulation is 0.41 to 0.73. In some embodiments, the weight ratio of the monoclonal antibody to the trehalose is 0.73 to 1.47. In some embodiments, the weight ratio of the monoclonal antibody to the trehalose is 0.49 to 1.47. In some embodiments, the weight ratio of the monoclonal antibody to the trehalose is any of 0.41, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, and 1.64, including every value in between these numbers. As used herein, the weight of trehalose in the formulation for calculating the weight ratio of the antibody to the trehalose is based on the amount trehalose dihydrate (MW 378.33). If other forms of trehalose (e.g., trehalose anhydrous) are used, the weight of the trehalose in the formulation should be converted to the weight of trehalose dihydrate with the same molar concentration.

In some embodiments, a polyol other than trehalose may be substituted for trehalose. For example, sucrose, mannitol, lactose, glycerol, and/or propylene glycol may be substituted for trehalose. Therefore, in any reference to trehalose in an antibody formulation described herein, said trehalose may optionally be substituted for a polyol other than trehalose (e.g., those listed above).

A surfactant can optionally be added to the antibody formulation. Exemplary surfactants include nonionic surfactants such as polysorbates (e.g. polysorbates 20, 80 etc) or poloxamers (e.g. poloxamer 188, etc.). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, from about 0.01% to about 0.1%, or from about 0.02% to about 0.06%, or about 0.03% to about 0.05%. In certain embodiments, the surfactant is present in the formulation in an amount of 0.04% or about 0.04%. In certain embodiments, the surfactant is present in the formulation in an amount of 0.02% or about 0.02%. In one embodiment, the formulation does not comprise a surfactant.

In one embodiment, the formulation contains the above-identified agents (e.g., antibody, buffer, trehalose, and/or surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, preferably from about 0.5% to about 1%. One or more other pharmaceutically acceptable carriers, excipients or stabilizers such as those described in *Remington's Pharmaceutical Sciences* 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; anti-oxidants including ascorbic acid and methionine; chelating agents such as EDTA; metal complexes (e.g. Zn-protein complexes); biodegradable polymers such as polyesters; and/or salt-forming counterions. Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

While the various descriptions of chelators herein often focus on EDTA, it will be appreciated that other metal ion chelators are also encompassed within the invention. Metal ion chelators are well known by those of skill in the art and include, but are not necessarily limited to aminopolycarboxylates, EDTA (ethylenediaminetetraacetic acid), EGTA (ethylene glycol-bis(beta-aminoethyl ether)-N,N,N',N'-tetraacetic acid), NTA (nitrilotriacetic acid), EDDS (ethylene diamine di succinate), PDTA (1,3-propylenediaminetetraacetic acid), DTPA (diethylenetriaminepentaacetic acid), ADA (beta-alaninediacetic acid), MGCA (methylglycinediacetic acid), etc. Additionally, some embodiments herein comprise phosphonates/phosphonic acid chelators.

The formulation herein may also contain more than one protein as necessary for the particular indication being treated, preferably those with complementary activities that do not adversely affect the other protein. For example, where the antibody is anti-VEGF, it may be combined with another agent (e.g., a chemotherapeutic agent, and anti-neoplastic agent).

In some embodiments, the physical stability, chemical stability, or biological activity of the antibody in the formulation is evaluated or measured. Any methods known the art may be used to evaluate the stability and biological activity. In some embodiments, the antibody in the formulation is stable at −20° C. for at least about 12 months, at least about 18 months, at least about 21 months, or at least about 24 months (or at least about 52 weeks). In some embodiments, the stability is measured by the formation of high molecular weight species (HMWS) in the formulation after storage. In some embodiments, the percent of HMWS in the formulation is less than any of about 0.8%, about 0.9%, or about 1% after storage at −20° C. for at least about 6 months, at least about 12 months, at least about 18 months, or at least about 24 months. In some embodiments, the total aggregates in the formulation is less than any of about 2.5%, or about 3% after storage at −20° C. for at least about 6 months, at least about 12 months, at least about 18 months, or at least about 24 months.

The formulations to be used for in vivo administration should be sterile. This is readily accomplished by filtration through sterile filtration membranes, prior to, or following, preparation of the formulation.

III. Administration of Antibody Formulations

In some embodiments, a formulation as described herein is for administration to a subject. The formulation may be administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intraocular, intra-articular, intrasynovial, intrathecal, oral, topical, or inhalation routes. In one embodiment, the formulation is administered to the mammal by intravenous administration. For such purposes, the formulation may be injected using a syringe or via an IV line, for example. In one embodiment, the formulation is administered to the mammal by subcutaneous administration.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody is suitably administered to the patient at one time or over a series of treatments and may be administered to the patient at any time from diagnosis onwards. The antibody may be administered as the sole treatment or in conjunction with other drugs or therapies useful in treating the condition in question.

As a general proposition, the therapeutically effective amount of the antibody administered will be in the range of about 0.1 to about 50 mg/kg of patient body weight whether by one or more administrations, with the typical range of antibody used being about 0.3 to about 20 mg/kg, preferably about 0.3 to about 15 mg/kg, administered daily, for example. However, other dosage regimens may be useful. In one embodiment, the antagonist is an anti-VEGF antibody that is administered at a dose of about 100 or 400 mg every 1, 2, 3, or 4 weeks or is administered a dose of about 1, 3, 5, 7.5, 10, 15, or 20 mg/kg every 1, 2, 3, or 4 weeks. The dose may be administered as a single dose or as multiple doses (e.g., 2 or 3 doses), such as infusions. The progress of this therapy is easily monitored by conventional techniques.

IV. Articles of Manufacture

In another embodiment of the invention, an article of manufacture is provided comprising a container which holds the aqueous pharmaceutical formulation of the invention and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Effects of Excipient Solubility on mAb Stability in Frozen Trehalose Formulations This study was designed to assess the effects of freeze rate, storage temperature, and formulation composition on trehalose phase distribution and protein stability in frozen solutions. In addition to elucidating the phase distribution of trehalose crystallization in frozen solutions, the results of this study have numerous practical implications. Presumably, the effectiveness of trehalose as a stabilizer of proteins depends on the phase distribution of trehalose in solution. Thus, understanding the phase distribution of trehalose that result from different compositions, freeze rates, and storage temperatures inform the development of robust formulations and freeze processes.

Materials and Methods
Materials and Sample Preparation

Three IgG1 full length monoclonal antibodies (mAb1, bevacizumab, and mAb3) with an approximate molecular weight of 145 kilodatons were cloned, expressed in Chinese hamster ovary cell lines, and purified.

For the storage temperature, and freeze rate studies, mAb1 was formulated at 25 mg/mL in 2.1% (wt/v) trehalose, 5 mM histidine-hydrochloride, at pH 6.0 with 0.01% polysorbate 20 (wt/v), and Water for Injection, USP; bevacizumab was formulated at 25 mg/mL in 5.4% (wt/v) trehalose, 51 mM sodium phosphate, at pH 6.2 with 0.04% polysorbate 20 (wt/v), and Water for Injection, USP; and mAb3 was formulated at 20 mg/mL in 8.2% (wt/v) trehalose, 20 mM histidine-acetate, at pH 6.2 with 0.02% polysorbate 20 (wt/v), and Water for Injection, USP.

For the excipient solubility study, bevacizumab was formulated at 25 mg/mL in 51 mM sodium phosphate, at pH 6.2 with 0.04% polysorbate 20 (wt/v), Water for Injection, USP (control sample) with 6.0% (wt/v) of either sucrose, trehalose, or mannitol.

For the formulation studies, bevacizumab was evaluated at three mAb concentrations (0, 25, and 100 mg/mL) in 20 mM histidine-hydrochloride at pH 6.0 with varying amounts of trehalose (0%, 1.7%, 3.4%, 5.1%, 6.8%, 8.6%, 10.3%, 12.0%, 13.7%, 15.4%, 17.1%, 20.5%, 24.0%, 27.4%, 30.8%, and 34.2% wt/v) with and without 0.04% polysorbate 20. These 64 different formulations as well as 32 vehicle blanks containing 0 mg/mL of bevacizumab were formulated in a 96-well Greiner microplate.

Additional solutions were prepared with 0.0, 2.0, 4.0, and 8.0% (wt/v) trehalose in 20 mM histidine-acetate, at pH 5.5, and Water for Injection. Fifty microliters of pHydrion (pH Range: 0-7) pH-indicator dye (Micro Essential Laboratory, NY) was dispensed into a 10 cc glass vial and allowed to evaporate. Approximately four milliliters of the various trehalose formulations were added to the vial and the dye was allowed to dissolve in the solution. Photographs of frozen trehalose solutions were obtained using an Olympus Stylus 770SW digital camera (Olympus America Inc., NJ) in supermacro mode.

Formulation buffers for all samples were prepared with compendial grade (USP, NP, EP) chemicals, and deionized water purified using Elga PURELAB Ultra (Celle, Germany) water purification system. Formulation study samples were exhaustively dialyzed into formulation buffers using Pierce Slide-A-Lyzer dialysis cassettes or Millipore (Billerica, Mass.) Amicon Ultra centrifugation tubes (10 kD MWCO) and mAb stock solution pH was verified for each dialyzed sample. Following dialysis, samples were concentrated by ultrafiltration using Amicon Ultra centrifugal filtration devices (10 kD MWCO).

Controlled Freeze

To prepare the samples for slow and normal freezing, two milliliter sample aliquots were dispensed into autoclaved 5 cc glass vials and sealed with 20 mm Lyo-Stoppers using aseptic technique in a ventilated biosafety hood with laminar air flow. Slow freezing was accomplished by placing sample vials in a lyophilizer on pre-cooled shelves and held between $-1°$ C. and $-3°$ C. for 24 hours. To control for supercooling, ice was nucleated by applying frozen $CO_2$ to the side of each vial until ice formation and then the temperature was linearly decreased to $-40°$ C. over 144 hours at a rate of approximately $-0.3°$ C./min.

Normal freezing was accomplished by placing sample vials in a freezer at $-20°$ C. until samples were completely frozen. To control for supercooling, ice was nucleated by applying frozen $CO_2$ to the side of each vial until ice formation.

Fast freezing was accomplished by quench cooling fifty microliter sample aliquots drop-wise into liquid nitrogen. The freezing endpoint was determined by the increased opacity and the sinking of the sphere from the surface into a stainless steel mesh collection basket. After freezing, one-milliliter aliquots of bulk drug substance frozen pellets were removed from the liquid nitrogen and transferred into sterile, pre-chilled 5 cc glass vials. The vials were then stored on frozen $CO_2$, and sealed with 20 mm Lyo-Stoppers. The formulation screen samples were fast frozen in 96-well microplates using liquid nitrogen. Immediately after the microplates were frozen, the samples were nucleated by scratching the ice surface with a 24 gauge needles (BD, Franklin Lakes, N.J.).

Isothermal Hold

Samples frozen at the three freeze rates (slow, normal, and fast) by the methods described were transferred to three freezer units with set points of $-20°$ C., $-14°$ C., and $-8°$ C. with a range of $±2°$ C. for frozen storage. The freezer temperature was monitored using a Yokogawa temperature monitoring system (Yokogawa Meters and Instruments Corporation, Tokyo, Japan). Sample vials were pulled after 0, 1, 2, 3, 6, 9 and 12 months of isothermal, frozen storage and placed on the lab counter bench under ambient conditions (approximately 22° C.) and allowed to thaw prior to analysis.

The formulation screen sample microplates were stored at two temperatures ($-20±2°$ C., and $-40±2°$ C.). The freezer temperature was monitored using a Yokogawa temperature monitoring system (Yokogawa Meters and Instruments Corporation, Tokyo, Japan).

Sample microplates for SEC analysis were stored isothermally for up to 365 days. Following frozen storage, microplates were thawed on the lab counter bench under ambient conditions (approximately 22° C.) prior to analysis. Control (0 day) samples were thawed immediately following completion of the freezing process. Sample glass microplates for FTIR analysis were pulled after 365 days of isothermal, frozen storage and lyophilized for trehalose crystallization analysis. Control (0 month) samples were lyophilized immediately following completion of the freezing process.

Lyophilization

Samples intended for trehalose crystallization determination were first freeze-dried using a LyoStar II lyophilizer unit controlled by LyoManager II software (FTS Systems, Stone Ridge, N.Y.). The frozen samples were placed on a pre-cooled shelf and held at $-35°$ C. for 7 hours prior to primary drying. Primary drying was achieved under a system pressure of 150 μm Hg by linearly increasing the shelf temperature to 20° C. at a rate of 0.2° C./min, followed by a 40 hour hold at 20° C. Secondary drying was performed by linearly increasing shelf temperature to 30° C. at 0.2° C./min, followed by an 8 hour hold at 30° C. Thermocouples were placed in various sample vials to monitor temperature during freeze-drying. Following secondary drying, sample vials were stoppered while still under vacuum to prevent samples from hydrating prior to analysis. Low volume (300 microliter), formulation screen samples were lyophilized in 96-well glass plates (Zinsser, Germany) using the same lyophilization method.

Size Exclusion Chromatography

To measure the molecular size distribution of the three drug substances, HPSEC (High Performance Size Exclusion Chromatography) analysis was implemented using a TosohHaas TSKgel G3000 SWxl (7.8 mm×30 cm, 250 Å pore size, 5 μm particle size) column on the Agilent 1200 HPLC system (Agilent Technologies, Santa Clara, Calif.) or equivalent using a 0.2 M potassium phosphate, 0.25 M potassium chloride, pH 6.2 mobile phase solution. The flow rate was 0.5 mL/min and the run time was 30 minutes. Sample chamber temperature was 5° C. and injection mass was 100 micrograms. The column outlet signal was monitored with a Diode Array Detector measuring absorbance at 280 nm using 360 nm as a reference signal. Data analysis and UV peak integration was then performed using Chromeleon Software (Dionex, Sunnyvale, Calif.) to quantify the percent of molecular aggregate, monomer and fragment present in each sample. Low volume, formulation screen samples were analyzed in Greiner (GREINER INFO, CITY), 96-well polypropylene microplates using the SEC method described with a flow rate of 1.0 mL/min and a run time of 15 minutes. Prior to SEC analysis the bevacizumab samples were diluted in 20 mM histidine-hydrochloride pH 6.0 and held at 30° C. for 24 hours to resolve dissociable aggregates prior to SEC analysis. Sample chamber temperature was 30° C. and injection mass was 100 micrograms.

Concentration Measurement

The UV absorbance of each sample was measured by recording the absorbance at 279 nm and 320 nm in a quartz cuvette with 1-cm path length on an Agilent 8453 spectrophotometer using Chemstation software (Agilent Technologies, Santa Clara, Calif.). The UV concentration determination was calculated by using the absorptivities of 1.50, 1.70, and 1.45 $(mg/ml)^{-1}$ $cm^{-1}$ for mAb I, bevacizumab and mAb3, respectively. The measurements were blanked against the appropriate buffers.

Turbidity Analysis

The turbidity of the samples was measured by recording the average absorbance from 340-360 nm in a quartz cuvette with 1-cm path length (Eckhardt, B. M., et al. (1991) *Pharm. Res.* 8:1360-4) on an HP8453 spectrophotometer using Chemstation software (Agilent Technologies, Santa Clara, Calif.). Sterile water for injection was used to blank the instrument prior to analyses. Turbidity analysis of formulation screen samples was performed on a UV transparent, Corning half area, 96-well microplate using Spectramax M2 instrument (Molecular Devices, Sunnyvale). The turbidity was measured against a Sterile Water for Injection blank and the turbidity value measured by recording the average of the absorbance from 340-360 nm.

FT-NIR Spectroscopy

The percent trehalose crystallization was determined using near infrared diffuse reflectance spectroscopy. Data collection, calibration, and analysis methods used in this study were adapted from previous work focused on characterizing the spectral differences between amorphous trehalose and crystalline trehalose polymorphs (Connolly, B., et al. (2010) *Anal. Biochem.* 399(1):48-57). Using these methods, sample NIR spectra were recorded from 10,000-4,000 $cm^{-1}$ using 32 averaged scans with 4 $cm^{-1}$ resolution on a Nicolet Antaris FT-Near IR Analyzer equipped with an integrating sphere module (Thermo Fisher Scientific, Waltham, Mass.). Percent trehalose crystallization was calculated using normalized peak intensity ratios of bands at 4306 $cm^{-1}$ and 4291 $cm^{-1}$ (Connolly, B., et al. (2010) *Anal. Biochem.* 399(1):48-57). Data analysis was conducted using a linear regression analysis with MATLAB (R2007a, The MathWorks, Natick, Massachussetts) (Connolly, B., et al. (2010) *Anal. Biochem.* 399(1):48-57). Low volume (300 microliter) formulation screen samples were lyophilized and then analyzed for percent trehalose crystallization using the same method.

Results

It is of significant interest to understand if trehalose crystallization impacts protein stability at pharmaceutically relevant (≤10% wt/v) concentrations. To evaluate the impact of nominal trehalose concentration on excipient crystallization, solutions were prepared with 0.0, 2.0, 4.0 and 8.0% (wt/v) trehalose dihydrate in the presence of pH indicating dye to better visualize crystallization. The samples were frozen using the normal freeze rate and stored at −20° C. for 6 days. Following induced nucleation, trehalose crystallization was visually observed in all frozen trehalose solutions (FIG. 1). Visual inspection of the frozen solutions indicates that the extent of crystallization increases proportionally with the nominal trehalose concentration. For example, the highest nominal trehalose concentration evaluated (FIG. 1D: 8.0% wt/v) resulted in substantially more crystallization compared with the solutions that contained 0.0% (FIG. 1A), 2.0% (FIG. 1B), and 4.0% (FIG. 1C) trehalose (wt/v).

Although pharmaceutically relevant trehalose concentrations (≤10% wt/v) are well below the solubility limit in unfrozen solutions (FIG. 2A), during the freezing process, trehalose is concentrated substantially and, at lower temperatures, the solubility for trehalose is significantly lower (Miller, D. P., et al. (1997) *Pharm. Res.* 14:578-90). The higher concentration started at ambient temperature certainly exceeds the solubility at the frozen storage temperature. With trehalose above its solubility limit in the freeze concentrate, it would only require a nucleation event to initiate crystallization.

Example 2: Effects of Excipient Crystallization on mAb Stability in Frozen Trehalose Formulations Crystallization of carbohydrates during freezing, freeze-drying, and frozen storage has been shown to impact the physical stability of protein drugs. For example, mannitol has been shown to crystallize during freeze-drying and result in conformational changes, aggregation, and loss of activity for various proteins (Sharma, V. K. and Kalonia, D. S. (2004) *AAPS PharmSciTech.* 5:E10; Cavatur, R. K., et al. (2002) *Pharm. Res.* 19:894-900); Izutsu, K., et al. (1994) *Chem. Pharm. Bull.* (Tokyo) 42:5-8); and Izutsu, K., et al. (1993) *Pharm. Res.* 10:1232-7). Although at ≤40° C. trehalose is more soluble than mannitol, it is significantly less soluble than sucrose, which is generally regarded as a non-crystallizing excipient (FIG. 2A).

Figure 2B:
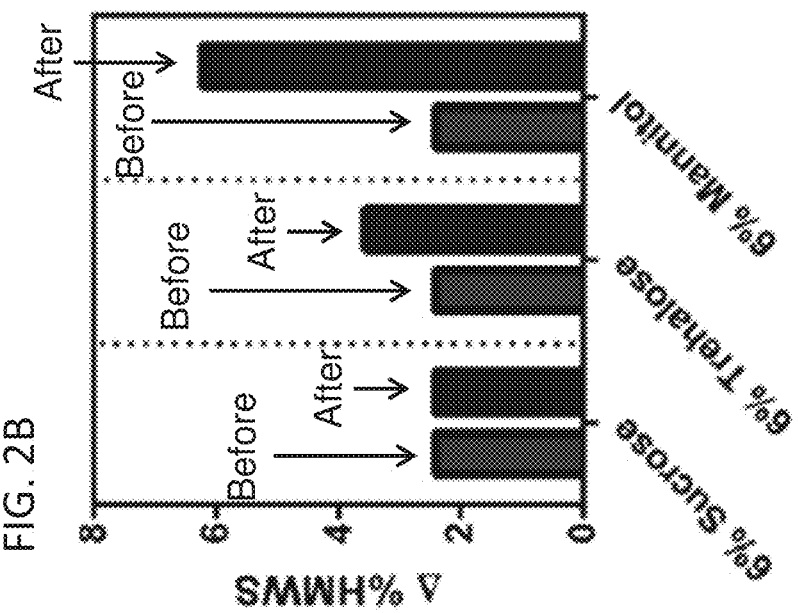
FIG. 2B depicts the percent high molecular weight species of bevacizumab in various cryoprotectant formulations before and after freezing and induced nucleation for 28 days at −20° C. as determined by HP-SEC, as labeled.

To evaluate the effects of excipient solubility on protein stability in frozen solutions, bevacizumab solutions were prepared with equivalent concentrations of sucrose, trehalose, and mannitol. Samples were frozen at the normal freezing rate, induced nucleation, and stored frozen at −20° C. for 28 days. SEC data demonstrate that after frozen storage no increase in aggregation was observed in the sucrose formulation; a small increase (~1%) in aggregation was observed in the trehalose formulation; and a large increase (~3%) in aggregation was observed in the mannitol formulation (FIG. 2B).

These results establish a rank-order correlation between excipient solubility and protein aggregation. As expected, carbohydrates with lower solubility at −20° C. result in larger increases in aggregation (FIG. 2B). Specifically of interest, the results suggest that the solubility of trehalose at −20° C. is sufficiently low that it may crystallize and result in protein aggregation at pharmaceutically relevant concentrations (2-10% wt/v).

Example 3: Effects of Freezing Rate on mAb Stability in Frozen Trehalose Formulations The SEC data for the three mAb formulations demonstrated that freezing rate does impact protein stability (see Table 1 below).

TABLE 1

Summary of trehalose phases after 12 months frozen storage

| Protein | Total Trehalose (% wt/v) | Freeze Rate | Δ Aggregation (%) | | | Crystallized Trehalose (% wt/v) | | | Amorphous Trehalose (% wt/v) | | |
|---|---|---|---|---|---|---|---|---|---|---|---|
| | | | −20° C. | −14° C. | −8° C. | −20° C. | −14° C. | −8° C. | −20° C. | −14° C. | −8° C. |
| mAb1 | 2.1 | Fast | 0.1 | 0.6 | 0.2 | 0.2 | 0.1 | 0.2 | 1.8 | 1.9 | 1.9 |
| | | Normal | 0.0 | 0.0 | 0.1 | 0.0 | 0.1 | 0.1 | 2.0 | 2.0 | 2.1 |
| | | Slow | 0.0 | 0.0 | 0.1 | 0.0 | 0.0 | 0.0 | 2.0 | 2.0 | 2.1 |
| Bevacizumab | 5.4 | Fast | 1.7 | 1.4 | 0.4 | 2.5 | 2.5 | 1.6 | 3.0 | 2.9 | 3.8 |
| | | Normal | 0.1 | 0.0 | 0.1 | 0.3 | 0.3 | 0.3 | 5.1 | 5.1 | 5.2 |
| | | Slow | 0.2 | 0.2 | 0.1 | 0.3 | 0.3 | 0.2 | 5.1 | 5.2 | 5.2 |
| mAb3 | 8.2 | Fast | 3.1 | 2.1 | 0.9 | 5.1 | 5.7 | 5.5 | 3.2 | 2.5 | 2.7 |
| | | Normal | 0.0 | 0.0 | 0.1 | 0.1 | 0.5 | 0.2 | 8.1 | 7.7 | 8.0 |
| | | Slow | 0.0 | 0.0 | 0.1 | 0.3 | 0.2 | 0.2 | 7.9 | 8.1 | 8.0 |

In general, the monoclonal antibodies aggregated following freezing at the fast rate (>100° C./min) and did not aggregate at the slower freezing rates (<1° C./min). It was observed that no significant aggregation was measured in any of the three drug substances (mAb1, bevacizumab and mAb3) frozen at the slower freezing rates (<1° C./min) regardless of long-term storage temperature (Table 1). However, all bevacizumab and mAb3 samples frozen at the faster freezing rate (>100° C./min) showed significant increases in aggregation over time (Table 1). Even fast frozen mAb1, included as a negative control, showed minor increases in aggregation during the course of the study (Table 1). For all fast frozen samples, the majority of aggregation observed during storage appears to occur within the first six months (FIG. 3). Subsequently, the rate of aggregation decreases significantly between six and twelve months—changes are sufficiently small during this period so that measured aggregation could potentially be attributable to sample and/or assay variability.

Without wishing to be bound to theory, it is thought that freezing at the fast rate represents a stress condition for antibody stability. For example, upon freezing at the fast rate, changes in aggregation in antibody formulations were observed after one month, whereas under commercial freezing and storage conditions aggregation may remain constant for 9 months or more. It is thought that fast freezing represents a stress condition under which antibody formulations undergo aggregation much faster than commercial freezing and storage conditions. As a result, this stress condition may be used to evaluate the susceptibility of an antibody formulation to aggregation, independent of the amount of time the formulation is stored.

Figure 4A:
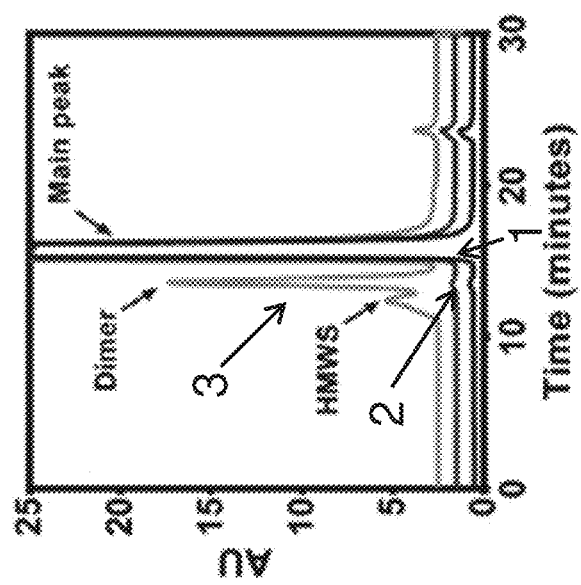
FIGS. 4A and 4B show representative size exclusion chromatography (SEC) chromatograms of mAb3 monomer, dimer, and high molecular weight species (HMWS).

SEC overlay of mAb3 samples frozen at the three freeze rates and stored at −20° C. for 12 months demonstrates that there was an observable increase in aggregated species (dimer and high molecular weight) in the fast frozen mAb3 sample (FIG. 4A). Conversely, the samples frozen at the slow and normal freeze rates showed no significant increases in percent aggregate and the data overlays closely compared to the study control (FIG. 4A). Also, the fast freeze bevacizumab samples showed increases in soluble aggregate (Table 1) and the formation of precipitates as determined by turbidity analysis and visual inspection. These precipitates have previously been characterized as protein-related, and have concomitant decreases in UV absorbance following removal by filtration using a 0.2 micron PVDF filter.

Figure 5:
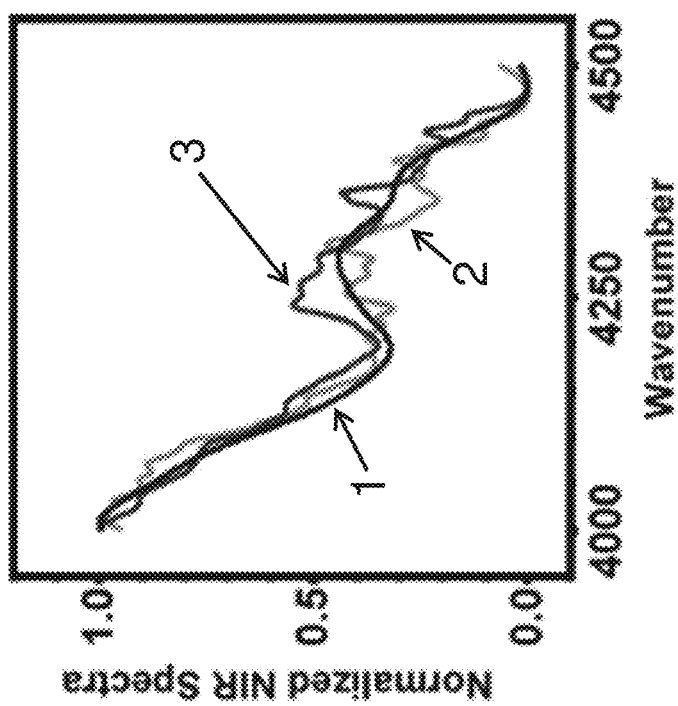
FIG. 5 shows normalized NIR spectra of the three trehalose forms discussed in this study: amorphous trehalose (1), trehalose anhydrate (crystalline) (2), and trehalose dihydrate (crystalline) (3), as labeled.

Application of a near infrared diffuse reflectance spectroscopy method used in combination with a linear regression model proved capable of quantifying relative amounts of amorphous and crystalline trehalose in the presence of protein by taking advantage of clear difference in previously characterized spectral region between 4000-4500 cm$^{-1}$ (Connolly, B., et al. (2010) Anal. Biochem. 399(1):48-57). FT-NIR spectra of pure samples of the three known trehalose phases illustrated the key spectral differences between amorphous, crystalline anhydrate and crystalline dihydrate (FIG. 5). Analysis of the 12 month samples by FT-NIR spectroscopy demonstrates that there was measurable amounts of trehalose crystallization in the fast freeze samples for mAb1 (FIG. 6A3), bevacizumab, (FIG. 6B3), and mAb3 (FIG. 6C3) (Table 1), there was no measurable amounts of trehalose crystallization in the slow and normal freeze samples for mAb1 (FIGS. 6A1-2), bevacizumab (FIGS. 6B1-2), or mAb3 (FIGS. 6C1-2). Fast freeze sample spectra obtained following twelve months of frozen storage at the various storage temperatures display sharp peak shifts in key spectral regions associated with trehalose dihydrate (FIGS. 6B3 and 6C3) and contain between 30 and 70 percent (1.6% to 5.7% wt/v) crystalline trehalose dihydrate, retaining ≥2.5% (wt/v) amorphous trehalose in the frozen solution.

Interestingly, observed increases in protein aggregation were associated with increases in trehalose crystallization. For example, fast frozen mAb1 samples stored at −20° C. for 12 months were found to have 0.2% (wt/v) crystalline trehalose dihydrate and 0.1% increase in aggregation, whereas the bevacizumab and the mAb3 samples fast frozen and stored at −20° C. for 12 months were found to have 2.5% and 5.1% (wt/v) crystalline trehalose dihydrate and 1.7% and 3.1% increase in aggregation, respectively (Table 1). This rank-order correlation of percent trehalose dihydrate and mAb aggregation suggests that the concentration of crystallized trehalose impacted protein stability.

As a control, samples were fast frozen and immediately analyzed by SEC and FT-NIR to evaluate the immediate impact of rapid cooling and freeze-drying on crystal formation and protein aggregation. No change in protein aggregation was observed (data not shown). Additionally, FT-NIR spectra obtained for the fast frozen $T_0$ sample set reveal that the sugar was predominantly amorphous in character, containing less than five percent crystalline trehalose dihydrate, which is near the detection limits of the method. These results demonstrate that there is no immediate impact on protein aggregation or trehalose phase distribution following fast freezing. Thus, measured increases in trehalose crystallization and protein aggregation during this study represent changes that occur in a time-dependent fashion during storage.

The results from the freeze rate studies provide insight into the effects of freeze rate on both trehalose crystallization and mAb aggregation. As discussed previously, fast freezing increases the interfacial surface area of the ice crystals and provides additional nucleation sites. Without wishing to be bound to theory, these additional nucleation sites formed in fast frozen samples are thought to increase the probability that a nucleation event may occur. Conversely, the larger ice crystals formed in the samples frozen at the slow and normal freezing rates have a lower surface area, which is thought to decrease the probability of a nucleation event.

Figure 4B:
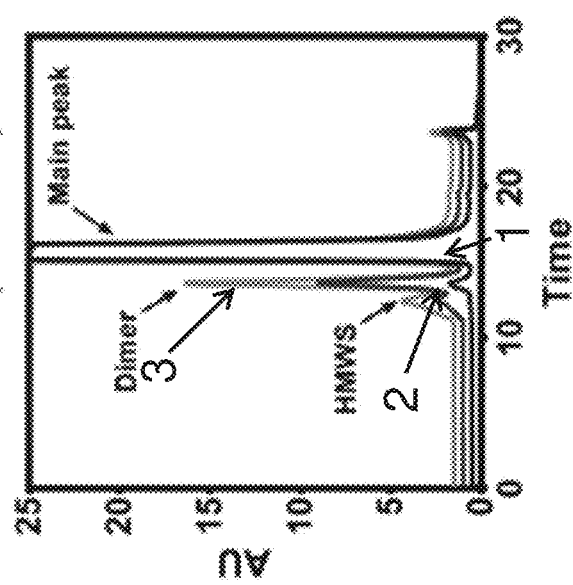

Example 4: Effects of Storage Temperature on mAb Stability in Frozen Trehalose Formulations The twelve month aggregation data demonstrates that storage temperature does impact protein stability (FIG. 3). In general, mAb3 samples fast frozen and stored twelve months at −20° C. aggregated to the greatest extent (FIG. 3C). Interestingly, the initial rate of aggregation of bevacizumab and mAb3 was more rapid in fast frozen samples stored at −14° C. with the rate of aggregation decreasing earlier than those stored at −20° C. (FIG. 3), which may be due to the chaotic nature of nucleation events. Samples fast frozen and stored at −8° C., the warmest storage temperature, generally showed both the lowest rate and extent of aggregation throughout the course of the study (FIG. 3). The chromatogram overlay in FIG. 4B shows the observed differences in SEC profiles for fast frozen mAb3 samples stored twelve months at the three respective storage temperatures. Fast freeze samples stored at higher temperatures (e.g., −8° C.) aggregated to a lesser extent; and conversely, samples stored at lower temperatures (e.g., −20° C.) aggregated to a greater extent for bevacizumab and mAb3.

The storage temperature dependence of protein aggregation in this study gives additional insight into the mechanism of protein aggregation in the frozen solution. Interestingly, the storage temperature determines the dependence between protein aggregation and trehalose crystallization (Table 1). In general, samples fast frozen and stored at −8° C., −14° C. and −20° C. showed no significant difference in the extent of trehalose crystallization, yet samples stored at the lower temperature (−20° C.) aggregated to greater extents than those stored at the higher temperatures (−14° C. and −8° C., respectively) (FIG. 3). For example, even though the fast frozen mAb3 samples stored for 12 months had between 61%-69% of trehalose crystallized for all storage temperatures, the amount of aggregation increased at more negative storage temperatures. For example, frozen samples aggregated 0.3%, 2.1%, and 3.1% following 12 months storage at −8° C., −14° C., and −20° C., respectively (Table 1). This trend demonstrates that a comparable amount of trehalose crystallization in two samples can result in more protein aggregation with storage at lower temperatures (−20° C.) than at higher temperatures (−14° C. and −8° C., respectively).

These temperature dependent trends suggest that molecular mobility and the physical properties (i.e., ice morphology) of the frozen environment may play critical roles in trehalose-crystallization induced protein aggregation. The range of storage temperatures surveyed (−20° C., −14° C. and −8° C.) are above the glass transition temperatures for these solutions (Tg' Range: −29.5 to −32° C.) and thus some mobility is expected. All the fast frozen samples are frozen in the same manner, thus presumably, samples with the same composition have similar ice morphologies and distributions of solutes immediately following freezing. After freezing, however, storage temperature dictates the long-term solute concentration and diffusion rates of trehalose and protein molecules in the freeze concentrate. Because of the size difference between trehalose (342 Da) and the IgG1 (≥145,000 Da), it can be assumed that trehalose molecules diffuse much more rapidly through the freeze concentrate than the large globular proteins. Additional studies demonstrate that trehalose crystallization reaches a plateau within 2 weeks of frozen storage (data not shown). Since trehalose crystallization occurs early and the data shows the aggregation kinetics over time at various storage temperatures, this may suggest that molecular mobility is dictating the rate and extent of rearrangement of the frozen media and thereby dictating, the rate and extent of aggregation of the IgG1 monoclonal antibodies. Following fast freezing, mAb3 samples stored at −14° C. start aggregating early but reach a plateau between 3 and 6 months, whereas samples stored at −20° C. start aggregating shortly thereafter, but continue to aggregate in a time dependent fashion and plateau between 6 to 12 months (FIG. 3C). Presumably, samples at the higher temperatures (−14° C. and −8° C.) have more molecular mobility so proteins initially diffuse together and form aggregates. However, as the phase separated solution components (i.e., trehalose) redistribute, proteins are stabilized by interactions with co-localized amorphous trehalose molecules.

Example 5: Effects of Formulation Composition on mAb Stability in Frozen Trehalose Formulations To determine the effects of formulation composition on trehalose crystallization and mAb aggregation during frozen storage, bevacizumab was evaluated at a range of trehalose concentration ([trehalose] range: 0 to 34.2% (wt/v) and bevacizumab concentrations ([bevacizumab] range: 0, 25, and 100 mg/mL). Samples were fast frozen for 12 months at temperatures above (−20° C.) and below (−40° C.) the glass transition temperature and analyzed for trehalose crystallization and protein aggregation using FT-NIR and SEC, respectively.

The results from this study demonstrated that following fast freezing, trehalose crystallizes in frozen solutions stored at −20° C. for 12 months (FIG. 7). However, no trehalose crystallization or mAb aggregation was observed in frozen solutions stored at −40° C. for 12 months. Immediately following fast freezing and scratching, there is a minimal amount of crystallized trehalose (<10% wt/v). However, following 12 months frozen storage at −20° C., trehalose crystallization increases significantly (FIGS. 7A-C).

Figure 7D:
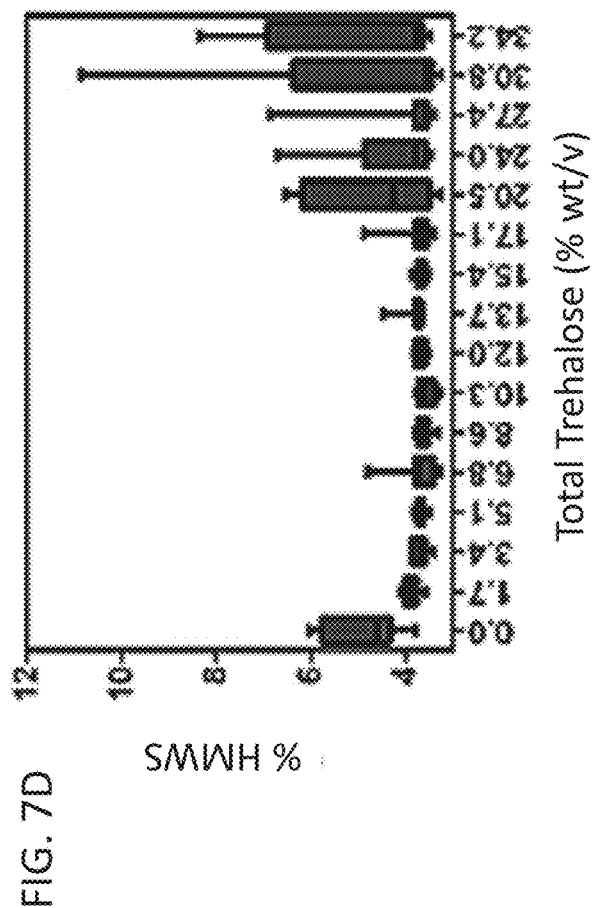
FIGS. 7D and 7E show box plots display the percent high molecular weight species for trehalose formulations with (FIG. 7D) 25 mg/mL bevacizumab, and (FIG. 7E) 100 mg/mL bevacizumab following 12 months storage at −20° C.
Figure 7E:
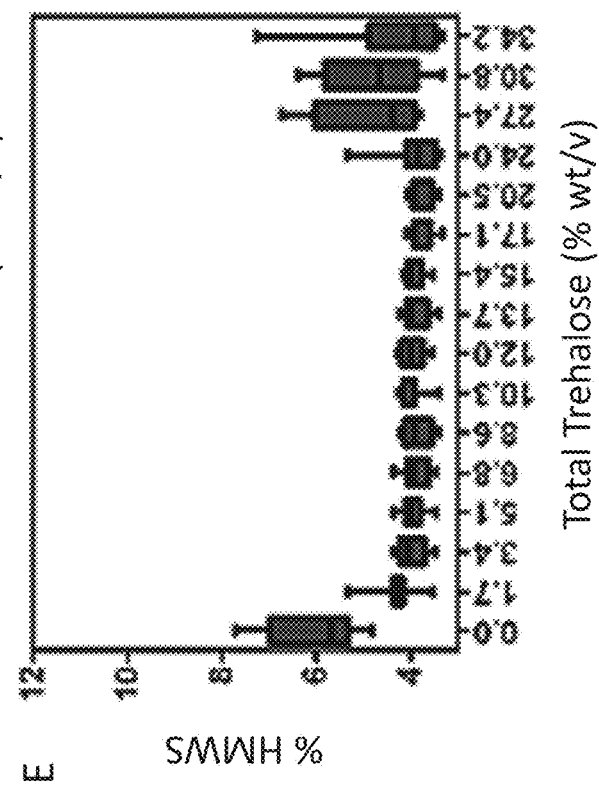

In general, the results demonstrate that increasing the trehalose concentration results in higher percentages of crystallized trehalose. For example, the percent crystallized trehalose increases from 47% to 86% ([bevacizumab]=0 mg/mL), 22% to 61% ([bevacizumab]=25 mg/mL), and 10% to 47% ([bevacizumab]=100 mg/mL) as trehalose concentration increases from 1.7% to 34.2% (wt/v) (FIG. 7). Similarly, bevacizumab aggregation also increased after 12 months frozen storage at −20° C. (FIGS. 7D-E). In general, the results show that there is an optimal range of trehalose that stabilizes bevacizumab solutions during long-term frozen storage. Alternatively, trehalose:mAb ratios above the optimal range result in trehalose crystallization and protein aggregation (FIGS. 7D-E). At trehalose:mAb ratios below the optimal range, there is an increase in protein aggregation but no increase in trehalose crystallization—presumably due to another mechanism (e.g., insufficient cryoprotectant).

The data indicate that the percent of crystallized trehalose formed depends on the concentrations of both protein and trehalose. Interestingly, higher bevacizumab concentration results in lower amounts of trehalose crystallization. For example, at fixed trehalose concentration (1.7% wt/v) increasing the bevacizumab concentration from 0 mg/mL to 100 mg/mL decreases the percent of crystallized trehalose from 53% to 9%.

Figure 8A:
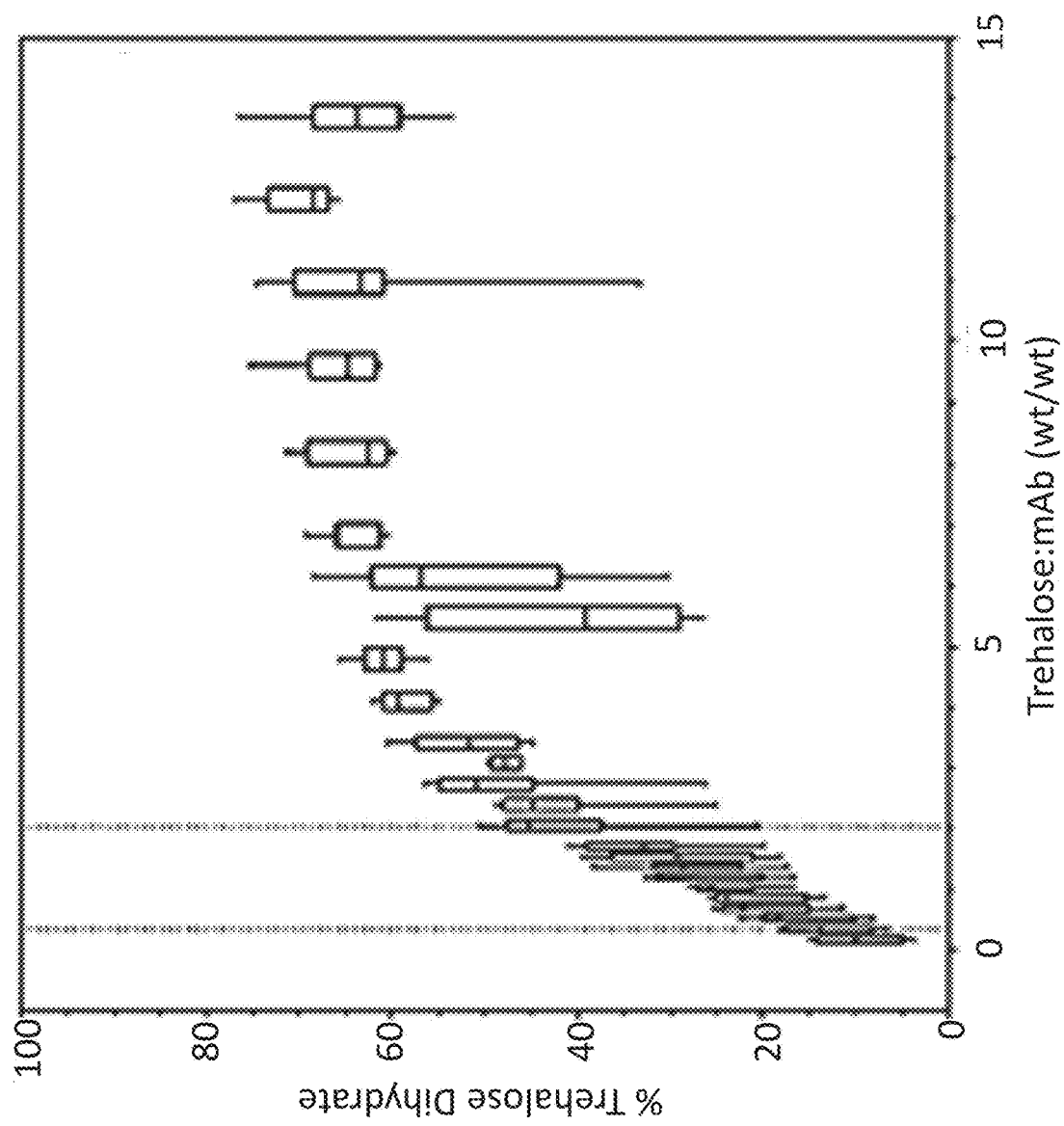
FIGS. 8A and 8B show the percent of crystallized trehalose dehydrate (FIG. 8A), and percent high molecular weight species (FIG. 8B) as a function of total trehalose: mAb ratio (wt/wt). High molecular weight species was measured using HP-SEC and trehalose dihydrate concentration was determined using FT-NIR.
Figure 8B:
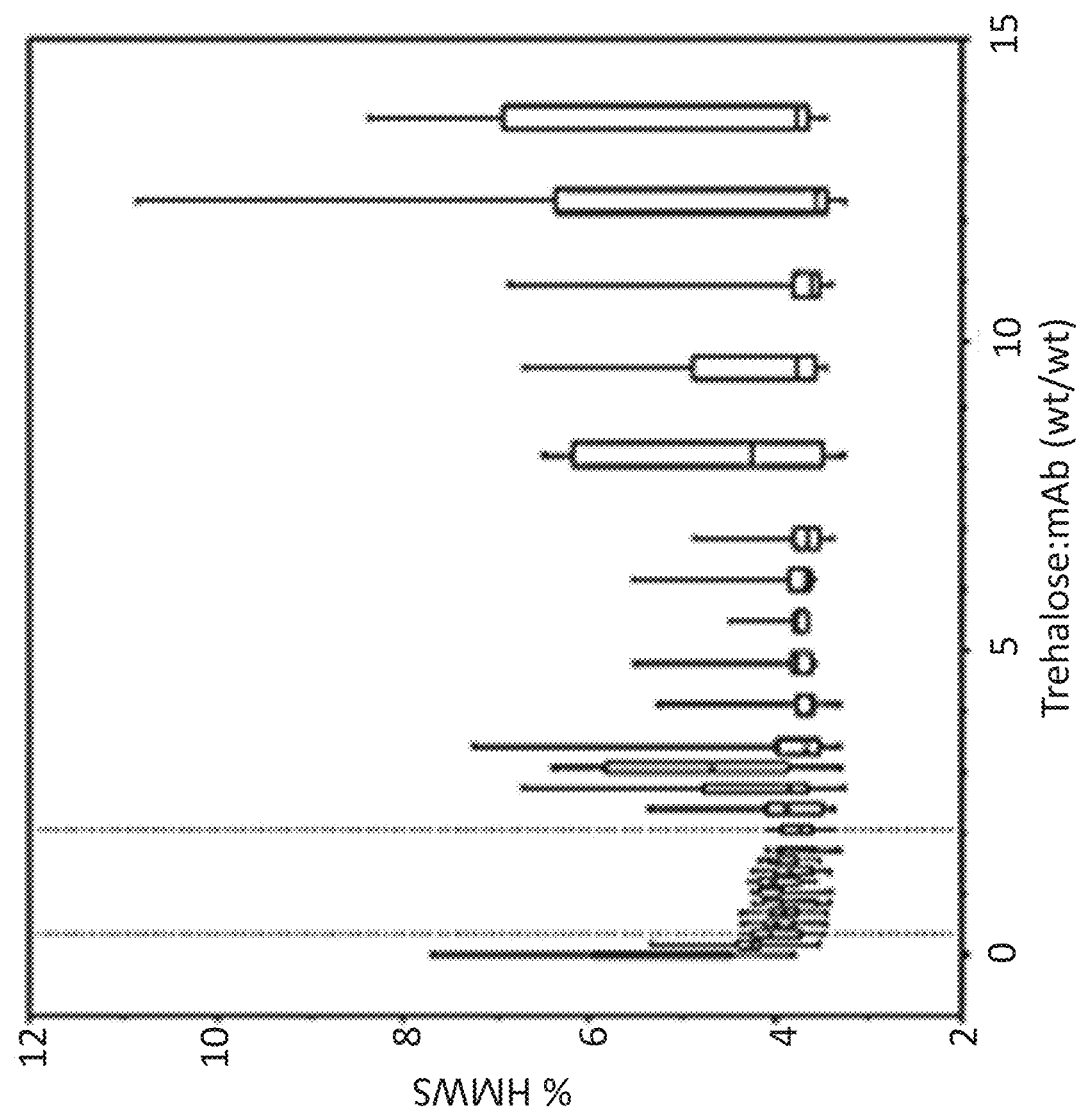

FIG. 8 demonstrates the importance of the trehalose to mAb ratio (wt/wt) on trehalose crystallization (FIG. 8A) and bevacizumab aggregation (FIG. 8B). As shown in FIGS. 8A and B, analysis of bevacizumab physical stability demonstrated that sufficient trehalose:mAb (≥0.2:1 wt/wt) is required to stabilize the bevacizumab solutions during long-term freezing; however, excessive trehalose:mAb (≥2.4:1 wt/wt) results in higher proportions of crystallized trehalose dihydrate and significant increases in bevacizumab aggregation. Presumably, increasing trehalose:mAb results in super-saturation of trehalose in frozen solutions and results in trehalose crystallization and mAb aggregation. These results identify an optimal range of trehalose:mAb (>0.2:1 and <2.4:1 wt/wt) required for physical stabilization of bevacizumab formulations by trehalose during long-term frozen storage.

Stated another way, these results identify an optimal range of mAb:trehalose (>0.417:1 and <5.0:1 wt/wt) required for physical stabilization of bevacizumab formulations by trehalose during long-term frozen storage. For example, as shown in FIG. 7D, using 25 mg/mL bevacizumab, ranges of mAb:trehalose between 0.49 and 1.47 showed low protein aggregation and low sample variation. As another example, as shown in FIG. 7E, using 100 mg/mL bevacizumab, ranges of mAb:trehalose between 0.41 and 1.47 showed low protein aggregation and low sample variation.

Interestingly, polysorbate did not impact the protein stability or phase distribution of trehalose in any of the frozen bevacizumab formulations. For samples with equivalent compositions, the addition of polysorbate (0.04% wt/v) did not result in any measurable changes in trehalose crystallization or protein aggregation.

The results from the formulation composition study indicate that increasing protein concentration decreases the occurrence and extent of trehalose crystallization in frozen samples. These results demonstrate that excessively high trehalose:mAb ratios (≥2.4 wt/wt) result in trehalose crystallization and protein aggregation, but excessively low trehalose:mAb ratios (≤0.2 wt/wt) did not provide adequate cryoprotection for bevacizumab concentrations up to 100 mg/mL. The results identify an optimal range of trehalose:bevacizumab (wt/wt) ratio, 0.2-2.4, capable of physically stabilizing bevacizumab formulations during long-term frozen storage—even for fast frozen (>100° C./min) formulations. Stated another way, these results identify an optimal range of bevacizumab:trehalose (>0.417:1 and <5.0:1 wt/wt) required for physical stabilization of bevacizumab formulations by trehalose during long-term frozen storage.

All patents, patent applications, documents, and articles cited herein are herein incorporated by reference in their entireties.

What is claimed is:

1. A stable aqueous pharmaceutical formulation, the formulation comprising: (a) a monoclonal antibody in an amount of about 25 mg/mL to about 100 mg/mL; (b) trehalose dihydrate in an amount of about 45 mM to about 634 mM; and (c) sodium phosphate in an amount of greater than about 35 mM to about 100 mM; wherein said formulation has a pH of about 5.5 to about 7.0; wherein the weight ratio of said monoclonal antibody to said trehalose dihydrate in the formulation is about 0.49 to about 1.47; wherein the monoclonal antibody is bevacizumab; and wherein the formulation is stable after storage at −20° C. or −40° C. for at least about 6 months.

2. The formulation of claim 1, wherein said monoclonal antibody is in an amount of about 35 mg/mL to about 85 mg/mL.

3. The formulation of claim 1, wherein said monoclonal antibody is in an amount of about 45 mg/mL to about 55 mg/mL.

4. The formulation of claim 1, wherein said monoclonal antibody is in an amount of about 50 mg/mL.

5. The formulation of claim 1, wherein said trehalose dihydrate is in an amount of about 45 mM to about 135 mM.

6. The formulation of claim 1, wherein said trehalose dihydrate is in an amount of about 180 mM to about 634 mM.

7. The formulation of claim 1, wherein said trehalose dihydrate is in an amount of about 60 mM.

8. The formulation of claim 1, wherein said sodium phosphate is in an amount of about 45 mM to about 90 mM.

9. The formulation of claim 1, wherein said sodium phosphate is in an amount of about 50 mM to about 75 mM.

10. The formulation of claim 1, wherein said sodium phosphate is in an amount of about 51 mM.

11. The formulation of claim 1, further comprising a surfactant.

12. The formulation of claim 11, wherein said surfactant is polysorbate or poloxamer.

13. The formulation of claim 12, wherein said surfactant is polysorbate 20 or poloxamer 188.

14. The formulation of claim 11, wherein said surfactant concentration is about 0.01% to about 0.1%.

15. The formulation of claim 11, wherein said surfactant concentration is about 0.01% to about 0.05%.

16. The formulation of claim 11, wherein said surfactant concentration is about 0.04%.

17. The formulation of claim 1, wherein said formulation has a pH of about 5.9 to about 6.5.

18. The formulation of claim 1, wherein said formulation has a pH of about 6.2.

19. The formulation of claim 1, wherein said formulation has a pH of about 6.0.

20. The formulation of claim 1, wherein said monoclonal antibody is not subject to prior lyophilization.

21. The formulation of claim 1, wherein the formulation is stable at −20° C. for at least 12 months, at least 18 months, or at least 24 months.

22. The formulation of claim 1, which is for intravenous (IV), subcutaneous (SQ), intraocular (IO), or intramuscular (IM) administration.

23. An article of manufacture comprising a container holding the stable aqueous pharmaceutical formulation of claim 1.

24. A stable aqueous pharmaceutical formulation, the formulation comprising: (a) a monoclonal antibody in an amount of about 25 mg/mL to about 100 mg/mL; (b) trehalose dihydrate in an amount of about 45 mM to about 634 mM; and (c) sodium phosphate in an amount of greater than about 35 mM to about 100 mM; wherein said formulation has a pH of about 5.5 to about 7.0; wherein the weight ratio of said monoclonal antibody to said trehalose dihydrate in the formulation is about 0.49 to about 0.73; wherein the monoclonal antibody is bevacizumab; and wherein the formulation is stable after storage at −20° C. or −40° C. for at least about 6 months.

25. The formulation of claim 24, wherein said monoclonal antibody is in an amount of about 35 mg/mL to about 85 mg/mL.

26. The formulation of claim 24, wherein said monoclonal antibody is in an amount of about 45 mg/mL to about 55 mg/mL.

27. The formulation of claim 24, wherein said monoclonal antibody is in an amount of about 50 mg/mL.

28. The formulation of claim 24, wherein said trehalose dihydrate is in an amount of about 45 mM to about 135 mM.

29. The formulation of claim 24, wherein said trehalose dihydrate is in an amount of about 180 mM to about 634 mM.

30. The formulation of claim 24, wherein said trehalose dihydrate is in an amount of about 60 mM.

31. The formulation of claim 24, wherein said sodium phosphate is in an amount of about 45 mM to about 90 mM.

32. The formulation of claim 24, wherein said sodium phosphate is in an amount of about 50 mM to about 75 mM.

33. The formulation of claim 24, wherein said sodium phosphate is in an amount of about 51 mM.

34. The formulation of claim 24, further comprising a surfactant.

35. The formulation of claim 34, wherein said surfactant is polysorbate.

36. The formulation of claim 35, wherein said surfactant is polysorbate 20 or poloxamer 188.

37. The formulation of claim 34, wherein said surfactant concentration is about 0.01% to about 0.1%.

38. The formulation of claim 34, wherein said surfactant concentration is about 0.01% to about 0.05%.

39. The formulation of claim 34, wherein said surfactant concentration is about 0.04%.

40. The formulation of claim 24, wherein said formulation has a pH of about 5.9 to about 6.5.

41. The formulation of claim 24, wherein said formulation has a pH of about 6.2.

42. The formulation of claim 24, wherein said formulation has a pH of about 6.0.

43. The formulation of claim 24, wherein said monoclonal antibody is not subject to prior lyophilization.

44. The formulation of claim 24, wherein the formulation is stable at −20° C. for at least 12 months, at least 18 months, or at least 24 months.

45. The formulation of claim 24, which is for intravenous (IV), subcutaneous (SQ), intraocular (IO), or intramuscular (IM) administration.

46. An article of manufacture comprising a container holding the stable aqueous pharmaceutical formulation of claim 24.

47. A stable aqueous pharmaceutical formulation, the formulation comprising: (a) a monoclonal antibody in an amount of about 25 mg/mL to about 100 mg/mL; (b) trehalose dihydrate in an amount of about 45 mM to about 634 mM; and (c) sodium phosphate in an amount of greater than about 35 mM to about 100 mM; wherein said formulation has a pH of about 5.5 to about 7.0; wherein the weight ratio of said monoclonal antibody to said trehalose dihydrate in the formulation is about 0.73 to about 1.47; wherein the monoclonal antibody is bevacizumab; and wherein the formulation is stable after storage at −20° C. or −40° C. for at least about 6 months.

48. The formulation of claim 47, wherein said monoclonal antibody is in an amount of about 35 mg/mL to about 85 mg/mL.

49. The formulation of claim 47, wherein said monoclonal antibody is in an amount of about 45 mg/mL to about 55 mg/mL.

50. The formulation of claim 47, wherein said monoclonal antibody is in an amount of about 50 mg/mL.

51. The formulation of claim 47, wherein said trehalose dihydrate is in an amount of about 45 mM to about 135 mM.

52. The formulation of claim 47, wherein said trehalose dihydrate is in an amount of about 180 mM to about 634 mM.

53. The formulation of claim 47, wherein said trehalose dihydrate is in an amount of about 60 mM.

54. The formulation of claim 47, wherein said sodium phosphate is in an amount of about 45 mM to about 90 mM.

55. The formulation of claim 47, wherein said sodium phosphate is in an amount of about 50 mM to about 75 mM.

56. The formulation of claim 47, wherein said sodium phosphate is in an amount of about 51 mM.

57. The formulation of claim 47, further comprising a surfactant.

58. The formulation of claim 57, wherein said surfactant is polysorbate or poloxamer.

59. The formulation of claim 58, wherein said surfactant is polysorbate 20 or poloxamer 188.

60. The formulation of claim 57, wherein said surfactant concentration is about 0.01% to about 0.1%.

61. The formulation of claim 57, wherein said surfactant concentration is about 0.01% to about 0.05%.

62. The formulation of claim 57, wherein said surfactant concentration is about 0.04%.

63. The formulation of claim 47, wherein said formulation has a pH of about 5.9 to about 6.5.

64. The formulation of claim 47, wherein said formulation has a pH of about 6.2.

65. The formulation of claim 47, wherein said formulation has a pH of about 6.0.

66. The formulation of claim 47, wherein said monoclonal antibody is not subject to prior lyophilization.

67. The formulation of claim 47, wherein the formulation is stable at −20° C. for at least 12 months, at least 18 months, or at least 24 months.

68. The formulation of claim 47, which is for intravenous (IV), subcutaneous (SQ), intraocular (IO), or intramuscular (IM) administration.

69. An article of manufacture comprising a container holding the stable aqueous pharmaceutical formulation of claim 47.

70. A stable aqueous pharmaceutical formulation for intravenous administration, the formulation comprising: (a) a monoclonal antibody in an amount of from about 25 mg/mL to less than or equal to about 100 mg/mL; (b) trehalose dihydrate in an amount of about 50 mM to about 600 mM; and (c) a sodium phosphate buffer in an amount of greater than about 35 mM to about 100 mM; wherein said formulation has a pH of about 5.5 to about 7.0; wherein the weight ratio of said monoclonal antibody to said trehalose dihydrate in the formulation is greater than or equal to 0.49 and less than or equal to 1.47; wherein the monoclonal antibody is bevacizumab; and wherein the formulation is stable after storage at −20° C. or −40° C. for at least about 6 months.

71. A stable aqueous pharmaceutical formulation for intravenous administration, the formulation comprising: (a) a monoclonal antibody in an amount of from about 25 mg/mL to less than or equal to about 100 mg/mL; (b) trehalose dihydrate in an amount of about 50 mM to about 600 mM; and (c) a sodium phosphate buffer in an amount of greater than about 35 mM to about 100 mM; wherein said formulation has a pH of about 5.5 to about 7.0; wherein the weight ratio of said monoclonal antibody to said trehalose dihydrate in the formulation is greater than or equal to 0.49 and less than or equal to 0.73; wherein the monoclonal antibody is bevacizumab; and wherein the formulation is stable after storage at −20° C. or −40° C. for at least about 6 months.

72. A stable aqueous pharmaceutical formulation for intravenous administration, the formulation comprising: (a) a monoclonal antibody in an amount of from about 25 mg/mL to less than or equal to about 100 mg/mL; (b) trehalose dihydrate in an amount of about 50 mM to about 600 mM; and (c) a sodium phosphate buffer in an amount of greater than about 35mM to about 100 mM; wherein said formulation has a pH of about 5.5 to about 7.0; wherein the weight ratio of said monoclonal antibody to said trehalose dihydrate in the formulation is greater than or equal to 0.73 and less than or equal to 1.47; wherein the monoclonal antibody is bevacizumab; and wherein the formulation is stable after storage at −20° C. or −40° C. for at least about 6 months.

73. A stable aqueous pharmaceutical formulation for subcutaneous or intraocular administration, the formulation comprising: (a) a monoclonal antibody in an amount of from about 25 mg/mL to less than or equal to about 100 mg/mL; (b) trehalose dihydrate in an amount of about 150 mM to about 400 mM; and (c) a sodium phosphate buffer in an amount of greater than about 35 mM to about 100 mM; wherein said formulation has a pH of about 5.5 to about 7.0;

wherein the weight ratio of said monoclonal antibody to said trehalose dihydrate in the formulation is greater than or equal to 0.49 and less than or equal to 1.47; wherein the monoclonal antibody is bevacizumab; and wherein the formulation is stable after storage at −20° C. or −40° C. for at least about 6 months.

74. A stable aqueous pharmaceutical formulation for subcutaneous or intraocular administration, the formulation comprising: (a) a monoclonal antibody in an amount of from about 25 mg/mL to less than or equal to about 100 mg/mL; (b) trehalose dihydrate in an amount of about 150 mM to about 400 mM; and (c) a sodium phosphate buffer in an amount of greater than about 35 mM to about 100 mM; wherein said formulation has a pH of about 5.5 to about 7.0; wherein the weight ratio of said monoclonal antibody to said trehalose dihydrate in the formulation is greater than or equal to 0.49 and less than or equal to 0.73; wherein the monoclonal antibody is bevacizumab; and wherein the formulation is stable after storage at −20° C. or −40° C. for at least about 6 months.

75. A stable aqueous pharmaceutical formulation for subcutaneous or intraocular administration, the formulation comprising: (a) a monoclonal antibody in an amount of from about 25 mg/mL to less than or equal to about 100 mg/mL; (b) trehalose dihydrate in an amount of about 150 mM to about 400 mM; and (c) a sodium phosphate buffer in an amount of greater than about 35 mM to about 100 mM; wherein said formulation has a pH of about 5.5 to about 7.0; wherein the weight ratio of said monoclonal antibody to said trehalose dihydrate in the formulation is greater than or equal to 0.73 and less than or equal to 1.47; wherein the monoclonal antibody is bevacizumab; and wherein the formulation is stable after storage at −20° C. or −40° C. for at least about 6 months.

76. A method of reducing aggregation of a therapeutic monoclonal antibody, comprising formulating said monoclonal antibody in a formulation comprising: (a) said monoclonal antibody in an amount of about 25 mg/mL to about 100 mg/mL; (b) trehalose dihydrate in an amount of about 45 mM to about 634 mM; and (c) sodium phosphate in an amount of greater than about 35 mM to about 100 mM; wherein said formulation has a pH of about 5.5 to about 7.0; wherein the weight ratio of said monoclonal antibody to said trehalose dihydrate in the formulation is greater than or equal to 0.49 and less than or equal to 1.47; wherein the monoclonal antibody is bevacizumab; and wherein the formulation is stable after storage at −20° C. or −40° C. for at least about 6 months.

77. A method of reducing aggregation of a therapeutic monoclonal antibody, comprising formulating said monoclonal antibody in a formulation comprising: (a) said monoclonal antibody in an amount of about 25 mg/mL to about 100 mg/mL; (b) trehalose dihydrate in an amount of about 45 mM to about 634 mM; and (c) sodium phosphate in an amount of greater than 35 mM to about 100 mM; wherein said formulation has a pH of about 5.5 to about 7.0; wherein the weight ratio of said monoclonal antibody to said trehalose dihydrate in the formulation is greater than or equal to 0.49 and less than or equal to 0.73, wherein the monoclonal antibody is bevacizumab; and wherein the formulation is stable after storage at −20° C. or −40° C. for at least about 6 months.

78. A method of reducing aggregation of a therapeutic monoclonal antibody, comprising formulating said monoclonal antibody in a formulation comprising: (a) said monoclonal antibody in an amount of about 25 mg/mL to about 100 mg/mL; (b) trehalose dihydrate in an amount of about 45 mM to about 634 mM; and (c) sodium phosphate in an amount of greater than 35 mM to about 100 mM; wherein said formulation has a pH of about 5.5 to about 7.0; wherein the weight ratio of said monoclonal antibody to said trehalose dihydrate in the formulation is greater than or equal to 0.73 and less than or equal to 1.47, wherein the monoclonal antibody is bevacizumab; and wherein the formulation is stable after storage at −20° C. or −40° C. for at least about 6 months.

\* \* \* \* \*

UNITED STATES PATENT AND TRADEMARK OFFICE
CERTIFICATE OF CORRECTION

| | |
|---|---|
| PATENT NO. | : 11,370,833 B2 |
| APPLICATION NO. | : 16/026481 |
| DATED | : June 28, 2022 |
| INVENTOR(S) | : Lan Le and Brian Connolly |

It is certified that error appears in the above-identified patent and that said Letters Patent is hereby corrected as shown below:

In the Claims

In Claim 35, Column 92, Line 63, delete "polysorbate" and insert --polysorbate or poloxamer--, therefor.

In Claim 74, Column 95, Line 17, delete "0.49" and insert --0.49--, therefor.

Signed and Sealed this
Seventh Day of November, 2023

Katherine Kelly Vidal
*Director of the United States Patent and Trademark Office*